United States Patent
Sims

(10) Patent No.: US 9,540,699 B2
(45) Date of Patent: Jan. 10, 2017

(54) METHODS OF DIAGNOSING INCREASED RISK OF DEVELOPING MRSA

(71) Applicant: William Beaumont Hospital, Royal Oak, MI (US)

(72) Inventor: Matthew Sims, Troy, MI (US)

(73) Assignee: WILLIAM BEAUMONT HOSPITAL, Royal Oak, MI (US)

( * ) Notice: Subject to any disclaimer, the term of this patent is extended or adjusted under 35 U.S.C. 154(b) by 408 days.

(21) Appl. No.: 14/209,090

(22) Filed: Mar. 13, 2014

(65) Prior Publication Data

US 2014/0272966 A1    Sep. 18, 2014

Related U.S. Application Data

(60) Provisional application No. 61/779,307, filed on Mar. 13, 2013.

(51) Int. Cl.
*C12Q 1/68* (2006.01)

(52) U.S. Cl.
CPC ............. *C12Q 1/689* (2013.01); *C12Q 1/6883* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,989,431 A | 11/1999 | Evans et al. | |
| 6,287,766 B1 | 9/2001 | Nolan et al. | |
| 6,316,230 B1 | 11/2001 | Egholm et al. | |
| 6,322,980 B1 | 11/2001 | Singh | |
| 6,358,679 B1 | 3/2002 | Heid et al. | |
| 6,383,756 B1 | 5/2002 | Hoehe et al. | |
| 6,410,231 B1 | 6/2002 | Arnold et al. | |
| 6,448,407 B1 | 9/2002 | Lee et al. | |
| 6,468,742 B2 | 10/2002 | Nerenberg et al. | |
| 6,503,710 B2 | 1/2003 | Gut et al. | |
| 6,514,700 B1 | 2/2003 | Singh | |
| 6,548,256 B2 | 4/2003 | Lienau et al. | |

OTHER PUBLICATIONS

Bosserhoff, Anja-Katrin, et al. Use of Capillary Electrophoresis for High Throughput Screening in Biomedical Applications. A Minireview. Combinatorial Chemistry & High Throughput Screening, 2000, 3, pp. 455-466.
Buehlmann, M., et al. Highly Effective Regimen for Decolonization of Methicillin-Resistant *Staphylococcus aureus* Carriers. Infection Control and Hospital Epidemiology, Jun. 2008, vol. 29, No. 6, pp. 510-516.
Charrin, Stephanie, et al. The Ig Domain Protein CD9P-1 Down-regulates CD81 Ability to Support Plasmodium yoelii Infection. The Journal of Biological Chemistry, 2009, vol. 284(46): pp. 31572-31578.
Chen, Song, et al. FAM129B/MINERVA, a Novel Adherens Junction-associated Protein, Suppresses Apoptosis in HeLa Cells. The Journal of Biological Chemistry, 2011, vol. 286, No. 12, pp. 10201-10209.
Chen, X., et al. Single nucleotide polymorphism genotyping: biochemistry, protocol, cost and throughput. The Pharmacogenomics Journal 2003, vol. 3, pp. 77-96.
Gerstein, Mark B., et al. What is a gene, post-ENCODE? History and updated definition. Genome Research 17:669-681 (2007) genome.cship.org.
Guttman, Andras, et al. Ultrathin-layer gel electrophoresis of biopolymers. Electrophoresis 2000, 21, pp. 3952-3964.
Hirota, Tetsuya, et al. Micro Extraction of DNA from Whole Blood and Amniocytes. Jpn. J. Human Genet. 34, 217-223, 1989.
Jain, KK. Applications of biochip and microarray systems in pharmacogenomics. Pharmacogenomics 2000, 1(3): 289-307.
John, S.W.M., et al. A rapid procedure for extracting genomic DNA from leukocytes. Nucleic Acids Research, 1990 vol. 19, No. 2 p. 408.
MacBeath, Jonathan R.E., et al. Automated Fluorescent DNA Sequencing on the ABI PRISM 377. Methods in Molecular Biology, 2001 vol. 167:119-152.
Meinkoth, Judy, et al. Hybridization of Nucleic Acids Immobilized on Solid Supports. Anal. Biochem. 1984 138:267-284.
Meldrum, Deirdre. Automation for Genomics, Part Two: Sequencers, Microarrays, and Future Trends. 2000 Genome Res. 10:1288-1303.
Montpellier, Claire, et al. Interacting Regions of CD81 and Two of its Partners, EWI-2 and EWI-2wint, and Their Effect on Hepatitis C Virus Infection. 2011 J. Biol. Chem 286(16) pp. 13954-13965.
Oishi, Hisashi, et al. Delayed cutaneous wound healing in Fam129b/Minerva-deficient mice. J. Biochem, 2012; 152 (6):549-555.
Old, William M., et al. Functional Proteomics Identifies Targets of Phosphorylation by B-Raf Signaling in Melanoma. Mol. Cell 2009 34(1):115-131.
Palmer, Nicholette D., et al. A Genome-Wide Association Search for Type 2 Diabetes Genes in African Americans. 2012 PLOS ONE 7(1):e29202.
Proudnikov, Dmitri, et al. Chemical methods of DNA and RNA fluorescent labeling. Nucleic Acids Research 1996, vol. 24, No. 22 pp. 4535-4542.
Ronaghi, Mostafa Pyrosequencing Sheds Light on DNA Sequencing. Genome Res. 11:3-11, 2001.
Ronchi, Cristina L., et al. Single Nucleotide Polymorphism Microarray Analysis in Cortisol-Secreting Adrenocortical Adenomas Identifies New Candidate Genes and Pathways. Neoplasia vol. 14, No. 3, Mar. 2012 pp. 206-218.

(Continued)

*Primary Examiner* — Juliet Switzer

(74) *Attorney, Agent, or Firm* — Honigman Miller Schwartz and Cohn LLP; Thomas A. Wootton; Jonathan P. O'Brien

(57) ABSTRACT

A method for diagnosing increased risk of developing Methicillin-resistant *Staphylococcus aureus* (MRSA) hospital-acquired (HA-MRSA) or community-acquired MRSA (CA-MRSA) which includes obtaining a biological sample from a subject, detecting in the sample a single nucleotide polymorphism (SNP) in the FAM129B gene at position 17 of SEQ ID NO 1, and comparing the nucleotide at position 17 of SEQ ID NO. 1 in the sample with the nucleotide at position 17 in SEQ ID NO. 1, wherein an adenine at position 17 of SEQ ID NO. 1 in the sample indicates an increased risk of developing MRSA or CA-MRSA in the subject.

11 Claims, No Drawings

(56) References Cited

OTHER PUBLICATIONS

Saiki, Randall K., et al. Primer-Directed Enzymatic Amplification of DNA with a Thermostable DNA Polymerase. Science (1988) 239:487-491.

Schofield, Peter, et al. Molecular Beacons: Trial of a Fluorescence-Based Solution Hybridization Technique for Ecological Studies with Ruminal Bacteria. Applied and Environmental Microbiology 1997, vol. 63, No. 3 pp. 1143-1147.

Tyagi, Sanjay, et al. Molecular Beacons: Probes that Fluoresce upon Hybridization. Nature Biotechnology 14:303-308, 1996.

Watts, David, et al. Automated Fluorescent DNA Sequencing on the ABI Prism 310 Genetic Analyzer. Methods Mol. Biol. 2001 vol. 167:153-170.

Yang, T.L., et al Genetic variants in the SOX6 gene are associated with bone mineral density in both Caucasian and Chinese populations. Osteoporos Int. 2012; 23(2):781-787.

Yates, John R. Mass Spectromoetry from genomics to proteomics. 2000 Trends Genet. 16:5-8.

SEQUENCE LISTING

```
<160> NUMBER OF SEQ ID NOS: 3

<210> SEQ ID NO 1
<211> LENGTH: 33
<212> TYPE: DNA
<213> ORGANISM: Homo sapiens

<400> SEQUENCE: 1
gggggcaagt tagtcaacct gtctgagtct tag                33
```

<210> SEQ ID NO 2
<211> LENGTH: 33
<212> TYPE: DNA
<213> ORGANISM: Homo sapiens

<400> SEQUENCE: 2
gggggcaagt tagtcaccct gtctgagtct tag                               33

<210> SEQ ID NO 3
<211> LENGTH: 73651
<212> TYPE: DNA
<213> ORGANISM: Homo sapiens

<400> SEQUENCE: 3
caggaactgg gccagttccg gtcccttcct tttgggctc tcactctgga ggatggggtg      60
gatgggaggt aagacttgtg cacaagtccc caggacacaa ggcacacggg gttctttttt    120
gtttgtttgt ttagagagga ggttttgctc tgtcactcag gctggagtgc agcggaatga    180
tcatagctca atgcagcctc aaactcctgg gctcaaggga tcctcacttc ttgacctccc    240
aaagcgtcat aggcttaagg cactacagca cccactgaca aggggttctt tttctttttc    300
ttttcttttc ttttttttt ttaggcggag tttcactctt gtcacccccgg ctggactgca    360
atggcgagat ctcgcctcac tctcactgca acctccgcct cccagattca gcgattctc    420
ctgcctcagc ctcctgagta gctgggatga caggccccca ccgccatgcc cagctaattt    480
ttttgtattt ttagtagaga cggtttcacg atgttggcca ggctggtctt gaactcctga    540
gctcagatga tccacctgcc tcggtctcct aaagtgctgg gattacaggt gtaagccatg    600
gcgcctggcc actttttttt ttttttttt ttttgagac caagtctcac tctgttgccc    660
aggctggagt gcagtggctg gatcttggct cactgcatcg tctgcctcct gggttcaagg    720
gattcctcat gcctcagcct cccggatggg atttcaggca caggccacta cgcccagcta    780
aattttttt tttttttttg agatggagtc ttgctctgtc tctcaggctg gagtgcagtg    840
gcgcgatctc agctcactgc aacctccgcc tcccagatac aagtgattct cctgcttcag    900
cctcccaagt agatgggatt tcaggcaccc accaccacac ccagctaatt ttttgtgtt    960
tttagtagag acagggtttc actgtgttgg ccaggctggt ctcaaattcc tgacattgtg   1020
agccacctgc ctcagcctcc caaagtgctg agattacaag tgtgagccac tgtgactggc   1080
ccaacatttt ttttaatta aaaaattaaa gccaggtgta gtggtgcatg cctgtagtcc   1140
cagctactca ggaggctggg tcggaggat tgtttgagcc caggagtttg aggctgcagc   1200
aagccatgat caactcactg cactccagcc tgggttacag agcaagaggt cttatccctg   1260
aaacaaacaa acaaacaaaa agatatagca gagaagccca ttttgtgttt gagaaagagc   1320
tgaactctag gattggatct ggaggatggt gtggaagcg tggggtattg gatctggagg   1380
atggtgtggg aagcgtgggg tattggatct ggaggatggt gtggaagcg tgggtattg   1440
gatctggagg atggtgtggg aagcgtgggg tattggatct ggaggatggt gtggaagtg   1500
tggggtattg gatctggagg atggtgtggg aagtgtgggg tattggatct ggaggatggt   1560
gtggaagtg tggggtattg gatctggagg atggtgtggg aagcgtgggg tattgcagct   1620
ctaaagtagg cagagctatg tatggtctc atcctcatct cttaatttt ttgggggag    1680
ggtggacaca gtctcgctct gtcacccagg ctgcagtaca gtggcgcaat ctcggctcac   1740
tgcaacccct gcctctctgg ttcaagtgat tcttgtgcct cagcctcccg agtagctggg   1800
attacagacg tgcaccacca cgcctggcta attttttgtat ttttagtaga cgggctttt   1860

```
caccatgttg gccaggctgg tctcaaactc ccgacctcag gtgatccgcc cacctcggcc   1920
tctgaaagtg cgtgagccac tgcacctggc ctcatctgtt actttaaaat aaaataacaa   1980
taaattattt aaaaatagag gctgggcatg gtgccttaca cctgtaatcc cagcactttg   2040
ggaggccgag gcaggtggat cacaaggtta ggagtttgag actagtctgg tcaacatggt   2100
gaaacccccgt ctctactaaa aatacaaaaa ttagccggac gttgtggcac ttggggaggc   2160
tgaggttgca gtaagctgag atggcgccac tacactccag cctggtgaca gagcaagact   2220
ctgtcttggg aaaaaaaaa atagagacga ggtcttgcta tgttgcccag gctggtctca   2280
aactcctggg ctcaagcgat cctcctgcct cagcctccca agtgttggg attacaggcg   2340
tgagccactg tgcctgatct catcctcatc tcttacttat acctcatgaa gcctcagttt   2400
tctctcctgt aaagtgggtg ttccccaaaa gttgtgacca ttcaatgagg cagaagctat   2460
aaagcactga actgagcaca ggagcctgca atgaacgggc gcttccatta tctttatcat   2520
cctgaagtta tttctcactc cctgcctgtc tgctggcact tcagcggccc cctgcctgac   2580
ttcagtgctg ttggatccaa ccacggaatt tgtgcctggg aaggcggtaa ggcaccccct   2640
tcctggaagt ttacaagcag aagctctgca cagtagcaga ggcccacatg cactatagaa   2700
gggactttgt accccatgat gtgtcatggc cactgcaggc atgagtgttt cagtataggt   2760
ctatgaacaa acctgtgagg tcccaaggac caggtgggtc cctcactgtc acgttcccct   2820
ccagtgccca ggatagtgtt ctgcacatca tacgtgctcc ctcaagctcc cattgcgact   2880
gacgctagtg atgtcatgtc gaaggaggac agtcctggtc ctcagagaga aagatttatt   2940
taaacagata attgcacaca cacaaaatca tgttgaatgt gatgcttgcc atgaaggagg   3000
agtttaggac actggggagg gggtgataat aatggcaggc ctgacctagt agggggcag   3060
ggtgcagaaa tgtcctctct gatgaagggt aattagctga ggttgaaggc tgaatgctgc   3120
ttggtggggc aagatgcggg aaaaaaatcc atgtttcaca cagccaggca cggtggctca   3180
cgcctgtaat cccagcactg tgggagccaa ggcgggcgga tcacctgagc tcaggagttt   3240
gagaccagcc tgatcaatat ggtgaaaccc tgtctctact aaaaatacca gaattaacca   3300
ggcatagtgg cgggtgcctg taatcccagc tactcaggag gctgaggcag gagaatcgct   3360
tgagcctggg aggtggaggt tgcagtgagc agagatcccg ccactgcact ccagcctgga   3420
cgacagagca agactccatc tcaaaagaaa aaaaaaaaa aagggccca gcacagtggc   3480
tcatgcctgt agtcccagca cttttgggaag ctggggtggg tggatcacga ggtcaggagt   3540
tcaagaccat cctggccaag atggtaaaac cccgtctcta ctaaaaatac caaaattagc   3600
caggcgtggt ggcaggaacc tgtaatccca gctacttgag agtctgaggc agagaattgc   3660
ttgaacccag gaggctgagt ttgcagtgag ccgagatcgc accactgcac tccagcctgg   3720
gtgacagagc gagactccat ctcaaaaaaa aaaaaaaag aatccatatt tcataagctg   3780
tgaggtggga tggagcaggg ctagtttgag gatgtgaaat ctcagtgtgg ctagagaatg   3840
gggagggaa gtgggggag ggactggcag ggcccccag tgccatgtct ggagtctttc   3900
tctccaggac agtggaagcc acagaaggtt agaagtgggg gaatggcaag gtcgtatctg   3960
tgtttacaac aattcctctg gctcccagtg aggaatgcat gggggctgg aggcaggag   4020
gccagttccc tggacttggg gtggcagtgg agctggggag aggtgacagc ttggccactg   4080
aaagagtaag agggagttta gcagcctgag gccaggtgac agacggaaca ggctgtaagc   4140
tacggaccttt tccaccaccc aacagttaat aaagagagga ggtccgggct gggtgccagg   4200
gtcccttctg cacaatgggc catgccaact gggtaaacag aggtagatac atgatattcc   4260
```

```
ttaaaaacaa aatcctgatt cattcacact ccttgctgtt tactggaggt gtttgttttt   4320
tttctcctgg tctatttcag gtttgacagg tttgtgggga gagcagagct gggactccgt   4380
gccaactggg agggagaggg actcatgggg agagaaaggg cctctccttc ttcctacagg   4440
actagcaagg ggtcttgggc tgggctcctg cggaatgctc ttgggcaaat tgctttcctt   4500
ctctgagtct cggtccaagc tctggctctg accgtctgaa ccctcccttt taaagccaaa   4560
tattattatt cttcgccctt ggatccctgc ttccaaatat gcttgaggat gtggtgggca   4620
ggggaggggc ggggcaggtt tgcagggagg cagtgggcag aagccacttc cagagaaagg   4680
cctgatgagt caggacctgt aggtggcatt ctctgttcaa gaggggcagg cccagcaagt   4740
gggcagggag aacctttcct ctctgctcca gatgtagacc attgccaccc tttgtccaca   4800
gccctggcat tttcaaccag gttctggggc ctgagccaag aaaagggagt gggagcccct   4860
ggtgaataga gacagcgtcc agagtcttag aaaaagaaca gatatccctc tgccttgcag   4920
atttcagaaa tccttgctat agaaagaact cttacaaatc aataagaaaa agatagacat   4980
tcccacagaa aagcaggcag aggatataaa ttttaaaaac cacaaatggc caggctgggt   5040
acggtggctc atacctgtaa tcccagcact ttgagaggcc aagggaggca gatcacttgt   5100
ggtcaggagt tccagaccag cctggccaac atagcaaaac cccatttcca ctaaaaatac   5160
aaaaattagc caggcgtggt ggcaggtgcc tgtaatccca gctacttggg aagctgaggc   5220
aggagaattg cttgaaccca gaaggtaggt agagattgca gtgagcagag atcgtgccac   5280
tgcactctag cctgggcaac agaacgagac cctgtctcga aataaacaaa ataaaaataa   5340
aacccacaaa tggccactaa atgtgtgaaa agatgtttcc atttactcaa aagtaacaag   5400
gggacatcaa aatggcctcc agcgtgaggg caggggtttc cagcatttta gagttgagaa   5460
attctctgat gtcaaacttc ctggaatcct tcatagtgct gatgactatg tttattttc    5520 tttccttgaa aaaaaaaaaa gggcaaataa cttcattcct tccccaccca aagactgtaa   5580 cttttttta ttacaataat tgatttctta acatatagta gagagagttg agaaagttta    5640
aagagcttta caatctttcc agagtgaaaa aaaaaaacaa caaattctgt tctggatgct   5700
caggctgcct ccccatctgg ggtcccacca gtccatgcca gggcccaccc ctccttccct   5760
gcaggaagtc ctagatcagc catctggctt aggccccaca aggactcacc ttgcttcctt   5820
ttgctcacac tcacgccttt acctgtcacg ccttctctgt gcctacctgt tccagtgttt   5880
gaacaaggat tgctgtatac atacaatgga atatatatac atacgtacat acatatatct   5940
ataaagaggg aaggtctcac tctgtcaccc aagctggagt gtagcggcga gatcacagca   6000
cactgcagcc tcaaactcct gggctcaagg tcttcctgct ttggcctcct agtagctggg   6060
actacaagca tgcaccacca ggcccagcta attttttta aaaattattt aacgacgggg   6120
tctcattctg ttgcccatgc tcgtctcaaa ctcctggcct caagcaatcc tcttgcctca   6180
gcttcccaga gtgctggcat tatgagtgtg agccaccgtg ctcagcctga atatcattaa   6240 aaaaaaatc ctcgcaacaa tttattcaac tctaaaatgg gctttatcat tactacccca    6300
gaagctgtga ggacagtagg aggcagaaaa gtccttggtg tgacacctgg tctgtggtcc   6360
atctccataa atggcagctc ttcctgaacc ttcttcaagc aggctccttc ttgccaatca   6420
ggtcccaagg catcatctcc tcctccttcc tagaccactt tcctagatgg catcccaccc   6480 caacccccact tgtcaccta tcccatctta atgtttatta ctctctgaag tcatttatt    6540 tatttgttgt attttttcat aagactataa cctctatgaa gacgaggacc gtgactttct   6600
```

```
tgcatactga tttatcccca atacctagaa tagcatccaa cacatagtag gtgcttgcat    6660 gtttatttt tcactttaaa ataaatggtg gctcacacct gtaatcccag cactctggga    6720
ggcttaggcg ggaggatccc ttgagctcag gagttggaga ccagcctggg cagcatggtg    6780
agatcccatc tctatgaaaa acatttttta attagctggg tgtggtaacc caagggtgag    6840
attggaggat gccttgagcc caggaggcca aggctgcact gagtccatgt ttgcaccact    6900
gcactccagc ctgggcgaca cagagagacc ttgtctcaaa aataaaaata aaataaactt    6960
tgttgaagta taattttgat ataataaaat gcatccgttt gatgcatctg tacagtttga    7020
taaatttaga taaatatgtt ctcttaccaa cacctcagtc aagacatagg accattttta    7080 tcccctaaa gttccctcca gattttttt tgccatcaat tctccttcat ccatcccta    7140 gacaaggcag ttttttttg gtgtgaaatg aatgaatctt gaattgtcag ggactggccc    7200
cagatttgcg gagagctatt cacatgtgtg catagcaccc tactgttcac aatgcctttc    7260
cactttctgt tttttttctttt ggttttgttt tgttttttaat ggagtctcac tctgtcacca    7320
ggctggagtg cagtggcacg atcttggctc actgcaacct ctgcctcccg ggttcaagcg    7380
attcttctgc ctcagccttc tgagcagctg ggactacagg cgcgtgccac catgcccagc    7440 taattttgc atttttaata gagatggggt ttcaccatgt tggccagact ggtctcagac    7500
tcctgatctc gtgatctgcc tgcctcggcc tcccaaaatg ctgagattac aggcgtgagc    7560
cattgcgccc ggccgccttt ccactttcat ctcatgtgcc tctcacatat gaggccatgg    7620
atgctcagat ggattaggtg acatgtgaca gaaggtctcc aaagcaagag gagaccttt    7680 ggatgctcaa gttgcctccc catctggggt cccaccctgg gccagggagg aaccccgtccc   7740 tgggccaggg aggaacccgt ccctgggcca ggggcctcac atggtaggca ggctgtgggt    7800
gttccaggct tgggtgtgcc acgaagctg gggaaaggcc actgtggccc catctctaac    7860 cccctggcc taggcctcca gcccagccaa gaagatgcct ctggtgtcca gatgccagct    7920
agctccagct agctccctcc tgggcagaac agacccctgca gtttgggcta tgagaaaaat    7980
gaaaagaggt tatcagcatc acttgcttct ggttgctcag agagaatcag acactgggtg    8040
ccaggagact tggcctttgg ccaggttctc cctctgcctc actgtgtgcc cttagcaagt    8100
cactttccct ctctgggcct cagtttccac ctctataaaa ggaaactagt gatccctaac    8160
cagcatgact tcaactccac ctgatgatga ctctttgacg catgaatgca tcccggccct    8220
caaaggctgg gcccctgccc atgctgtccc cactccctgg aatgctgttt ctcagtatct    8280
gctgtcaaaa gtcttgtttt tcaacttcca gttctggtcc tacccctct gtgattttcc    8340 ttaaaacaga atgttctgct ccttcctcaa gcttctctaa gcttcttgagg gcagggacta    8400 tgaataatag aatgacacgt tctgttcatt gagagatgat ggaccctggt gccaggcact    8460
atgctgggca ctttgtgata tcatttaacc ctcccgcaaa aagcatcatt tctcttttgac    8520 agatgaggta gctgaagttc aaaggggtaa tgccacttgt ccagggtcac agaggggagg    8580
gcagcttggg cttccttctc tttcaccc cagcatctag cagagggcct ggcacacagg    8640
tgttgaccac ccattgctga atgactggta agtgactgaa tgcatgaatg aatgcctgca    8700
tcactttaat ccatttcaaa cctacctcct gtggtgtgca caggcctgaa gtacaggtgc    8760
tcagcaaatt taactgttat catcatcact tcctgcctta tgccacagtc acactaagag    8820
ctgcccaata acaacgtgaa atgcatgaga gaagtggtga gtgcttagtt accaggggtc    8880
aacaagcaga aagtggatgg ccttgtccca gtgcagatca ggagatctga gcaccagcag    8940
ccaaaggatt gagatctggg gatcccactg gttaacctga ctgtctcccc tgccagcttg    9000
```

```
ggaggtcctg aaactgaaac acattcccct ggcactgcga cccacccatg cccagcccca   9060
taggctggtg cctgtcggtc tccgggtttt gattctggta gtcttttgca aactgtaaag   9120
tgctactgct ttttcctttt ctgatttgct ctgtccccca agccgcctcc cgagtgaaat   9180
gcccatatgc tgagcctgag gcaagcccgc ctggcactgg ggcgggggtg ccttcgggcc   9240
cgagccttcc ccaccccctt cctatagctg ttgtgcaaga ccagcgggca ccttctggg   9300
ggcaggtcga atcaaggcca gggaacttcc tgagcgcggg cagtggcggg cgggacttgg   9360
gggggcaggg ggcactgttc agggtagagg aggggcgaa cgccgaattc cggcccgtag   9420
gtccaggcgt cccctgccag tgccccacat cctcctcggc gcgattctttt cccgcgcgg   9480
gcaaggttgg ggaggggagg ggggtgacac tcaggctgga gtcccccaga gcaccccag    9540
tttttcagat gtccccacca gccccgtctc tttctctgct taggtacagg gcgggtgcgc   9600
tcttcgcagt ctctccgcgg tctcccttc tgggaccttc tctttgtctc cttctccagg    9660
gcggtcccgg cgtccaccgc ccctgtgccc cgcccgccgg aggcagcgga ggggcgggg    9720
catacggggc gggccctgga ggggctgggt ggggcgcagg ggggtgcagg accgagggcg   9780
gggcggggcg gggcggggtg ggacgcgcg ggcgcagggc agcgggcggg gaggggcgg    9840
ggttggcctg cgggggcgtg gtctggtggg gcggagcggg gcgccggggt gcagggccga   9900
gggcagggag ggggccaagg cggccggctg gagggacggg gcccgaccgg gagcggagcc   9960
ggagcggaag ccgcagccgg gcggcgggag cggcgggagc ggcgggagcg ggggaagcag   10020
ggcgggccgg gctccatggc gccagcggcg tccgcctgag cagcgcgggc aacagcggcg   10080
gcgtcggccg gatcgggccg cgacacctcc tggccatggg ggacgtgctg tccacgcacc   10140
tggacgacgc ccggcgccag cacatcgcag gtgagggtcg cgccgcgcca cgcgcgccca   10200
ggggcctgcc ggaaccccg gaccacgccc ccgcccggc cagcagttgg cgccggggcc    10260
gggggctcgg gggagtcagg ccgggccggt gggagctgcc agggagcgtg ccccgcgtcc   10320
gagctcgttc cctctgagcc tgggcgcccc ttcccgcgct cttctgagcg ccacctttcc   10380
cggctcaagg ggactcggaa ctccttctct cccggaaccc cttcggagcc cgggcttggc   10440
ggaccccag cccacgaccc ctggccgagc tggggcaggg gtcgcagcct gctgcccacc    10500
cttggctgtc cccgcccaga agcgttgcaa gcccatccgc taccagcttt gggatctccc   10560
agacccagcc agctcgcgct caccttcctc cccagccgtc ccgtcccag ctccgccggg    10620
ccccagccct ggtacacgtg gcggaggctt cctgaaggac gcgcccatga aggcccggga   10680
ctgattctgg ggagtggggc cagggatcga tgggcgcccc cggaggcggt ggggttgcat   10740
gtcctttggc gcagacagca ggctgcccct gctagcagca ggggcccagg gaccggtcac   10800
cagagtgggg ggcctcagg gccagtcgcc agcccttca accctgttct tcagccaacc    10860
ctactctcag cctattactg cacagtggcc acttctccca gggacagctg tccccaaggc   10920
tcctggggaa gccggagctg cagaggggc ctggttcct tttcccccaca gactctggag     10980
aacagtgaga taggatgagg atctcggctg cctgagaaac tcctctctgg ccgatctctc   11040
ctggctggtg gagctgccct gggtggaatc ccagcatttg cttcccagac atctgtcctg   11100
tacaccttgg ttttctcctt tttgaaatgg ggtcagtgat ttcttcctta ttaatgagtt   11160
gttgggaggc ttacgtgaag taactcatgt ggcttgctta gcacagagcc tggcatagga   11220
gaggcacttg tatgtggggt gacggttcag gtgggtcgcc cctcgctgtc tagtgggccc   11280
tgagcaccgc gtccgcctgc acttattttt gtgtcctgta gaatttcacc accgtgttct   11340
```

```
ccacgctccc ttgagagcag gaagccctga gagcagtggc caggtgtcct ttaactccat    11400
gtctccaggg ccgcacccat gctgggcacc agggaggtgc tggggagatc tgccaagtga    11460
ctgtggtccc gggccaagtc ccaaggccag agtccctccc ttgtgccagg cctggggctg    11520
gctgggcaca ggggtgactg gggtgatgtg aaaatgaatc ggaccctctc tagcctctga    11580
ccagcgtggg gttaagtcct ggaaagcctc cttatccgac caggcctgga ctgtgggagg    11640
aggaagggcc agggcggagt cttcctgtcc cctccctgtc gcagcaagct cctgggctc    11700 tgtaacagtc cctccattca ggacctcctg ttgaggcccc tcgagggggcc tgggtggggt    11760 gtgccttgca ttcggtgggg ttttcctct ccccatactc agtgctgggc ctccctgtct    11820
tcccgtctcc tgggctgaga attgccagcc caccctctct cccctggcat gttacagggg    11880
aggggactga gaccacagaa ggtgaagtgt cctttactgg agagggttgg atttattttc    11940
tggataccag gctgggtgga agaaagttgt gcccactcag agcctgctgg tctctctctt    12000
ctccacactt cagtgctatt tataatcctc tttaaatgcc tcgaattcct ggtccagact    12060
cacctgaggg gagttcctga tgtgggggg tggggtgttg aaggggggca gcggggaagc    12120
ctcccagtct ccccagagga agtgagctgc ctttgaaatc tctgctggaa gggaatgagg    12180
gcgtgtattt gcctcctcca gtgatccagg caccctcctc accccaccca aggagcagta    12240
ggtactctca aagctggcaa ttaaaattcc agaaccctcc ctacctgagg ccttgttctc    12300
tgccccagta gaaatgtcag agttagagac atcccttccc acagtgctct gagttcccag    12360
gcctgttagg gttccaaggt ttgacctgca gctttgtgcc cgcccaagc aggtgagcag    12420 gtgaatgcca gcctgcctgc aagtcctggc aaaggtcaag cgtgctcccg ccacggtgc    12480 tgttttgctg ccacggcacc tttcatcctg ggatttcaaa gccctggca agcagaggct    12540 tgtttccaca ccaggagccc cacggggctg gtggcaggat gactcctgcc tccttacacg    12600
aggcagtgtg ccgtgaggaa gaatccctgg cctgggatct gggaggcctg aggatccttg    12660
ggtaggccac ttcctctccc tgggtctcag tttccctagt tgtgaaccga agtgggtggg    12720
ccactcgatg gctgaagtcc ctttcagctc tgagggccta acaatcccaa atttcccca    12780 caaatctccc ccagactgaa gccagctcaa ggtcccagta taatgcctgc aaccttggag    12840
taatatcttt ttttttttga gacaaggtct tgctctgtca cccaggctgg agtgcagtgg    12900
catcatcata gctaattgca gcctcgacct cctgggctca agtgatcctc ccacctcagc    12960
ctcccaagta gctgggacta caggcatgcg ccaccatgcc gtgctaattt gtgtgtgtgt    13020
gtgtgtgtgt gtgtgtgtgt gtgagagaga gagagagaga cagggtctcc ctatgttgcc    13080
caggttggtc ttgaactcct gggctcaacc aatcctcctt tgggagcctt ggcctcccaa    13140
agtgctagga ttacaggtgt gaacttcccg cccatgaact aacatctttt ttttttttt    13200 tttttttgag acagagtctc actctctgtc ccaggctgga gtccagtggc acaatctcag    13260
cccactgcaa cctccacctc ctgggttcaa gtgattctcc tgcttcagcc ctctgttaca    13320
ggtacacacc accatgcttg gctgattttg gtatttctag tagagacggg ggtttcacca    13380
tattggtcag gctggtctcg aactcctgac ctcaggtgat ccaccctcct cagcctccca    13440
aagtgccaag attataggcg tgagccacca cgcccagcca aaaataatag ctttattgag    13500
gcgtaattca cctaccatac aattcagcca cctaaagtgt acacttcagc ggtttttagt    13560
atattcacag aattgcgcaa ccattgccac catcaatgtt ggagcatttt catcagcccg    13620
gaaagaaatc ctctactcct tagtagtcgc tcctgtttcc tcctagtccc tcctaaatct    13680
aggcaaccac tgaacatttt gtctaattgc aaaagtaatg tgtgcacagg ccaggcgtgg    13740
```

```
tggctcacgc ctgtaatctc agcactttgg gaggctgagg agggcggatt gcttgagctg    13800
gggagttcaa gaccagcgtg ggcaacatgg caaagccccg tctctagtaa aaatacaaaa    13860
aattagccgg gcattgtcgt atgcgcctgt ggttccagct aattgggagg ctgagttgga    13920
aggattgcct gagcaaaagt aacacatgta caaacaattt aggagggtaa aataaaacat    13980
gaaaacaccc tccatctttc tccgttaaat cccacttccc agaagaagtc acttaagtgt    14040
ggtgtgtcac catttccaaa cctacctctc tctgtacatg ctcataatag cttggtttat    14100
aaaaacagat ttttttttt ttttttgagat ggcgtctcac tcaggctgga gtgcagtggc    14160
aagatctcag ctcactacaa cctccgcctc ccaggttcaa gcaattctcc tgcctcagcc    14220
tcctgagtag ctgggattac aggcgtgcac caccatgccc ggctaatttt ggtatttta    14280
gtagagacag ggtttcacca tgttggccag gctggtcttg aactcctgac ctcaggtgat    14340
ccacccacct cgacctccca agttctggg attacaggca tgagccacca cgcccaacct    14400
ataaaagag atattactct atgcttctgt ggtttgattt ttttcacttg gtaaattggt    14460
ggacatcttt ctgtgtcaga acacacaaga ctacctcatt cttttcttgg tgagttcgtt    14520
tctgtgcatg gatggtttgt ctacccagcc ctctgtgaat gggcatttgg gttgtttcca    14580
ctatttgct agtattcaca gtgctgcttg aacctgctgg tacaaaccct ctgtaatatt    14640
ccagtatcag agaggccctg aaatggaact cctgggtcac cttttttttt tttttttgat    14700
acagagtctc attttgttgc ccaggctaga gttcagtggc atgatctcgg ctcattgcaa    14760
cctccgcctc ctgggttcaa gcaattctcc tgtctcagcc tcctgagtag ctgggactac    14820
aggtgcccac caccacacct ggctaatttt tgtatcttta gtagagatgg ggttttacca    14880
tattggtcaa gttggtctcg aactcttgac ctcaggtgat acatctgcct cagcctgcca    14940
aattgctgag attataggcg tgagccacca tgccctgcct gggtcacctt ttgatagatg    15000
gacacatagc ctttaagaag gcagcaggcg tttgacactc tcctgctaag atggaccta    15060
gcattgagca ttttcatcct tttgacaacc agatatgaga agaagggtgt cttaattatt    15120
tattgagcaa acaaataat gcttctttcc aaagtgattt taaaaactta cctctctgct    15180
gggcgcggtg actcacgctt gtaattccag cgctttggga gacaggcagg cagatcacct    15240
gaggtcaaga gtttgagacc agcctggcaa acatgatgaa accacgtctc tactaaaaaa    15300
ttagccgggc ctggtggtgc gtgcctgtag tcccagctac ttgggaggct gcggcacaag    15360
aatcgcttga acccgggagg tggaggttgc agtgagacga gatcgcacca ttgcactcca    15420
gcctgggtga cagagtgaga ctctgtctca aaaaaaaaa aaatctacct ctcaacattt    15480
gggaagtggc tgtagatgcc aagagtgaag ggatggaggg gttccacctt ctgccacccc    15540
tcaccctgct gtgtggcttc ctctttgctc ccctggactt tgcagagaga ccaggctggc    15600
cggaagcagt gcctgggcct gggccgctgc ccttagccaa ggtccgggtc agccctggg    15660
ggcgaagtgt ctgggatga tgctgtctct ctgttgggtc ttatataaca tgcttttgtt    15720
ggctttgacc ctgccttccc ctccatccag cctcctctag tcccctgac tctgttcctt    15780
ttccactgct ggggcctgag tgccggcctc gcctactcag agctgctcca gcctcctcgg    15840
agcctctagt ccttcccaca cacgctgcca aagggacctt tctaaaccca cgcggggcca    15900
tggctgccct ccctgctgtc caaggagtga agcggaaaaa caggactagg aaccactcac    15960
ccgccgtcct gcgataacca cttcatcctc tgggagtact tcccatctgt gtcgatcatt    16020
acactttacc gggaccatga ctcaagtttg tgtcttgctt ctttcactac atgatctata    16080
```

```
gtaaacatct ctcccaggtc attaaaacct ccctggaagc atccccaaag gctgcatttt    16140
attccatttg aggacagagg gtcactttcc cagcttttc cctaatgctg acatgaggt     16200 tgtttctcac atgttggttt gtagggggcaa acagagccac tgtgtgtgtt tcttttctgg  16260
ctccagtcaa cttccctgtc gaagaccgat tcatctccca gcccaactct tcccgtgctc  16320
tgcttccgcc aacctgggca tttagaggga ggctccttcc tgccatctct gagcatcgtt  16380
cggggctagt gggcttgaag gggctgcctg tgtactgggg acgggactg atgaccatgg    16440 cctctgggtg tgtggccata gagtctagcc tgcggtgtgt aggaatggat atatattttc  16500
tgtctgaaga catggttgat agagcaggga ggggcagtaa tcaggctcgg agtgataact  16560
gtaaacatta gcaacggttt aactgagcac ttgctatgtg ccaagccttc ctttgtctgt  16620
atcatcttat tgaattccca cctcagtggc aggcctggat cggatagtcc aaggccttag  16680
ctatttaaac cacgttctgc tattagtatg tcatccgtgg tgcccagact gggcagggg    16740 acactgaaaa aggcctccaa gagaggtaag ctttcggagg cggggagagg aagtgggagg  16800
aggagccgag tgggaataga gcagcttgtg tcagtctccc tcccataggt tgcacaaatc  16860
tatcccaccc gtcattactc agtctgagac tcacagcctc tgaccagccc cattctccgt  16920
ccctgcgccc cctcctcct tccccgcggg cagagctcat gactcactgc accccgggct  16980
cctgcaagca tcatcctgcg gttgcagaaa ttcctgcact gcttttttcct tcccctgccc 17040 caccccatcc acttctgtgc tggaggaaga agggtattct gtagacgctg ctgggcagag  17100
gtttaaggaa ggagtccggg cagatgccta ggtttaaaac ccgtgagggt ggagcaaagc  17160
cattctcttc tcctggtaga atcttaggc ctgagtcatg gaagggtaca atcttttgat    17220
ctcaaaaatt ttaaaactgg aagaacagga agtgtccacc ccctgggact ggtcccattt  17280
ttttggagct gggctgcttc tggcccacga aggtgaaggg gcctgcctgg tgacgtggtg  17340
gatggtaagc ctgaagaagc agggagccca gaggttttgg ggtaaggctt tgcagtcaga  17400
ctgggtttga gtcctggctc tgccactgga tggactggtg ttcggggggca agttagtcaa  17460 cctgtctgag tcttagagcc ctccttacat gaggatgaga gttctggcat ctcaaggtat  17520
gaaggtcaag tccctggtc agcgcagaac agtgttggtg ggaggtgaca atatgtgagt    17580
ggtagctgtt atgattgtga ctttattgag ctaacttgac acccagggag atgtgtctgg  17640
tctgtctgtg gcctcgtgca tcccctgctc cctgccatgt gctccaggaa gttgacatga  17700
cccactcctt tcctaagcag ccctaaatat gagaatcttc ttcccttcca aggtcagagg  17760
agcaccagcc tatggccctg gacccctggg gtattcagcg agttcctgga ggacggtggg  17820
atggggctgt ggttccagca aggtcagtca ctccgcagca gcatccactc tgtgcctggc  17880
atttggcagt gcacagagga aaaggggttag aagatggatg ggaacatgct ccctccttgc  17940
ccacccatgt gtcaagaact agacttgtaa gccttaagcc tggtcccatt gaccacttgc  18000
tgtgtgactc tggacccaat ggccatgcct ctctgtgcct tttctccctg tctgtgacct  18060
caaggccagt atctactctt gggaattctc tgcctctgaa acccttttg tagggggtctc   18120 aagatgcctt ccaaaggcag ggctggtggc ttctatgtag aaatagaggt gcatgcctgt  18180
gagaccatca aggggtgtga tgagctctgg ccccaacac acgtagtcct tatttcttgt   18240
atgaattcaa tcaatagtta ttgaacacct tctgtgtgcc cggcgctgtg ctgggcacca  18300
gggacacgca gctacacaat cacatggtgt ctgcctgtgt gtgcttcctg gctggctgtc  18360
cctcctcagg gcaagcaatg ttcccaaagg gaaaggcctt ccttgggaag gtgtaaggga  18420
gactggcctg gggtggggcca gcctgctggg actcaggatg ggggaggtag agggaaacac  18480
```

```
aaaggctggt cttggcgagg aagggccttt gtccttaggg tcccagggag gccttggagg   18540
cattttcagg cagaagtggc accggtgggt cagctgtgag tgagtgtgga tgggaggagg   18600
tgaaccccat ggtgagaggg actggacctg cgtgtgtggg ggtcgggtgc aatgagggat   18660
atgtgtgtac agggtgggtg gcgtggccag gcctcagtga tggtgctgtg cagggctggg   18720
gcgagctgat gtacgtgact gttggctaca gggaaacctg tctggattct gtaggttgtt   18780
ttatcaaggc agaccttcaa ccactggtct tgcagcctct gctcccactc ctctagtgac   18840
aggaaactca gtcctttccc aggcaaccct gaaaatgaga accttcttcc cctccaaggg   18900
cagagtagaa agaggccggg agtcaggagga cctggtttga gatgctgtca ggactgccct   18960
gtcatttggc agctgccctc ccttctctgg acctcaaatt cctcatctgt aaagtggaca   19020
cagcagtatc ccaggcccct gaggctgttg tgcagggtcg gtgagatgat gtggccttag   19080
ctctttgtgc ttagggagca tcggctcctg gttcatccac tgttaccgtt ctatgtggtt   19140
cacataggac attggccaag ggaggccctc ctcttgcaga tcagaagtgc cgggtgtggg   19200
tcagggtgct gggtagaggg tccacgtgca ggggtggggg cccagggagt aactgggcat   19260
ccaggagggg aggaagaatg aactgtggtt tgcaaagtgc agaccccact ttcccacctg   19320
cccatctgtg gccaagccaa ctgcagctgc tgtccatctt tcccatgccc catgctgagc   19380
agaactattt gtgtccagcc gaatttgtga agcttagcac cttctagaag aggagtccct   19440
tgggaagaag ctgcccaccc actcgtgctc cagtcacctc tgatttattc cacctgccag   19500
gaaccactgg tgggtgcggg ctaggaggca ggctccccag gatgggtgcc tggaggcctc   19560
tgacaagccc ttccttttct ctgtgcctcc tcctcacttt gcctatctgt gcaacgggca   19620
tgcacttcca gctgtgaccc cttaggaacc tgtgggcctt aggctgcact gaaggcacag   19680
agcaggtgca gcacctccac attgcaggag gccatcttgc cgttgaagga agagcttgct   19740
ctgaaagctg tcctgttcct ggcctgagct gggaactggg gacaaagcag tgacatgagc   19800
cctgatctca tggaactcat gccagccaag aaggttccat caagctggat gtgctgtggc   19860
tcatgttaca aagcccgtgg atctttgttt cccagagtgt atgttggttt cagcactcag   19920
tcggcccatc tcaagaggca gcgtgtctgg cttgacctg gtggcagtat gcttctgtca   19980
ctgaaagctg tgtggccttc ggcacacagc tctcctcctt ggaggtccag ttgtcgctaa   20040
gatgggattg gtgctccctg cctttgggct gggtgaaggt tctgggaggt gcactgcgca   20100
gttcctggcc tgtgcagggt gctcagtaaa tggcaattgc gttttagctg aattcttagg   20160
gaagctgtgt gtccttgtcc cggcctgtca gagatttaag gggtgattca ggcatctaga   20220
ggaggaggga gctgacaatt gcacttctgt tttgcttttt gtttttgctt tttttgagag   20280
cagtattctc tgggaggcga agggtagaaa agagagctga gtttgagctt tggggtgggc   20340
aggcctgatg ggctggggaa ggtgtgtgcc tctcacccta ccacacctcc cctagccctg   20400
ccttgatttt tgaggtgctg atgagaagtg tctgcttttc ttttcaggc ccagaccctt   20460 cctcgtccta gttctggagg accccatgag ctcctctaac caatcccctc cttttctca   20520 tgccccagta aactgaggcc caggaagatg atgggacatg cctatgctct caggggcacc   20580
agagcttggc tggaacccag ggccttgacc ccagcatgaa gcttttccct ctccgacttc   20640
gtactcccac cccccgcacc cgtgcagggc cccagacggc aagggatggt gagggaagga   20700
atgattgggc cgggtggggc tgcagaactt ataattatga aaactgggta aacaaacaag   20760
ctctctggga gagaagcaag ccctgtgcgg gcctcacaga tgggcctgtg tccgaggaga   20820
```

```
cagcccaggc cgtctatgc gcagacagtg agggctgtg ttggacttaa aaagccaaag   20880
ccacactccc ctcccacccc cactcctata tttcaggctg ccaggaaaag aggagggga   20940 aggggcagcc ctttcttcca aggaggtagg ggctgacccc ctaggactct cctggggtca   21000
gccctcctgg cccagcttgg gacagtcaca gctcactgtg tgaccttggt caaggggcgt   21060
ctctcctctg ggcctcagtt ccccatctct agagtggagg tcaccccatc tctcaaggag   21120
ggtggcagga tggggaaaga tttgagccaa ctggttgaat acactgagcc ctttcactca   21180
ccctgacccg aggccaactg ggatctcaga aactcttcat ttctctctgg ccagaggcag   21240
gggcccctct tggagcagag gagtgacttt ctcagtgacc tgagagccgg cctggtcctg   21300
ggaggccaaa cctccaatcc tggcctgact ttagcaggct gcccagctca gctttcctgt   21360
cttcctgctg agattgtggc agaatccgag aggagctgtt tctggtgcct gccctgcagg   21420
ctgggggctg ggcagcttgc cctgcctgga ggccccggg tggagcctgg cagacttcct   21480
gtgcaattgg ggctgagccc ccgcctccc tccctcttc ctgcagtccc ctgtgtggct   21540
tctgggagtc cagctctgta gatgggaggc cggtcctgct tcagacctct gtggccttgg   21600
gtgaactcct gcctctcctc caagcctcag tttcccccat ggttcaatgg aggggttgga   21660
taagagcctc tggtagtaga gtgaccttgc tactaaccat gtgtcaccct ccttcagact   21720 gaccctttcca ggctgtcctg tgccctcgag gtcaagccca gaccctgaaa tgccctcaca   21780
gaccaagccc tgcagccagt agccccactc ctggtaggct ggatcaggct cttcctctga   21840
gctcccacag ccccttggcc acccgtgtgt acctgtagcc cttctcacat ggttgtgatt   21900 cattttttgtt tttgagacag ggtcttgcac tgttgcccag gctggagtgc agtattgcaa   21960
ttatagctta ctgcagcctc aacctcccgg gctccggcaa tccttctgcc tcagtctccc   22020
cagtagctgg gaccccaggt gtgcaccacc acatgggggca aatttatttt tatatttgt   22080 ataggcagag tctccctgtg ttacccaggc tggtctcaaa ctcctgagct aagccatcct   22140
cctgcctggc ctcccaaagt gctgggatta caggtgtttg agccaccacg cccagcccgt   22200
ggttgtgatt ctaattccca tctgtgatat gagtacctgc gggctaactc accatgggct   22260
cccctgaggt ggacaggtgg cctcacagct cagacttgct ccaccagcag ctgaacaagt   22320
accctaggtc aggctttatg ccttagtttc attggctgta aaatgggcat gatgatgctt   22380
ctactccact ggattgtaaa ggttattaaa ttatgtgtgt aaagcacaag aaatgctgag   22440
gagtcaataa ctgtaatgaa catttattag tgcaaattgt tttagttccc tagcaggaat   22500
gaatgaatga atgaatgaat gaatgaatga atgccattgc aaggtcctac atcctgggag   22560
catggggatc ccaaagctct ctggatgaag gtcctggtag gtgcagaatg tgtgtgtgtg   22620
tggttggtgg gggttggtta cagaggggca gggcagatgt gggagggggct tggggtggtg   22680 acgtacccccc tgcccttgtg aaggagtgg tttgggcccc tccgtgtctc agacccgcag   22740
gcacgaagcc atgtggccat ccacaacttc cttcctcctg cctgtattcc tcgaagcgtg   22800
actcactggc tttgagccct tcattcttgt ccttgagccc cgagggtgag gcgggtagag   22860
tctttcttgg aagggcggct ctctctctgg gttcctgtct attcctggcc cttctgcagc   22920
ttctgagcat gacaggcagg gatgaggggg tgcgggtagg gtggggtgga cacctgggcc   22980
ctggtcctgg tggccccact gacccccatgt gtgtcaggct tgggtgggc acccactgag   23040 ggcccaccca gggcttggat ctgagctggt gtggctgaaa cagcccagtc aagctcacct   23100
gggccctgcc cctgtagagc tcctgtctgg tcaggagaca cacagaacaa ctaccactca   23160
gtcattaatt aaaatcatta ccggagggcg aattgctata agaaatggc cactcttccc   23220
```

```
tgggagctca cgtgtcctgg gatctcccca gcagtgcctg tggtttgctc tcctgtcaca   23280
gaggaggaaa cacagcccac tgagtgggaa agggagcagg ctcagctctg ggcaagtcc    23340 tgtgcccacc tggggcctca ggatctcgtc acccatctta gaggtgtgct gttcacgtga   23400
ccctcctgcc ttggcctccc aaagtgctgg gattacagac gtgagctgcc gctcccact    23460 agggaatgct gttcaggagg cccagggtcc gccgctggcc ccccatggtt ctgggtgggc   23520
gggctggctt cggggtttta gcctggggac tgtggaactg cagcgagagc tgggtttgtt   23580
gtctttaaat ccctcctttg tgtgtcccta gacagaaacc actgtgacta aagtattggg   23640
atcttctaaa ggctaggcag gaaatggggg ctggtaaggg tggtcgtccc ccttcccact   23700
ccctccacca atacacagga cagcagaaag gtggcccaaa gccctgggag aaacccaccc   23760
caacatttca catctagaat gtaccgcgtt aggtaacaaa atggttacat tacagcatgg   23820
gggatggaat ggaaacaatg tattaacagg cattgttcaa tggcataata tgaagccatt   23880
aaaagtgatg attcagtttt gtatgtctga aagtgtgtat gtttgtatag gcatagaaca   23940
aaataaggaa agaaattcac caaaatataa atagaggtta ttttggagtg gtgggataat   24000
ggattatttt aatttttta ttctctcctg attttttgttt tttgttttttt gttttttttac   24060 agtgagtgga ttaaatcaaa agaataacc tgggtgggtg cagtggttca ggcctgtaat   24120
cccagcattt tggtggctca cgcctgtaat cccagcactt tgggaggctg aggtgggcag   24180
atcacctgag gtcaggagtt tgagaccagc ctggccaaca tggtgaaacc ccaccccc    24240 gtctctacta aaaatacaaa aattagccgg gcatggggt gcacacctgt ggtcccagct    24300
actcgagagg ctgaggcagg aggattgctt taacttggga ggctgagatt gcagtgagcc   24360
aagatcgtgc catagcactc cagcctgggt gacagagcaa gaccctgtct caaaaagcaa   24420 aaaaaaaaa aaaaaaaaa agaaaagaa aagaaaaga ataaccctat tgactgtatt       24480
tagtggaaca atttgattcc tgtctgactt cagaatctaa gccattctgg cccgactgga   24540
gccccaaggg ggttgcaagc acagggcagg ctccggagcg gggaagaggg aagagaaaat   24600
tctggaagag gggtgtttga gctcaatctt ggaggacagg agggatttt aaccagcaga    24660 cttggggtaa gggtgagtgg agggcatggc ctggcataga cccttgctta tccaaggcag   24720
ggagctgagc acagccttga gtgccaggca aaggggttgg ggaatggaga gtccttccca   24780
tgaacacttg ttagctggac tttagaatga ggactcagtt tctgtgatga gggcaaggag   24840
agcaacaaat ttgtgttagg taggctctgt ctgtgtgccc agcctctgag cccccagtgg   24900
ctgtgagcag ataggactgt ggtagtttag cccagagatg gcagatggat tccacaaata   24960
aagagtctct ctccgtgatg agtgctgaag gccgggcgtg ggtgggggca ttgggtggt    25020 gaggagtggt tgggtaccat ccaactggga aagcctatga cccatcagac ctccagtccg   25080
gaggtgtccc tgctaagtaa aaaaaaatta gccaggcatg gtggcacaag cctatagtcc   25140
cagctactct ggaggctgag gtgggaggat tgcttgagcc caggaggttg aggctgcaat   25200
tagctggatc atgctacggc tctccagcct gggcaactga gcaagatagg gctccaggcc   25260
agacagagct ccaggtcccc agggtaatat gcacaggatg ctggtacctg gcatagaact   25320
tgggtggcca gaagcatgcg ctgcacgagg ctgagcacga agaccccatt ctgctgtgtt   25380
tagggcttcc cttccgcctg tctccatgat gacctcagct ctctgctttc ccttacccat   25440
ctgtagcaca gggatggttg cagctacctt caagagggtt ttgtgagct tcatgccagg     25500 gccaccctg gtacctggca cacagcaaat actcaggaag agtttccgtc ctcggggttc    25560
```

```
agtccccagc cagggaactc cttccctcct ggaggagcct cagcagcctg aacttgatgg   25620
ccaggatggt attatatcag gttgcttggc ggtgagctct ggcctccccc tcagacccac   25680
tgtggctccc acctggcagc atctgccaaa ggtcaggttc tcacagctct ggaggtttgg   25740
cctttcaact ttgagcttcc ccagtcttcc ccctttattg ttttttcacct tttattatta   25800 ttgttacata agcaatagct agtggtcaaa gaaaattaga aaataacaga taagtaatag   25860
gaagaaaatg aaaatcaccg ataatcctac cacccagaaa agactttcag gcaccttcct   25920
gatacataat ttgttcttct accttaatag tgagtagtgg gcctcctcct tgtgaatgga   25980
tacagaatat tccattatgg ctgagcaagg aggctaatgc ctgtaatccc agcattttgg   26040
gaggctgaga caggcggatc acctgaggtc cggagttgga gaccagcctg gccaacatag   26100
tgaaaccctg tctctactta aaatacaaaa attagccagg cgtggtggtg gtggacacct   26160
gtaatctcag ctacttggga ggctgatgca ggagaattgc ttgaacccag gaggcagagg   26220
ttgcagtgag ctgagatcac accactatac tccagcctgg gtgacagagc aagactctgt   26280
ctcaaaaaaa aaaaaaaaa aaaaacgaat attccattac gcctcaatag tctatatttt   26340
aacttactca gtcaaagccc tattgccagg cagttaggct ttttctattt ttctttttttg   26400 tttgtttgtt tttgagatgg catcttgctc tgttgcccag gctgagggc agtgtcacca   26460 tcatggccaa ttgcagcctc aatctcctgg gctcaagcaa tcctcccacc tcaacctccc   26520
aagtagctgg gactacaggc ttgtgccacc atgcctggct aatttttaa aaaattttc   26580 gtagagatgg attctcactt tgtcatccag actggtctga aactcctggc cttaagtgat   26640
cctcctgcct cagcctccca aagtgctgcg attacaggca tgagccatgg tgtccggctc   26700
tattttttgt tgttgtaaac agtgctgtgt tggaaagctt aaatcaatta atgggattga   26760
gccattgatt ccgcatggtt tgagagccat ctctgctcag tgtcaggctg tgtgctggga   26820 ctggggtgc tgggtgggga ggcggccatg gtcctcaacc tcttggggac ccctgtctgg   26880
ggaagacagg cccagcatgg cacgccagca gaggtgggg tttagggcat ctttgggagc   26940
cagggagcag ccataaccca gacctggaga gtcatgggag gcccagctga ggacacctgc   27000
agctggtgac ctgagggtgg ggcaagccct gcacctgctg ctggctgagc tcatgggagg   27060
ggacctctca ggtgagccac aaaggataca ggaggagaga gtttcaggca gagggcaggt   27120
ctgcagaggc ccagagtaga cagagcatgg gcattgaggg aaccaaaact tcccagagat   27180
cggtgctgtg gttcttgcca gcctggcagc agctcccatg tgcatgacac tgtggtagtt   27240
ctttttcttt tcttttcttc tttctttttt tttaagatg gagttttgct cttgttgccc   27300
aggctggagt gcagtgacgt gatctcagct cactgcaacc tccgcctcct gggttctagc   27360
aattctcctg cctcagcctc caagtagctg agactacag gcatgtgcac cacgcctggc   27420
taattttgta tttattttatt tatttatatt ttatttatt tatttttgag acagagtctc   27480
gctctgttgc ccaggctgga gtgcagtggc gcaatctcta ctcactgcaa cctctgcctc   27540
ttgggttcaa gcgattctcg tgcctcagcc tcccaagtag ctgggattac aggtgcccac   27600
cactgtaccc agctaatttt tgtgttttta gtagagacgg ggtttcaccg tgttgcccag   27660
gccggtcttg aactcctgat ctcaggtgat ctgcccatct cagcctccca aagtgctggg   27720
attacaggtg tgagccacag caccctgcca attttgtatt tttagtagag acggggtttc   27780
actatgttgg ccaggctggt ctcgaactcc tgacctcagg tgatccaccc accttggcct   27840
cctaaagtgt tgggattaca gacatgagcc accgcaccta gccggtagtt ttttttcaaa   27900
gtgccgttcc atctgtccct ttgtgcggtg gggatcactg gcttcccttt tcttaatggg   27960
```

```
aacacagaag cagagtgacg tgcgtgcccc agggaagtgg ctggcggacc caggcctttc    28020
accggcccag cacacgggac aggggttga agtgcaggat ccgccagctc tggtttcccg    28080
gctctttgca ggtgctggat cacttgacag gatccaagca ggaagaggac gcggaggatc    28140
tgagcttagg tgaccgcctt agtttccatg aggaggtagt gacctttct gctgctgata    28200 tgtgaccttg gcctggccca gccccaaacc cagccctata tttgcaggaa gggtcctgcc    28260
tcttgggcca tactgggatt ggagaggccc tggtttatat ggaccttggg ggctgggaag    28320
tgtctgtccc caagctggag ttaacctttc tgggaatatg ccatcctcct ctggtgtctt    28380
aacatgactg ggagactgaa ctgcagagct ctggtctaat gtcacatagt caggggataa    28440
atatttctgt gcaaagtgct gtgctagatg ctgggcatat gttatgagtg agacagacag    28500
ggtccctgcc ctcctagggc aaatggagat ggaacaatga attattaaag caaagttgtg    28560
ctaatgacta cagggatct gacctgtgtg agcgagctgg caacagtcag ggacagtgct    28620
tttcagcacc ctaggctggc agttaggact caggtcagtt ctatcaaggc ttaatggtgg    28680
gctcctctgg gcttcccaat gtgtcaggaa ggagcgttgt ctcatgtccc aggtggaggg    28740
catcagggcg ttgagggtcc agcaccatgg tgtccagtcc cttcacgta cggggaggag    28800 acagggagcc aggaagggtg gggggcttgt ccagggtcac tcagcagcag tcaggtacat    28860
ggatttgggg cccagtgctc ttagccctgt atcaccaccc catttcactg gccagtgatg    28920
gggagacact gaggcggtcc ccactcaccc tcaagggact cccccgggga agcagaccaa    28980
gaccacagag gctgttggct gcgcagggtc tctcagggcg cacaaatggg gtcacgcagg    29040
cacctgggac agagagtggg aggctggcgg ggctgggagg ggagccgttc tcccacctcc    29100
ccttctggcc ccctctggag cctgaggaca cctgcagctg gtgacctgag ggtggggcaa    29160
gccctgcacc tgctgctcgc tgagcttaga gtacagacca agggagtctt gttatttgaa    29220
taaactttcc ttctatccat gtaaagggtc cctggcattc caatctggga ttgggtttcc    29280
tctggcccag cagcaagcac acgagtggat tttcatattg gctcatcttt cttgttctct    29340 tcttccccctt cttcccctcc ctggctttga gaaggcagaa tcgcccctcc ccagtcccac    29400
tcactgagag gaccctgcaa gccagaagct gcaggcagca gcatgcatgt gtgtgcacat    29460
gtgtaagtgt gcgtatgtgt gtgagtggat gcacggtgtg tgagtgtaca tgtgtgtggg    29520
catgcacatg tgtgaatgtg cgtgtgtgtg cctgcacatg tgagtgcatg cgtgtgggcg    29580
tgcatgtgag tgtgtgtgcg tgcatgtgca tgcacatgtg agtgcatgtg tgtggcatgc    29640
atgtgagtgt gagtgtgcat gcgtgtgggc atacacgtgt gtgtgaatgg tgggtgagca    29700
ggggtcacga ggcaacttgg gaagaacctg acttgggctt agggaaagga tattagcagt    29760
agagggtgct tggctgatga gatctgtggg gtttgtgtat ccgagtttag tccttttcca    29820
ttggggttgg gccatggtga ctggcactta ttagctgtta gttcttattg gaacagaagc    29880 tggcattttat tgggctcttc ctgggagtca ggcagggtga caggtgcatc tcacacatct    29940
tatttagtcc tcacaccaac tcttggaggt gggtgctctt tgaccctcca gcctctgctt    30000
acacacctcc agtgatgagg ccttccctac ccgccagggt cccttatcct gggcatctga    30060
ggccgttaga aagcccttgc tgggatcttg tgtgtcttct gtggatgact tgagaatggg    30120
ctctgcttgg caatagggcg tggctacggc tggacttccc cagcgtctgt tttccaggga    30180
actgtccaac tctaaggttt ggggagagga acaagtcctc cctcctttcc ctgagcagcc    30240
cctatgtggt acttagcccg tcacagcttc attcatcaca taccaagcaa gtctgaagct    30300
```

```
taatgttgaa accctagagg tattttcatt agcatcgatc tggatgtctt agtcaatgca    30360
ataagagaag agagaaaaaa agagaagtac aaatgcaaga cagcgggaaa gccctcatgg    30420
agttcaggga ctggtgacaa caaagcactg ttggtctttg acttctcca cccctaagg     30480 ctgcctacag gaagcagagt cttggagaga ccagaacttg cccagggcca cacgtgagtt    30540
ggcggcagag ctggacgagg actcagggcc cttgattttc caaccagca tctctggtga    30600 tggatgcagc agctaaggga gaggcggcaa ggccagagtg ttctccatgc cagtgtcaca    30660
gagcaggggg gctgtggtcg gtcgaggttc tcaggggtgc ggtacgtttg ggtgttggct    30720
ttcagaagtc ttcattgatg tttcttgctc cacttctcct tcctgatgaa ttaacctgag    30780
agatgagggt ccagaaagat tggaccccaa gcatgtcacc ttttaatctc atgacccacc    30840
agctgaggga ccagggaggt gctgttccag tcacccttg ctggttccca ttgcgtggcg     30900
tgaaacatgg gacagagaac tgccatgagc actgatgaga gatgccactg ggcaccctga    30960
ccatttatgt cctggccacc aatactggga cagatggagc tccttcgaga ggttccatca    31020
ctgccattga taacaccagc ccacatttgc ccaggctctg tgggtttatt catttcattg    31080
aatccttatg acaccttgca agatggggga tcgtaaagtt gctgggtttt ttttgtttgt    31140
ttttttgttt ttgaggtgga gtttcgctct tgttgcccag gctggagtgc aatggtgcga    31200
tctctgctca ctgcaacctc cacctctagg gttcaagcga ttctcctgcc tcagcctcct    31260
gagtagctag gattacaggc atgcgccacc acacctggct acttttgtat atttagtaga    31320
ggcagggttt ctccatgttg gtcaggttgg tctcgaactc ccgacctcag atgatctgcc    31380
caccttggcc tcccaaagtg ctgggattac aggcgtgagc caccgtgccc ggtggtgctg    31440 tttttttgttg ttgttgttgt tgttgtgttt tttgagatgg agtctcgctc tgtagcccag    31500
gctggagtgc agtggcgcga tctcagctca ctgcaacctc cacttcctag gttcaagcga    31560
ttctcctgcc tcaaccttcc gagcagttgg gattataggc atgcgccacc atgcctagct    31620
aatttttgta ttttttagtag agacggtgtt tcaccatgtt ggccaggctg gtctcaaact    31680
cctgacctta ggtgacctcc caaagtgctg ggattatagg cgtgagccac cgcacctggc    31740
caggttgctg ttactcccat gttacagctg aggaaacaga ggttcagaga gaattgagcc    31800
atgtgttgct gaaagtccta tagccagcaa agggtggagt taggatttga actgagatct    31860
ggttccagga ccttgacact gcactgttga agggtccttc ttgacctagg acgtgctgat    31920
aaatctttgt ggaatggatt aactctttca tgcctgtccg aatcttggcc tttctcgggt    31980
cttctgcttg gcacacactc ccttcccggt gtcctccctc ccctagcagg gactctttgt    32040
gtctcagctg ctacctccct ctgggaggct tccgtgaccc tgcaggcttg gtcagtcacc    32100
ttcctgggct cctgtgacct cctgtgcttc tcccagttgg ggctcctagt aattgtagtt    32160
tttgttgaca atctgcctcc ctcattaggg tactctctcc tgagtaccca gtggccagga    32220
ttgctgaatg aatgagtgag agcaacataa acccttcctt ggccatcgtg atgaagcctc    32280
agagcctcgc ctgaacttgg tgactcgcct gacatctgcc atttttggctt ggcccgcgct    32340 ggctgatgga ggacatggga tctgggctgg gtcctgtcct cagccctgcc ccagtggttg    32400
tgacctgtct gatggggcgg ggctgagtgg ttgacactgc ggacatcttg ggggaagggc    32460
ttgaccacag gctcttcctg catatctcaa ggtccaacac caggctggac gctgagggga    32520
acattggtgg tgggttctca ggcccagggc aggtgtccag gcccgtgggg ggcacctgcc    32580
aatgtgcacg agccacagca gagcaccctg ggttcccagt ccagcctcgg ccctggacgt    32640
gactgagaga agggtatga ggagcacctg tggacaggcg tggggatgct cctctgggc      32700
```

```
ctgggcagtt ttgacaggtg gctggctaag gctcaggctc ctgtgggggt ggtgaggatg   32760
acaagaaagg aatgaaggcc agagacattg tggagaaaaa gtcaacagga aagggtgact   32820
ccatgtgaga ggaaaggagg gtcgtgtcta cacaatcact gtcatagatc agcctcctcc   32880
ttgggcgtgg ccttggccag ggggccgcag gatggcagcc ttgggtgccc accccctgga   32940
gtgtgggtcc tgctctgggt ggtgacgctg ctgggggcct cggcaccccc tgggctgccc   33000
tcccagcgag gatctgtgtt cccagacggc aggcatgcct catcctgggc tcccagaaca   33060
agctgccact gtgggctgtg ggctggggcc gctgccaggc aggcggggtg ggggcagga    33120 ggggatgaga gggcttttgt ttccttctgt ttgtgtcaag atgggaatgg acttcctccc   33180
accaggcggc ctcgaggtgt aaaggaaagg gcagcccag tgggcgggtt ttgggtcacc    33240 cgttttttg ggtgcatttc tctgggctcc cgcctcagcc ccgccctctc ctcccagccc    33300
tcctgcctca aagctcaccc ttccccacca gacctgttgt ggcccagccc tggttaaata   33360
tttgccaacc gagaagagtt ttcaaggcag ccttgtgaaa acccccagct gactcctggc   33420
tctgttgggc ctgacctgcc tctgtgatga gacccagacg gcctgtgccc tcagactgag   33480
tccctgccca ccatggcctc cctggtgacc tgtttggcgc ctgaggctgg gtgacctaac   33540
acttgttcgg cacttgttta tcaagcaccc ccctgggcct ggcgggagct gggtgctggg   33600
gagacagcgg agagcagtct cagtccgggg agcgtctcag atgaggcatt aactgtggtt   33660
gaggggagtg ccggggagca ggccaggggc tgtgggagtg gaggccaggg aggctgtgga   33720
gacctgggag gccgggactt gtctggaggg agggttccga ggaggtggca cttgagcctg   33780
gggaggagaa agaggagttg gccaggcaca aggggtggac gctaggaggg cactgtagac   33840
gtgggacccc aaggccagag gccagatttc ctccgctgag gaggaagctg aggggctgag   33900
gttgcggttc gcttgggttc gctgggtgtg aaagccccat tcacctgttt ctccccaaga   33960
tggtctcaga ggagctggga cactaacagg gcaatgggac cctgggcagc ttttccccat   34020
ttccccagcc tcagtttccc catctgtcca aaagatagtt tggacttgat cttggaggtc   34080
ccttcccagg tccagtggcc tcttaggagt atgtggctgg cccatgaatg agggaatgtg   34140
ccatggcagg gattctacca gcaccaaagg ccaagataac agccatggcc gggtgcggtg   34200
gctcatgcct gtaatcctag cacttcggga ggccgaggcg ggtggatcac ctgaggtcag   34260
gaattcgaga ccagcctgac caacgtggtg aaacccgtc tctactaaaa atacaaaaat    34320
cagctgggtg tggtggcaca tgcctgtaat cccagctgct gggaggctg aggcaggaga    34380 attgtttgaa cctgggaggc ggagattgca gcgagctgag atcatgccac tgcactccag   34440
cctgggcaac agagtgggga ctccatctca aaaaaaaat taattaatta attaaaaaa     34500 taaaagaaaa aagaataac agccatgtgc ccttataggg ttcatgcagc cctatcctgg    34560
tgttagcaac aaaagccaac atctcctgag tgctccctgc cctagcaacc ttgtgaggtg   34620
gtggtggagg actatgacat tatacccatt ttacagataa ggaaactgag gcccagagag   34680
gctgttctga gctcagggtt tgcttcttgt tttaagcatg gctccagaaa tacccgtctc   34740
tgtgagaaac ccaccctcct ctcccaaggc cagcgccatg ttaggtacca gggatacgga   34800
agtgaacaag ataccattcc aacctgggaa gctgccagtc gagcaaggaa tgtcccagca   34860
gagagtcagc aaatggttct agctcttctc tcttccagca cagtttgagc agcgaacaga   34920
agcaggcttg ccttcacatc ccagttttgc tcttccctgt gtagtatcgg gaaagtcact   34980
taacttctca ggagcctcag atcccttatc cataaagtgg gtttggcagt acgtcccagt   35040
```

```
gagggttaaa tgaaacaatg ttgactataa tttttagcat atatgggatc tgcctctgtg    35100
cctggcacag aactaactgt tacatgcatt agctcatgtt gcaattatga ttataatttt    35160
ctgcaagtgg ggaactgaag aacagtgtga tggaggagag gatgggtgag cagggccttg    35220
aaagtctggc taagattgtg aactgtggaa ttgaagggaa gggcggtcca gccagaggac    35280
acaacatgga tgaagatgtg gaggtaggaa atgtgtaatg gaggcgagag acgcccaggg    35340
tgtggggatg ggaaggagag cggggctgag gttgcggatc ttggatgtga ttctgtgtaa    35400
catgcttgtg ggcttcagtg tgccaggcct gtggtgacaa gttagtccat agtctcttgg    35460
ggccatcaga gcccagagag atcctttaca aagtgcttca tgcaaccatc ttccagatgt    35520
ttccacagcc cgtggagtct aggttcagcc agcctgggct cacacccag cttggatttt      35580 ggctccctgc ttgacagccg gctgacctgg gacaaggccc tggaccttcc agcctctgtc    35640
ttgatcgggg gtgattcctg taccacttcc tgcagctgtt gtccgggtct atgtcagatg    35700
gcgtgaggtg tccccagcca gcgtgacacc cattagcttc ggggtaggag ggctccctaa    35760
ctgttctgtg cctttttgtt cctggtgtgg agacagagcc tttctccctg ggccattttg    35820
agagtcgaga atgatctcgc actggaagtc cctagctgag ggctggctca cgcagggtca    35880
cacggctgtc attgtcgggc cttggcgtgc tgagggatgc tgtctttaag ggaagaggtt    35940
tttccttgtt aataactggc cttggggcca ggcacagtgg ctcacgcctg taaccccagc    36000
actttgggag gctgaggcgg gtggatcacc tgaggtcagg agttcgaggc cagcctggcc    36060
aacatggtga acccccatc tctactaaaa atacaaaaaa ttagccaggt gtgatggtgg     36120
gtgcctgtaa tcccagctac tggggaggct gaggcagaag aattgcttga atctgggagg    36180
cagaggttgc agtgagccaa gatcgtgcca ctgcactcca gcctgggcaa cagagccaga    36240
ctccgtctca aaacaaaaca aaacaaaact ggcctcaggg aagagtgacg cagccaaggg    36300 cccccttcagg gcacctgagg ccagcagggg gggaaatgtc ggtggcagcc accttcccaa    36360
ggaaggacag cacagtgtac atttcctcat ccccaggacc cagccaaggg cctgctccga    36420
tgtcagcctc cgtttccgtg gtgaggaatc tccggggtgt gtgggggctt attgctcagt    36480
ggcttcgtgg ctctcttttg ggggtgggtc tggcctgaga ttggcacttc tggcctgttg    36540
ctgtgggctt cccttccttt tccactgcgt gccaggccct gccccaggag cagggtgct    36600 gcctgtggga gccacatgag gaacagacct ttacccacca ggaggccagc ggtgggctgc    36660
gggaataggt ggagggctcc cacccagcct ggggctttcc agttgaaaga cgcatggtgg    36720
tgggctgagg agtgagcttg gcggaagact gtattccgga catggggagc agcctctgcg    36780
agaccccaga tgacttgggc ctgcgggcat ggtaaggagc tcagttccat cccagaggca    36840
gtaggagctg taccactgga aggtttctga gccaggaaac gttgggcaac tcccctgtgg    36900
cccctgtgtg tgggaaggat cagaggcagc caggatggag taggcaggac ttcagtggct    36960
gcggcgggca caggacggga gtggcctggc tgggggggcag tgactagagg cacaggctgg    37020
gtggccactt gactggcccc tgggtgctgg ggagcctgcc tcaccctgtt gggcttgtgc    37080 taggggcag gtagtggtgg ggtgggaatc ccataggccc tgtttctctc aggcccagaa     37140
ggggggtccc agggggtctgc tgttgtaccc cttctgccaa ggatggctca tggagggacc    37200
ctgaatccgt cccttgcctt ctctggtatg gtccctcttc tggacaggaa ttgattgggt    37260
gggggacact cagctgtcct cctccttcct ggcctgccag attctggctg ctggctcagg    37320
ctcttctcgt ggatgggctg ctggtccccc tcctgctact tgatggagcc tgtcattacc    37380
cctcccaccc ccaacttccc acctgattac aggtcctgag caggagccct gtgtctgccc    37440
```

```
ttcccgtgga ggccacccac aggctggtgc tgcggaggcc agggtgagat ggttttgccc   37500
aaacgttggt tccctgttca gagttcatgt catttacaag ctgtgtgtcc ctggagaagt   37560
cccttaacct ctctgagcct cagtgttctc tgggaagtga ggacagtgcg tgaaataatg   37620
agtgtgcatg tgcagtgccg tgctgggcac agaggtggtg ctgacaagtg gctgctgcta   37680
ttgtgtgtcg attgtgacag taggtggggg gcaagtagaa agtagaaagg ccctgagcga   37740
ggcactggtc tatgccaacc cagctctgtt ggatgtgctg tgtggcccta ggagagtgtc   37800
accacctttc tggaccccaa gctctccctg ctgtctcagg cacatgatgg agatggtggt   37860
gcttgggaca actctgagac ctgcgagaat ggagtccctg ccccgactct gcctctgctg   37920
gtccctggac tgtagggtgg gtggggtcgg cacccccctc tttcccccac ctccccatgc   37980
tggacctgct ccctatgccc tgggaaccag gcgggcaggt tctgagcctg ccccacccta   38040
cagggtgctg ctacctgcct ggtttcagtc ggcaaacctc tcagccctga aaccctgaaa   38100
ccgggctggg cctcgtgggt gaggtgtgtc cctggagccc actggagaga ccggatgagc   38160
caggaacggg tctggcacag cgccctccac tggggccaaa ccagggctgg cgccggcgtg   38220
cagcccccat ggtggacatg agctggatgt ggtcgcagct ggagatgact ctcttcctct   38280
tgggtccccc gtccgtgtgg aacagggttt caggcttagg catcaggtcg ggaccagggt   38340
gcagatccta cctctgcctc ttctcagcag agtgatttgg cagaggtacc cagttctcgg   38400
tcacctggtc tgaaatgttc tgccagtacc aataccacct ggcccgaggt tgagttgaag   38460 aatcggggggc acgtgtccaa gcaaaatgct tagcacagga gcggcacatg gtggctttgg   38520
ggagcgtcat gacaaggcaa agaaggaact ccttagcttg gcattcgagg ccctccggga   38580
tacgcctttt taggtccatt ttctgagaac ccctggactc cttcctccat tctcagctca   38640
gcaagcctcc tctcctctct gagcctcagt tcccctatct gcacagtggg cctggtaccc   38700
catcccccag ctccccaagc ctccaggcca ccctggggcc tccccagttc ttgcccagcc   38760
tcactatctg cacaggaagt agcgtggccc ttaacgttgt cagtttggaa aatcagagat   38820
taattaacgt tccggccgcc ttggctgctg ttggagctgg tcccagggtg gccaggctg   38880 catgctcagc ctctgtttca agggcctcac tgtgggttag aggaaccttg acaagaggca   38940
cttcttagga gcccccattg gtgaagtgcc cccttcttgc cagggtaaag ggcttcatgc   39000
tcagtagccc gtttgtctca taacccattc aggcagatac tgttgtgcca ttttgcagag   39060
gggaaaataa aggctcagag aggagaagtg ccttagccaa ggccacacag ctcataggtg   39120
gcagagctgg gacttggacc cagagcctgt gtgtccatgt agaaatggtg ccctgtttgc   39180
aggtgatggg gggtgcctag ttctcccccc gggtcctttt gtctggcccg agggggctgt   39240
gatcagctgc tggtcagagc tgactcacca gcagctcaca ggaggggctg aggccagcat   39300
cccggtcagt tcctggggcc agggcagcac tgattagatt gtcgttgaga ttttcggtca   39360
gctgagctga cagggaccca ccctcccatt ttaaaggtgg gaaaattagg gcccagtgag   39420
gatgaagaag taaggctcca gtgggtcgga tgattctcca ccagctccga cccgacaggg   39480
gccagtggag ctgaaacccc tagacctcag tcccggctct gacacctgcc agctgttgcc   39540
tcgggaaagt cactttgccc tctgagcctc ggtttcctcg tctgtaagat gaggatagta   39600
aagccttgtg ttgcctcatt cttgggattg gcaagaccc cagcaagaga gtggaaaacc   39660
aggggtttga aagcggcatt gcgggtcctc gtgaggggtc actgggatga gaggcttgc   39720 gggggtagggc tctgtgcagg ctttggtggg agacaaggtc caaaacccac ctctttcccc   39780
```

```
tccgttgtgt gtctttgagt gagtcagtga gtctctctga gcctcacttt tcttcctttc   39840
ttttttttg actgacccaa attagatctt tattgtattt ttccacatat ctatcattcc    39900
caaaagatca gtcagctcga tccttaattt ttcttactat gagatgtccc taatacacag   39960
tctttgtata aattatccat tttaagtata tagtgaattc cagatgtgat cacaactgca   40020
tttcttcctt tttttttttt tttttgagat ggagtctcac tgtgtctccc aggctagagt   40080
acgatggcgc aatctcagct cactgcagcc tccatctccc aggttcaagc aattatcctg   40140
cctcagtctc ccaagtagct gggattacag gcgcccacca ccatgcctgg ctaattttg    40200
tatttttggt agagatgggg tttcaccatg ttggccaggc tggtctcaaa ctcctgacct   40260
caagtgatct gcctgcctcg gcctcccaaa gtgctgggat tacaggcgtg agccactgtg   40320
cccggccgca caactgcatt tctttttttt ttttttttc tttgagatgg agtctcactg    40380
tgtctcccag gttggaatgc agtggcgcga tcttggctca cagcaacctc tgcctctcag   40440
attgaagtga ttctcctgcc tcagcctcct gagtagctgg gattgcaggc acgcatcacc   40500
atgcctggcc acacaactgc gtttctaaat agccatgtga cactcactga gtgcttcctg   40560
ggtggcagcc gctgtgttta gcctgagtct cacttttctt atctgtcaga tgggatacta   40620
atacctgtta ggattaaaca ggctgtggag catgcagtaa gttgtcggtg ataggcacc    40680
tatccctggc aaactctggg gatccagggg cagagttagg aggactggct tgtgaggggg   40740
tccttctcag tcaccctcaa taacccgata ggatgcagcc cttggagaca gggttccagt   40800
catatgggga gcagagcccc cctgagatcc acagagcacc cccttattca accaacttgc   40860
tgaaagggtt ggctctcagc tccacaacaa acccacaagt gtgtgttgtg agttttgccc   40920
tggacctgca tccccaaaag tggcctcttc agaggtggat gcagcccagt acccatagag   40980
acaccaggtg gagacagagg cctgggatgg gagtggcttc ctgaggtccc tgggcacaga   41040
tcaggactca actccactcc cagaattcac acactgccct cttgggctaa aagggaacc    41100
gggacccaa caggcaggcg ccttttgtga caacctctgt gaggggcctc ggcaggtttt   41160
gtggactgac agagtggcct ttcctgagct gtttaattgt tctgagcctc ggttcataca   41220
gctgtaaagt gagggttgta tttccctctg ggccatttga agaatggtgt gtgttggggc   41280
aaagaacagg tgggccctgt gtctgatggg cgtgggctta cctcctgctg gcagaaagcg   41340
aaaaggggc aaccaacggc tctgggcgcc agcagaggct aagggttatg ccaggggatc    41400
ccagccacgg ttaggcagga cccccatca aacgcaggga cctgctgtcc cccttggctt    41460
ccccgcatct gtgatctttg tttgtggaag gcctcccatc attatcatta ttatttgtg    41520
attcttgtcc cggttcttca gaaaacaaat ctttattgga ttatttcaaa ctataaagt    41580
tatactgcta ataaacattt caaacagtct cttatgactg ctgttctcag ctgaggacac   41640
tgatgattaa cagtgacgtt tatggaggcc tggagctgag cacctcaaac gctatccggt   41700
cctgcagagc tcagagctcg ggaacagctt cggagaggcc catttacaaa tgaagaatgt   41760
gagtctctga gagctaggcg cttgcaggc tggcatatgg cagggcgggg actctggtcc    41820
tgacttcaag ctcctcacca ggaggctggg cacctgggc cgcagggcag gctctgtgag    41880
tcctgcccca ctccattccc tgccttctca cctagcagca cctggggcag agtcaatgca   41940
gggaggcaga atggatgaga taatgtggaa agtgacgaag ctggcacaca ccttcacacc   42000
accccacccc agcctctctg tagctcacag aagcgagtga tttctaccac cagctggagc   42060
cccccagttc ctgggcccag gacctgcggg ccagccctgc ctctgtagat gggggcacag   42120
ccagtttcct ctctgcccte taaggggagg taggggggcct gtggggccct gtagacaatg   42180
```

```
gccagagcta ggaccaggag ggtggcatgc agccgactat ggctcgaacc taattgcctc    42240
catctggctg tgtgacctca gctgagctgc tcaccctctc tggctcacat tcccctaaca    42300
gggtggtaag cctgagtgtt ggaggccctg tccaacatct gccccaaatc cgtggcgtgt    42360
ggtgtctcca gaggctgcgg caggaaatgg aaagagctgc tgtgggcaag tatggaggaa    42420 agagggtgc ccgggctcag gacccccaca gacacccagg ccgggacgcc atgtgggaat    42480
ttgagttgta aaatcctgaa gcaacaatgc cggggagag ccactgcagg gagcaagaag    42540
gaaaagtggg gtactgggtg gggcctgcct ggactgcagc cccagagctc agcaggtaag    42600
gcggtggcca ggctgggtcc tctggctgag cccccaccag ggctgcagtg ctcgcctggg    42660
tcctcttcca gcagggtcca gccaggaagg ccctgcaagc cctttgtcca ggctggcccc    42720
ctcccaatgc tgctggcctt ttgggtccct ctggcctcca cacctgggt ccccagcacc    42780 cgagtcctca tcttctgcgt ctctgggtta cttcctctgt acaaagcacg tggcggttcc    42840
ttccatgctg gctgaggaca tctctcaaga atgtgctcgg ggctaccct gccaaggagc    42900 catccgtggc cctgtttccc atggtcctcc ctttctagct ctcccgtggt cgccacccTT    42960
cttctgagcg gagctggctt cccggtgctg cctgggctcc gtccttaagg tccttaaccc    43020
cttgctaatg ctgtccccct acctgcagca tggcgctccc tcagtacccc ctccgatgcc    43080
tgccccacgg ccttcccttg tttggactta gtaactattt ggctgctgga ccaaacccc    43140 actattcctc cccttgccga catctgcttg tgccaggcct ggtgcccagg atccagtggt    43200
gagcaaaagg agaccagacc cctccagcag agttcctggc cctccctacc tgacccattt    43260
ggctcctgaa ttctgagagc aagcctggat agtgagcgac tccagcccca cctggggcca    43320
acgtgacaaa cctagaggga actgcatcct ggacccctgg cccttgcctg gtcccctca    43380 gcccgaggcc ctaggcctgt gggcagcact gcgctggtcc agggacctga ccttcagcct    43440
tgaccttcag ctcccaccct gacaggcagc ggggtccctg cactcccatg tctcccttcc    43500
tcagagcttc ctgcagcttc ctctccagtc cacagcctgc ccaacttggg ccttaactgt    43560
ccctcggtgg gacatgcctg ggccttctcc tggctcagtc ttgccctctt ttgtcctccc    43620
cagcccagcc caggggcctt tctgaaccca gctcctccct gcctggacac catatctgga    43680
ctgtgctgtc cggcagttga gcacgggct gcggtcaggc agacctgtgt tcgagtcctc    43740
acagcaatgg cagctccctc cagggcctgc tccgtgaggg ccagggtggc agactccagc    43800
cctttgggat ctgtctgtgg gctgggtgca ctggggctgg ctgggggccc tggagccacg    43860
gccaaaggaa ccctgagacc tgcaggccca agcctgccca tcctgccgac cacgttgata    43920
gaatgcctgt ggggtgcgtg gcttgactcc tcatccctga aataggaaaa caacagcact    43980
ggcttcctgg ggttctcatg gagattctct gggttcacat acgtaaaacc tgccgtagca    44040
cgggtttaat gctctgcaag tggtggccat gacgatgaca accatggtac cgatgttatt    44100
gtcagcttcc atcctctttt ctctattatc cccgatgtat gactctcttc catttgcccc    44160
ctctctgcct catgattttt caaaacaatt cccatggtct cagagagagt tctggttgtt    44220
tatggttttt aaaaaatagg cattcaaagc aaattcctca tttgttctcc ccttcctccc    44280
cccaaactgg aatctggaca gacatgacct cactccagga aaggggagta cagggaggga    44340
cagggtctgt ggagaggggt tgggggggcat ccctccaccc ccatcactga ggcagggccc    44400
ggggtgtggg cagacaccca ggaaggtcac atgcctggga ccctggttat gagctgtgag    44460
gcatggtgtg tgacatgccc tttcagccct cctcccaggc caccacctcc tggtggggac    44520
```

```
ccaggactgc atcccagctc taccacccac tggctgtgtg accttatgcc agtgacttaa   44580
cctccctggg cctcagttac ctcctctgta aagtggggat aacacaggtt ctccctcaca   44640
gaactataga gaggatggaa tgaaatgtca tcctagccag gtgccctcgg tacctggaga   44700
ctggccatgg gaggggcagg ttcctgccag ctcctgtttt gagaaaggac caggtctttg   44760
aaacctggaa tccaagactg tcagagatgg cagggcctgt ccgtcatcga atgcagcctc   44820
tcagtgcatg gggaaaccg aggctcagag aggggagccg cacagcgggc cagcacaaat   44880
cccagttggg acgcgagctg cagcttctta ggaccaggaa gcctctcccc tcatgggtcc   44940
gagaccctct ctgggcctcc tccttcatct gaacatgggg gcacccagga gcacacgtgc   45000
tgagcctgat gtggcctggg cctgccttca aggccatagc actcacctct attcagaaac   45060
cgcgcagaag acagaagcaa atggccagtg aaagcagaaa ggttgttcac ttggtagagg   45120
cattaatttt agaatgttta ttttttatta tgaaaggaat catgattata aataattca    45180 aatgctataa aaggaaataa accaaaaatg aagttcactc tgtactcccc actcccacac   45240
cagaggtcct gccttcctag cctggcatgc tgccttccag acctcctcca cgcacccaag   45300
cctaagtaag ctatatgcac aaataggagg agttttggtt ttgttatgtg tgtgttgaga   45360
cagggtctcg ctctgtcgcc caggctggag tgcagttgca cgatcatagc tcgctgcagc   45420
ctcgacctcc ctgggcttaa gtgaccctcc cacctcagcc tcctgaatag ctgggaatac   45480
aggcacacgc caccacacct ggctaatttt tgttttgttt tgttttgttt tttgagatgg   45540
agtctcgctc tgtcgcccag gctggagtgc agtggcacga tctcggctca ctgcaagctc   45600
cgcctcccgg gttcatgcca ttctcctgcc tcagcctccc gagtagctgg gactacaggc   45660
gcccgccacc atgcctggct aattttttct atttttagt agatacaggg tttcaccgtg    45720
ttagccaggg tggtctctat ctcctgacct tgtgatctgc ccacctcggc ctcccaaagt   45780
gctgggatta caggcctaag ccaccgtgcc cagccttttg ttttgttttt ttaagataga   45840
gtcttgctct gtcacccagg atggggtgta gtggtacgat cttggttcat tgcaacctct   45900
gcctcctggg ttcaagtgat tctcctgtct cagcctcctg agtagccggg attacaggta   45960
cccgccacca tgcctggcta attttttat ttttagtaga gatgggggttt tgccatgttg    46020 gccaggctgg tctcgaactc ctgacctcag gtgatctgtc taccttgtcc tcccaaagtg   46080
ctgtgaacca ccgcacctgg ccagactttt gtattttttt gtagggatga ggtcttgctg   46140
tgttgctcag gctggtctca aactcctggg ctcaagcgat ccacctgcct tagtctccca   46200
aagtgctggg attataggtg tgagccactg cacctggcca gaaagcgatt tttttttt    46260 taaatgagct gatagtcaac aggtgactct gtcacttgct ttctttcctt aatggagcat   46320 gagcccttc cgtttgttgg cacctatccg gataggtccc tccatttttt taaattttt     46380 tattatatgg agtctcgctc tgtcgcccag gctggagtgc agtggtgcaa tctcgactca   46440
ctgaaacctc cgccttccac caaacttcca ggttcaagtg attctcctgc ctcagtctcc   46500
tgagtagctg gccttacagg cgcctgccac catgccctgc tgattttgt atttttagta    46560 gagacaggat ttcgccatgt tggccacatt gggcttgaac tcctgacctc aggtgatcca   46620
cctaccttgg ccttgaaaag ttctgggagc accatgcct ggcccccctc catcttttta    46680 cttttactg acctgggtga atgaaccaat gtataccgat catccctaga gatcacattc    46740
agctgctccc cgctatggcc tcagtgcaca ttcgcctttg tgtcctgcga atcgttctat   46800
gggggtagat tcctagaggt gggagcatcc aaggacagga cacccaccct ccgaaatggc   46860
tgtccccatt cctggcgccc ccagctctga gtgacatggc ctgttttgc atgtccccac    46920
```

```
cagtgtgacg acaggaaatg gagtcttggt tctgtttgca tttgtttgat tctctgtcta   46980
tggccattac ccgctttccc atctggaggt tcacctttc caaggcagtt ggttttcaca    47040
ggaaacgcgg ggctctggcc agaaatgcag cgcagatgag cgcgaggagc ctgtgcaaac   47100
aattccacat gcaggaattt ggggctttgc agccactcct gcctagggga aggatcgtga   47160
tgcatcagca tccctgagga cctcaagctc ctgcttgtcc ttctcttcca gaaaaaaccg   47220
ggaagatcct gacggagttc ctccagttct atgaagacca gtatggcgtg gctctcttca   47280
acagcatgcg ccatgagatt gagggcacgg ggctgccgca ggcccagctg ctctggcgca   47340
aggtgagagg tgctgggagg gctcgggtat gttctgctac ttctcgccat gtggcctcgg   47400
gggagtgacc ttactttttct gggcctcagt ttcccattgt tactgtgatg gcctctaagg   47460
gtctccccag cttctttttt taaaattaat tattttttc tttttgaga cagagtctcg     47520 ctctgtcact caggctggag tgcagtggca caatctcagc tcactgcaac ctccgcctcc   47580
caggttcaag gcactctcct gactcagcct cccgagtagc tgggaccaca ggcgtgcacc   47640
accatgcccg gctaagtttt tgtatttta gtagagatgg ggttttacca tgttggccag    47700
gctggtctca aactcctgac ctcaagccat ctgactgcct tagcctccca aaatgctggg   47760
attacaggca ggtgtgagcc actatgtgcg gcttattcaa tttttttttt ttcagactgg   47820
gtcttgctgt tgcccaggct ggagtgcagt ggcgcaatca tgcctcactg cagcctcaac   47880
cttcctggct caagtgatcc ttccacctca gtctcccag ttactgggac tacaggtgca    47940
caccatcact ctaggctaat ttttgcattt tttgtagaga tggggttttg ctgtgttgcc   48000
caggctggtc tcaaactcct gggctcaagt gatcctccag cctcagctcc ccaaaagtgc   48060
tgggattaca ggcgtgagcc accatgccta gcctccttcc cacttctgaa taggtgggta   48120
acccaggtcg tgttgttgag acccttcag tcaccgtggg tgactcctcc tagctcacct    48180
cctccaccat cagagctggg gctctagagt ctggatagtc tccaattcaa ggcaagctcc   48240
tccagtaaga gcctcagttt actcatctgt caaatgggat gagaacacct ccttcacagg   48300
gtggttgtgc ctgaagcagg gaaggcactg tcactggctc catcatgatc tgctatgata   48360
taaatagtag gatgctgttt gctaaggaca tatttgttga gtgagagatt agaagctgcc   48420
tggctccagc ctgagggtca gcgtgggcca gaggggctg gcaaagcctt ctgggaagag    48480
gaacctgtga ttgactcgga cacggggccg ggggcgggac tcaagagatc ctcccacctt   48540
ggcctcccaa agtgctggga ttacaggcct cagctgccgc acctggccaa ggctgagcct   48600
ttaagtggct cattcaggat ggcggaggct ggaccagccc agggcccttt ctgctgtgac   48660
tgcaacccgc ccggtggagg gaggtcagga ccgtgtgtcg gagctgctca gagcatcacc   48720
tttgcttttt gacccagaaa aggttgcctc ttccccagtg tcatggtaac ctcttgaccc   48780
tgtggcagca gagcgtcaga ggggcctgct gtggcccggc ctgggtgtct ggcaggtgcg   48840
tatctgtgtg gtaggaaagg aaagaaaagg aggccttgga cgcagcccag gtgagcgggg   48900
ccagaatggc tcccctgtct ggaaagaaat gtcatgggca gcccaagtcc ctataatcca   48960
agacaagtgg gcactggctg agggcgtgaa gcatttcctc tgcgtgaggc ctcatttaag   49020
tctggggagg caggagtgca tatttatttg tagaaaaata gcaacatgta agcaaggaga   49080
gtgaaatgag atcactcacc cacagtccct gaaaagcagt attttggtc tcatttggc     49140 cactcaggaa accgatcatc acaatgcaaa gttatgataa catcataata ctggaaataa   49200
tattaatcac cagtggtgat caaaacaata gtggttttta ttagaaacaa taatagaata   49260
```

```
caaataaaaa tagtgataat aatgataacg taataataca acagaaataa gaataataaa    49320
acagcagttg tcttttttgtt tgtttttgct ttttcagagt ctcactctgt tgcccaggct    49380
ggagtgcagt ggcacagtct cggctcactg caacctccac ctccctggtt caagcgattc    49440
tcatacctca gcttccccag tagctgggat cacaggcatc caccaccaca ccccgctaat    49500 ttttatatt tttagtagag acagggtttc accatgttgg ccaggctggt ctcgaactcc    49560
tgaccttagg tgatccacct gcctcggcct cccaaagtgc tgggattacg ggcgtgagcc    49620
acagcgcccg gctaaaacag cagttatctt atgccggtac tgtttgctca gccccgtggc    49680
cccactctga gggaggggct atgatgatgc ctgcatcaca gatgtagaca ttgaggctca    49740
gagatgtgga gctacttgtc caggatctgg cagtcggtgg tgccgacaca ggagttccag    49800
ttatctgacc ttggggcctg tgctgtctct gaccgaggca ttggagagct cgcagagtc    49860 taaaatattt tgcctgggct gtcgagttct gtttcatttc ctgcaggcct tccaattgaa    49920
cacgactctg ccatttgaaa gtcttaaaaa taaaacccaa acccacagcc agccacccat    49980
tcgagctccc caggatctgg gggcggactg ggtggtgggg gttgttgagc ctgcctgggc    50040
cacaagcctg cttctgcaca gcctcctgct gggctgggac tggccctgtc ccggagtgcc    50100
cgtccttgtg tcccggggct cctgccctaa gcagggatga agatgaaaac tagggggcctt    50160 ttgctagggt gttatgagag ctctgtctgc tctttctaga aaagacaggg atttgagctg    50220
ggtgtgggca gtttatacat agacggctga gggcagctct gtgacttggg caaagcccac    50280
tgtgtgtggg ggtggtaggg gaaccatttt cttttcctgt aaatattttt atacccggta    50340
ggaagaagcc tgcaggtcct attgtgtgag cacaatgggc tctccttctc caggagtgtt    50400
ttgtgtttcc ccttgaagag cagcagggag ggagctgggg agaggggac atggtgaagg    50460 gggtggagag acgggactgc agggatgggc cagcgcagag ccaggaagcc aggaaggtgc    50520
aggcatgatg gcaatcaccc tttctccatg agtgcatctg agaaatgttt ctttttgcaa    50580
aaggcacctt atttattgta gaacaaatag aatttgcaga ggaacactgt actctcctgg    50640
gttccctccc atccaagacg aagcctcttc cactgtggtc tatctccttc cagaagcttt    50700
ctggtgcttt tctgctcagg acgccttgca cctggccata gcttcgcttg gcccccaac    50760 cctagtttaa agatctccct tctccttccc catccccaga taagtcagtc cctgaggatt    50820
ggaggtcgtc acagacgctg agtcctaccg tagtggtcat ggcggtcctg tgcattatgc    50880
acctgcctgt caggtgccaa ctcttactgt tcccatttta cagatgagga aactgatgct    50940
caaagtgact agacacactg tgagtcaggc agagctaggg cttgtagga aggtccgggc    51000 gtttctgcag cccatgtagg tcactagcct gccaggacgc gggtcagaca tcaaacaccc    51060
ccagacagag gccccctcca ttcccctac tccttttag gaaggcgtct catcagccat    51120
cagagctgac aggctctctg gagccacctt gttcaagtta tcattgccct gaggggaaac    51180
agaagcctag agctggggag aggcttgccc aggcactggg gccctcgcag ttctggcctg    51240
tgggtgtgtc cccgtgccc ggagcgacct cggggcacca gtgctgtagc tgtaggtggg    51300
tggggagcaa ccatctcccc agacccttcc aaggtagcgg tgacagccca aggctgggat    51360
ggagagggag agcctggctg tggccaggcc ctacatcagt gcctgtcctg ggttcaagtc    51420
ctggcatcac caccctgcct ggatgctggg tgagcccctc cacggctccg agtctcgctc    51480
ctcctctgca gaatgatga gatgcagccc ggcctcagag gccttgggag gacttgggga    51540
gacccaaaat ggaggacatg ctaggcaggg ggtgcgcaca caggctctgc tggctgggcc    51600
atcagcttca tggggagcac caccccccca gacctgggcc tcactcccca cccgctcctg    51660
```

```
cccacaggtg ccactggacg agcgcatcgt cttctcgggg aacctcttcc agcaccagga    51720
ggacagcaag aagtggagaa accgcttcag cctcgtgccc cacaactacg ggctggtgct    51780
ctacgaaaac aaagcggtga ggcctggccc cgggcgccac actgagcctc cccgctttct    51840
ccatgtgtgc cccctccccc aactcggaaa cttaggcccc agacgccacc gtcacagcct    51900
gcacgcggtc accagggcca gagcaccacc tcagcccctc ccctccccca aactgggctg    51960
ccctgggtgc cctctctgga cggcagctca ttcttcatct ctggggaata tcgctgactc    52020
cttctgtccc tcataaacca actgtcactc actcctcccc atccctccta atctctcttc    52080
agtccctcca gctggctcca gggcgttcct cctgccacct ccttcctcac tgggcttcct    52140
gcctctcctc cgaccsctcc caccctcgac agccacagag agctgttgga ggcacaatct    52200
ggccattcct tgcggtggct tgcccctgcc ctacaggtgg gtaggtgtcc gagaaggaca    52260
tcctatggga gcattgtgcc ttatcttttc cctgagccct cagggaagcc ccacctggtt    52320
gagccacaga cctgatttct tcaattgctc atttctccag agcagccaga aggacaggcc    52380
tgggccctgt atttcacgga agatcaatgt tagagcaaca taaagtcaag agcaacctcg    52440
tgccccagag tagtggttct caactggtag cacgtccaaa tcacctgaag ggcttgctga    52500
aagacacggt gctgggcttt cccccagagt ttgattcagg ttgggagcca agatttgcat    52560 ctctttttt tttctttttt ttttttttt tgagatgaag tctagctctg tcgccaggct    52620
ggagtgcagt ggcgccatct cagctcactg caacctccac ctccctggct caagtgattc    52680
tcctgcctca gcctcaggag tagctgggac tacaggcgtg caccaccatt cccagctaat    52740
ttttgtattt ttagtagaga ctggttttca ccatgttggc ccggatggtc ttgatctcct    52800
gacctcatga tctgcccacc tcggcctccc aaagtgctgc gattacaggc gtgagccact    52860
gcacccggac tgtaaagatt tgcatttcta gtaagttctc gggtggtgtt gaagatcaga    52920
gaccatgttt tgcaaatcag tgccctacag gttctgagct actttcagga actgtgttgt    52980
atagtgacac ctagtggcag ggagtagcat ggtagccctg ctgtatgagc tattccatca    53040
gaactgcttt gccccctgct actggtgtaa gtttctagac ctaattctcc agaggacgct    53100
tgtgtgatgc tcagaaccta ggaaattggt gggggcagtt cagggtaatg gtcaaatacc    53160
ccaggctctg gagatagata gccctggttc atgtcctaca tctgctactt cccaactgtg    53220
tgaagttggg ggtgatccac ctttttgaatt gggaaaattc tgtgaaatta agcatgcaat    53280
gcccttagca cagggcctgg tatgtaagaa atgcttaact agtggagctg ctgggaacag    53340
aggcaatagc agcagtagaa acagaacaac aacctcggcc aagctcgctg agtccttgtg    53400
gtgtgccagg cactgcagat tatctcactc agtcctcaca tggctctgtg aggcaggaat    53460
ggttattacc ctggttttgt ttttatttta aaatgttttc cccatcctga atattcttga    53520
ttccctggtt ttatagatga agaagctgaa gtttaggcat ttaaggaatt ttatcctcag    53580
catcacacag acactaccca gtgaagccag gaattgagcc cagagctggg gtctaggttg    53640
ctgtggatgc cacactgccc caatcaccat gatagtgaca ttctcccctc tgttcctctc    53700
ttgcctcttc ttcctttccc ttctcctccc cactttgggc cacactgagt agggccttga    53760
agccaggtgg gatttgggct tggccgcacc ttaaccctca gggaccctct ctcttgcctc    53820
cctcaggcct atgagcggca ggtcccacca cgagccgtca tcaacagtgc aggctacaaa    53880
atcctcacgt ccgtggacca ataccctgga gctcattggca actccttacc aggtaaagga    53940
gcacccatcc caggccacaa tgccctgcac aggcatctgg agctggccag gggagggtg    54000
```

```
gccctgagcc cattgctttc agccccatgt tgcggagag accaactagg cttagagctg    54060
tggatggaga cctcattgtt tgcctttcgc atctccctaa gtccttgaga gcctcctgga    54120
agatgttcag tgaccttccc tcgtaaacct gtgggtcagc actgtgttcg tcaggagtta    54180
ctcttcttgg catcctgctt ttgcttcacc ttggctgaaa ttccctagaa gccttacggg    54240
aacaacattg gcctctctga tgatccctgg gaactagagg gcaggggaca tgcctgcctg    54300
gggggcaggt catgcccag ggacttgaga gtagagtcat gccttcattc tgtggtgatg    54360
gagggcctgg gcattcctgg attcgagcgg cattcctgga ttccagcagc attcctggat    54420
tccagcgtga ctctggcttt gtttcactgt gtctgcttgg gcgagtcacc cccctcccc    54480
tgaatctcag cctcttcagt gtctacaaag cacaggcact aagaggactg ccctcgggt    54540
gttgtgtgga ccctggaggg gcacaggcca acccagagcc agggcagaaa gaagaactgt    54600
tattgtcata tcattaacaa cagtggcagg gtcacagccc aggaccagtt atctcgctgg    54660
atcttacata tccttgagaa tgaaattgaa ggagggaaaa attccttttg ctgtattttg    54720
tccctcccca catgcctccc tccccctgtg gacacttaag ccacactttg gcctccacag    54780
ccgaaatctg aagggaaacc caagaaggta gtgcttgacc cttgaacctg ggggctctga    54840
ccttgtgttg tttgtgcttt acagagttta aaacctaacc caagagtggg gtggatgtga    54900
cttattaccc actctaagaa atgggtctgc acggatgctg gactcaggtt ttgggctgag    54960
gagaacacag ccagaaagaa ggctgctccc accccgccg gcttgctggt caccttggga    55020
caggctggcc ttctctgggc ctgagcctga cctcagagct gatgccaagg gatcagttct    55080
ctgacatcct ctggtggagg gcaaccacag agggcagctg ctcatcaggc actgtctcca    55140
cagggaccac ggcaaagtcg ggcagtgccc ccatcctcaa gtgccccaca cagttcccgc    55200
tcatcctctg gcatccttat gcgcgtcact actacttctg catgatgaca gaagccgagc    55260
aggacaagtg gcaggctgtg ctgcaggact gcatccggca ctgcaacaat ggtgagtggc    55320
ctgtgggtgc agggtcggtg ggagggaggg gcaggacctg ggttattgct gaatggtgac    55380
acctagtggc tgactatggt gtggcaaccc tgctctacag gctgttctaa tttcccttct    55440
ggggttataa gaaaccatgt aataccaccc ttagtcttct ttcttgatga aaacagtttt    55500
gtgctgctca ggaaaaaagt aggaaattat tcacagaggg gtgtggttgt tgagcccttg    55560
gaccctgagt cacaaagtca caatcctgat tctgccattt tccagctacg tgaccttagg    55620
gaactgactt acctcttgga ggctctgtaa agtggggata atgccttgtg tgtcttaggg    55680
gggttatgag gatttagagt ctacctcatg cttggtaaag atttttttt taattttata    55740
tatatatata tatatatata tatatatata tatatatata tatatatata tatatatttt    55800
tttttttttt tttttttttt aaaaccacca acctgcaggg tgatttggaa acttcactgc    55860
ctccctcagg gcctcattgc tctcatctgt aaacttatgg ggtgactctt ccagctcact    55920
catttattca acaaacattt ttagtgtcta ctctgaggag gcccagattt aggcactggg    55980
tgtgcaacaa gggagcaaga acattccct gccctcctac aattggcagt ctggtagggg    56040
agacagatga tagacagatg aggatgccag cacgatggct cacagctgtg ctgggtgctg    56100
ggtggagcca acctgggagc ctgagggtgt gtgtgtgttg gggagggggt cgatcagggc    56160
aggctcccctt gaggaggtta tggttcagct tcagcagaga cctgaaggag aagtcccaga    56220
cctgaaggag gagatgccag aagtcccagg gcccctcata tcctgcatag aggagagggg    56280
aggagtgttc caggcagagg taggcagtca gcatgaaggg agacccacag gtggtagggg    56340
taggcccgga ggaggaactg cacgaggccc tgaagcaggg agggggtgac ctgaaatggg    56400
```

```
gctggagggg ggcctctggg gtcaggtctg gaaaagcctt gaaggcctct aaggaatttg    56460
aacagaaagg ctgaggatgg tcttccaagg tgagggtggg tccctggggg tctttctgcc    56520
cctagggaag gaacaaccca gtcctggaca ctgaactgct tccaggtgat ctggcctgag    56580
ggaagctcct gcccccgccc cacccttggg cgcagtgcca catggtgcag aggtggaagg    56640
ttgcagggga cggagtgggc gccaatggcc tctgggctgc tgccgtggga ctcagctcac    56700
cccacccctc ctgctcgcct ctccagagcc acctctgccc tgtctggaat ctgccaagca    56760
ggaggaacca ggtcttcaat caggccagcc cctgccacct gggcccagct gcccacaaag    56820
ggcctcctgt tcccaggtcc cggggactgt gggctgggac tgggtggagg cactcaaggc    56880
tctggctgcc tggcccaggg ccctcccgcc tccccagccc ctggcctggt gccatctctc    56940
caggtttcca aggctaacgg ctgacctggc ctggcagggg gggtgacctg cgccagatag    57000
ggaaggggtg ggcacagaac aaggtgggga agggccacct cagtccccca tgtgtgcagt    57060
ggggatgatg ataaacttga gcttgagaga tgattgggaa gagctggtct gggtggggca    57120
cttggccgtg ggcctggcac gcacagtgag cactcagtgg ggaggccatg ggggagttct    57180
tggttctaag gtgcagtgga ccagaggag gcccaggaga gctgctgggc cagggaatga    57240
aggggtgtcc tgtgccagga aggtgtcctg ccgggtggcc ccttctcccc agggcgggag    57300
ctgacgaggc tggtttcagg ccttccttcc accctgcgga ctgtgagaaa gttctctgct    57360
tcctccgtct tggaggctgg gcttggaatt tgtgaagcct ggaattgctc actccggggg    57420
ctgccaggaa gtgggggtg ggggaagga ggccaactgg gcggacacca gcggtcccag    57480 ggacccttc acatcctgca ttcctggagc agctgggggt ggcaggaggc agctgggca    57540 ctggctgtgc cgggtcctca gtgttggcct ggggtgcaga ggtcaaggct tcttcctgtc    57600
tgaccgtggt cccctctgt ctgctgcctg ggagtgagga atgcagtttc ctttcttgga    57660
aggtctccag gtctggctag agtcagctgg tcctgggttc aagccccgct ctgccatcca    57720
ctagctgagt agcctcgagc agtaactgcc tctctgagcc tcagttcttt ccctgggaaa    57780
agtagggcac agtgagctga ggattcaacg agctgatgtg tgtgcagcct cagccagggc    57840
tggggcctca gtttcccaag actgccataa caaataccac agaccgggca gctacacagc    57900
agaaatatgt tctctcccag ctggaggtct gagtcgaggg caaggtgtca gcagggctgg    57960
tttctccgag acctctctcc ttggctggtg gccggccgcc ttctccctga gtcctcacag    58020
ggtcatgcct ctgtgtgcct gtgttttctc ttctttcaag aagaaatgta cttttctttt    58080 tttcttttc ttttttcttc tttttgaga cagaggcttg ctctgtcacc caggctggag    58140
tgcagtggcg caatctcggc tcactgcaac ctccgcctcc caggttcaag tgattctcct    58200
gcctcagcct cccgagtagc tgggactaca ggcgtgtgcc accacacctg gctaattttt    58260
tgtagccaga atggtcttga tctcctgatc tcgtgattct gccgcctcgg cctcccaaag    58320
tgctgggatt acaggcgtga gtcactgtgc ccggccaaaa tgtactattc ttttaagggc    58380
actagttgta ttggatttgg tcccatcctc atccctctg tttaacttaa ttctttaaga    58440
ctctaggacc aagggcgggt gcggtggctc aggcctgtaa tcccagtgct tgggaggct    58500 gaggtgggtg gatctcttga ggtcaagagt ttgagaccaa cctggccaac atggtgaaaa    58560
cccatctcta ctaaaaatac aaaaattagc tggacatggt ggcgggtgcc tatagtccca    58620
gctacttggg agctgaagcg ggagaatggc ttgaacctgg gaggcggagg ctgcagtgag    58680
ccaagattgc accactgaac tccagcctgg gcgacagagt aagactcttc tcagaaaaaa    58740
```

```
aaaaaaaaaa aaaaaaaaa gaccctgggt ccaaatataa tcacgttctg gggtactggg    58800
ggttaggact ccagcatatg aatttggggg gtgtggagac acacttcagc ccctaacagc    58860
taggctcacg ggaagagctc aggaggggtg accctgaaac ttgtcacact cagcggctgg    58920
gtgtgcagaa agagagaatc ccaagggtca aggctggctg gcctccctcc cgctgtcccg    58980
gccctctgcc tcaccttctc gccacctgga aagcaggcct gccctgcaca cctgacttgg    59040
tgcatgcagg atgaaaattc cctctccccg tgggagtgcc tgcaggtaac gcactgtcca    59100
gattttccag tcaaaacttg gtttctagga aaccatgccc ttctgagagg cgggtggggt    59160
ggcgggggga cctccttccc tggcccaggt gggcagcccc cacccagggc tctgcatgct    59220
gctccagctg gaacatccct gccctgctcc tgtcactcct gcctgacttc aggtctctga    59280
aatgcaggag tgagactccc acaggccccc gtccccatcc aggcagctgc gctgtaggga    59340
tgagggctgg gcctccccct gctcagctcc ctcccggctc cgacaggcag tgatttctgt    59400
ggtcagctgg gtgtggggag aggagggacc cagagagggg cttttctct gccggtggtg    59460
actcagccca tagtcatggc agtgggagcc ttaggtttct gatgcacagg cttccgtttc    59520
cccttcctgg gctttgggga tgcggtggtc agaggcacgc ggccagggga gtctgcctgc    59580
tgcctggctc ggtggcgttt gaccaccttc ttaccccaag tcagattttg taacttcctg    59640
ccaattgcct cccgggcact gaatctggag gtccacgcct cactcagggg tttaccttgc    59700
tggcgtttgg gccactgaca gcaccaacag tgacaaaaat tcagaaatgg tgttcttcta    59760
gctgttatta atagcaaact cttccattct tttttttttt tttttttttt ttttgagac    59820
agagtcttac tctgttgccc aggctagagt gcagtggcgc aatctcggct cactgcaacc    59880
tctgcctcct gggttcaagc gattctcctg cctcagtctc cctagtagct gggattacag    59940
gtgcctgcca ccatgcccag ctaattttg tatttttagt agagatgggg ttttgccatg    60000
ttagccagac tggtctcgaa ctcctgacct caagtgattt ccccacctc agcctcccaa    60060
agtactggga ttgcaggcat gagccaccac acccagcttc attctttaac aaagttattc    60120
aagcatctgt gccaggtact gacctggact tagcagtaac aggacagacc ccgggcccag    60180
tggggcaggc agctggctcc tcagttattg ataaaaagtg tggcgcagag cagtgctgga    60240
ccctgatctc ctgtccctac actgtggccc agggagcccc gcagtggacc tgtgaggcca    60300
ttgttccatt gttcagaaga ggaaacaggc catttcgggt tcagtgatct agaaccaggc    60360
tctgaaacct atggcctatg ggcccagatc agccaattgc ctgtttctgt caacaaagtt    60420
tattggagca gaggcacgct catttgtttc tggatggtcc gtggctgttt ttgtgctgtg    60480
actgtagagg cgagcattgc gggagggtt ttatggcctg ccgggctgag aatatctgct    60540
gcctagcctg ttccaggcaa agtttgaagg gccctgatct agcagtaagg gaggaactgg    60600
ggctcgaaca agggtctctg ggtgcctcta gggccattct gggtggctgc ttatgggacg    60660
ggagctttta gtcctggctc tgccactccc tgctctgtga ccctgggccc gtggcctgtc    60720
ccctaacggt tgtctcttca tctgtaatca tctgtaaagc aataaggtga atgatagtgc    60780
ccaggtcttg gggtggttgg gaggatttca ggagctaagg aggaggcaag ggggctgcct    60840
tgtcactgtt ggtggtgggg tcattactgc ttttgcctat cagatacaac catgactgct    60900
ctgatgacga ggaaagtgag ggtcccagct gcccctcctg aggtgcatgc catgtgtgtg    60960
gggggggttt tggtcagttc tcagttggtc ttggtagagg ccactgggcc atctgctgac    61020
ctcctctctc cctccgtctc ctgggcagga atccctgagg actccaaggt agagggccct    61080
gcgttcacag atgccatccg catgtaccga cagtccaagg agctgtacgg cacctgggag    61140
```

```
atgctgtgtg ggaacgaggt gcaggtgagg ccagacgggc tggtgaggaa acctcagaag   61200
tcacccaagg acccagcagg ggagggcagg gggtggggta cagagatggg gctctggggc   61260
gctgccggtt tggaaggaga tgacatgctt agatttggac aagtgcaggg ccagtgcacg   61320
tggagatact cgctgtctta ttcatcactt actgggcatc tgagcaccta ccctggacga   61380
ggcactgggg tgcagctggg aatgatgtgg acaaattcct ggccctcagg gagctctccg   61440
tatagcagga gaaacagaca tttggcaaat aaatgtacac ttccatgtgc aggcaaagca   61500
gggagggagt atggtattct aggtagggaa ggcagcctgt gcaaaggccc tggggctggc   61560
ccttgagtct gaggatccta caggacaccc aggcagatga gttgggacct gtgggaatgg   61620
agctcaggag agagggcagc agggagggtg aagcaatggg ccagtcgcgg aggaggtggg   61680
ggctgcagcg gcctggcttg tgggaatgca gagagaaaca ggccagctga gcgctctcca   61740 gccctggcc tggcttgtgc ctcctcaacc tagatcctga gcaacctggt gatggaggag   61800
ctgggccctg agctgaaggc agagctcggc ccgcggctga aggggaaacc gcaggagcgg   61860
cagcggcagt ggatccaggt gggtgggcct ggggccctgg agcggggacg ggacctgcag   61920
ctggtgcggt gccctcagcc ctggtgccaa ttcagctgct ctgcccacag atctcggacg   61980
ccgtgtacca catggtgtac gagcaggcca aggcgcgctt cgaggaggtg ctgtccaagg   62040
tgcagcaggt gcagccggcc atgcaggccg tcatccgaac tgacatggac caaattatca   62100
cctccaagga gcaccttgcc agcaagatcc gaggtaggca gccaccccg tgctcgacgg   62160 gccctccagg ggccaaggtg gactttcttt ttatttcatg attcatgtaa atttcacagc   62220
aatgacttgc tcattgatca tttgtaagaa ttagagccaa atctgcactg tggtactcca   62280 accctgtga gttgttttgt ggctattatt tctataagcc cagaacttga agagaaaaat   62340
ttttgttctg gaggttcaag ccttctttc atctctgact cgtcacagat ttttaccatg   62400 tgtcattta aagtacattt acgttcagca agtatagctt tcccaggtca gtttattctg   62460
tcacccaggc tggaatgtag tggtgcgatc tcagctcacc acaacctccg cctcccggat   62520
tcaaacaatt ctcctgcctc agcctcctga gtagctggga ctacaggcac acgcgcgcca   62580
ccatgcccgg ctaacttttg tgtatttagt agtgatgggg tttcaccatg ttggccaggc   62640
tgatcttgaa ctcctgacct cgtgatccgc tcaccttggc ctcccaaagt cctgggatta   62700
caggcatgag ccactgtgcc cagactgtac gcctttctct tcccagccag atgggatcct   62760
ttcaccagct tggtccccat aacacatctg cagagctcag ttttagcaat tgtcagttgc   62820
ccatgggacg ttcttttat tttatttat ttcatttat tttatttgag acagggtttc   62880
actctgtcgc ccaggctgca gtgcaatggc acgaccttgg ctcactgcag tctctaccat   62940
cctcccactt caaccccca gtagctggga ctacaggca tgtgccacca cgcccagcac   63000 attttttgtat ttttttgtaga cagggtttt tgccatgttg cccaggctgg tctcaaatgc   63060
ctgagctcaa gcaatccacc caccttggct tcccaaagtg ctaggattac agatgtgagc   63120
gactgtgccc agccattatt attattatta ttttgagatg gagtcttgat ctgttgccca   63180
ggctggagtg cagtggcaca atctgggctc actgcaacct tgcctctcgg gttcaagcaa   63240
ttctcctgcc tcagcccctc aagtagctgg gattacaggc acctgctacc atgcccagct   63300 aattttttgta tttttagtag agacaggggtt ttgccatgtt ggccaggctg tcttgaatt   63360 cttaacctca gtgatccac ctgcctcggc ctcccaaagt gctgggatta caggtgtgag   63420
ccactgtgcc tggcctgttt tttttgtttg tttttttttt tttttttttg agacggagtc   63480
```

```
tcgctctgtc gcccaggctg gagtgcagtg gcgtgatctc ggctcactgc aagctccacc   63540
tcccgggttc acaccattct cctgcctcag cctcctgagt agctgggact acaggcgccc   63600
gccaccatgc ctacctaatt ttttgtattt tttagtacag acaaggtttc accgtgttag   63660
ccaggatggt ctcgatctcc tgacctcatg atccgcccac ctcggcatcc caaaatgctg   63720
ggattatagg cgtgagccac cgcgcctggc cgcccggcct gttttttaag agacagagtc   63780
tcgctctgtc ttccaggtag agagcagtgg tacaatcatg gttcactgcg tgacctcctg   63840
agctcaagta gtcctcccac ctcagcctcc tgcgtaactg ggactacagg tgcaggccac   63900
cacgcctggc taattttttaa attgtttgta gagaaagggg tcttggctgg gcaaaactct   63960
atctctttta aaaattttg aaagagagag agagaagggg gtcttactgt gttgcccagg   64020
ctggtctcga actcctggcc tcagacaatc ctcctgcctc agcctcccaa agcactggga   64080
ttacaggcat gagtggccgt gcctggtctc ctgtaggtta ttctttacta gccagatcct   64140
gagtattggt tgacagctgg ataggacact gagcattgac atttcttgtg tggaacaaag   64200
aacgttagct gggctgggat gggggtggac atctaaatat tcttgagtga aaatgctttg   64260
gtcagaatgt tctggagatg gtccccaccc aaaggaagaa ggcttttaca taattatgca   64320
gagccagcca cactattcca gagaggatca gcccagtttt tgtaaaacca agaggctcat   64380
tgaatctact aaggtatttt tcattgctgt tgttcttttt gttcaaacga agaagcaaga   64440
cccatcctaa aggagttttt gtctactict agctaagcag aacactgctg acacctctgg   64500
gctggcagtt ttcttatttt attttatttt catttcatt tttaattttt gtgggtacat   64560
agtaggtgtg catatttatg gggtacatga gatgttttga tcaggcatgc aatgtgtaat   64620
agtcacatca tgggaaatgg ggtatctatc ccctcaagca tttatccttt gtgttacaaa   64680
caatccaagt atattctttt agtttttttt ttttttttg gacacagagt ctcactcttc   64740
ttgcccaggc tggagtgcag tggtgccatc tcagctcacc gcaacccctg cctcccaggc   64800
tcaagtgatt cttctgtctc agcctcccaa gtagctggga ttacaggcac ataccaccac   64860
gcccggctaa ttttttgtatt tttagtagaa atgggatttc accatgttgg ccaggctggt   64920
ctcaaactcc tgacgtcaag tgatcttcct gcctcggcct cccaaagtgc tgggattaca   64980
ggcctgagcc actgcacctg tgcagcctct tttagttact tttaagtgta caattaaatt   65040
attattgatt atagtcaccc tgttgcgcta tcaaatacta gggcttattc attctgtaac   65100
cagaaagggg tcccgatcca gaccccgaga gagggttctt ggatcttggg caagaaagaa   65160
ttcaaggtga gtccatagag ttaaagcaag tttattaaga aagcgaagga ataaaagaat   65220
ggctactgcg tagacagagc acgagggctg ctggttgccc attttatgg ttatttctga   65280 tgacatgcta aacaagggt ggattattca tgcctccctt tttagataga gcatataggg   65340
agacttcctg acgttgccat ggcatctgta acctgtcatg gtgctggcgg gagtgtagca   65400
gtgaggacga ccgaggtcac tctcatcacc atcttggttt tggtgggttt tgggccacct   65460
tctttactgc aacctgtttt atcagcatgg tctttatgac ctgtatcttg tgccgaccta   65520
tctcatccca tgacttagaa tgccttcacc gcctggcagt gcagcccagt aggtctcagc   65580 ctcatttac ccagctccta tttaagatac agttgctctg attcaaatgc ctctgacatt   65640 tctactttt gtgcccatta accattccca tctccccctc gccctcgact accctctcca   65700
gcctctagta accatctttc tactctatct ccatgggctc aattgctttg ttttctgctt   65760 gtttattgt ctgttttac cttttttatt gctcccacag gggaggcccc ctccaaaatg   65820
tcaatttgct ttaattttta gatcccacaa ataagtgagg acatgtgata tttgtctttc   65880
```

```
tgtgcctggc tgaatataat gacctccagc tccaaccatg ttgttgcaga tgactgaaac   65940
tcgttctttt ttacggctga atagtacccc atcgtgtata tgtaccgcat tttctttatc   66000
cattcgtctg ttatggacac ttaggttgct tccaaatctt ggttgttgtg aacagagccg   66060
caacaaacac gggagtgcag atatcgctgc gatgggctga tttcctttat ttgggtatat   66120
acccagcagt gggattgctg gattgtgtgg tagctctatt agttttttga ggaacctcca   66180
aactgttctc catagtggtt gtactcattt acattcccac tgtgaaccct gaaaatttga   66240
ggcaggtctc agttaaatta gaaagttgat tttgccaagt tggggacacg cactcgtgac   66300
acagcctcag gaggaactga tgacatgtgc ccaggtggtc agagcacagc ttggttttat   66360
acattttagg gaaacctgag ccatcaatca acatacgtaa aatgggccgg gcacagcagc   66420
tcaagctgta atcccagcac tctgggaggc cgaggcgggt ggatcacttg aggtcaggag   66480
ttcgagacca gcctggccaa catggtgaaa ccccgtctct attaaaaata caaagcttag   66540
ctggatgtgg tggcgcatgc ctgtagtccc agctgctcta ggaggctgag gcatgagaat   66600
tgcttgaacc tgggaggcag aggctgcagt gagccgagat cgagccacta tactccagcc   66660
tggtcaacag agtgagaccc tgtctcaaaa aaaaaaaaaa aatgtaaaat gaacatggtt   66720
cagtccggaa aggcgggaga acttgaagga aaagcaggac aactcaatgc aggcatgagg   66780
cttccaggtc ataggaagaa aagagacaaa tagttgcatt cttttgagtt gatgattagc   66840
ctctccaaag gagggaagca gatatgcatt aatctcagtg agcggagggg tgactttgaa   66900
tagaacggga ggtgggtttg ctttaagcaa ttcccagctt gacttttccc tttagcttcg   66960
taattctggg ggcctaagat attttccttt cacaccacca gcagtgtacg gaggttccct   67020
tttctccaca tcctcgctag catttgttat tttcttttttt ttggataaag ccatttttaac   67080 tggggtgacg tggcatctca ttgtagtttt gatttgcagt tctctgatca gtgatgtcaa   67140 gtacctttc atatgcctgt tttggggttga gtacctttca tatgcctgtt tgccatttat   67200
atgtcttctt tgggggaaata tgtattcaaa tcttttgccc attttttaatt ggattactag   67260 gattttttc ctatagactt gtttgagatc cttatatttt ctgattatta atctcttgtc   67320
agatggcagt tttcttagtt ttttgccatc atggtttcag aaagatcaga gtccaatctc   67380
agaacacctt gtcattttc ctgcatggat ttctcatctt tatccactat ttctctgaaa   67440
tcattcagct tgctaatgtt gcccccagtg gttttttttt ttaaataata ttggccaggt   67500
acggtggctc atgcctgtaa tcccagcact gggaggcca aggcaggagg atcacttgag   67560
cccagggagt ttgagaccag cctggataac acagtgagac tctgcctctt aaaataataa   67620
taataataaa agtattgatg ggggctgagc gcggtggctc acgcctataa tcccagcact   67680
ttgggaggcc gaggtgggcg ggtcacctga gatcaggagt ttgagaccag cctggccaat   67740
atggtgaaac cctgtctcta ctaaaaatac aaaaaaaaat caccgggcat ggtggtgcac   67800
acctgtaatc ccagctactt gggaggctga ggcatgagaa tcacttgaac ctgggaggca   67860
gtggttgcag tgagctgaga tcgtgccatt acattccaga ctgggcgaca gcacgagact   67920
ctgtctcaaa aattaataac aataataata tgatgggaag agagagttgg gagagggctg   67980
aaaaattact ttttgggcac tgtgctcatt acttgggtga tgagatcaat cctacccaaa   68040
acctcagggt cacacaatgt acccatggaa caagcctgca gtgtaccccc tgcatctaaa   68100
ataaaagttg aaataaaaat gataataata ttaggaggct gaagtgggag gattgcttga   68160
gcccaggagt ttgaggctac agtgagcttt gattattcca ctgcactccg gcctggacaa   68220
```

```
cagagtaaga ccctgtctca aataaaataa taataggccg ggcatggtgg ctcatgcctg   68280
taatcccagc actttgggag gccgaggcgg gtgatcacg aggtgaggag tttgagacca    68340
gcctgaccaa catggtgaaa ccccgtctct actaaaaata taaaaattag ctgggcacag   68400
tggcacgcgc ctgtagtccc agctactcag gaggctgagg caggagaatt gcttgaacct   68460
gggaggtgga ggttgcagtg agctgagatc gcgccactgc actccagcct gggcgacaga   68520
gcgagactcc gtctcaaaaa aaatataata ataatgataa taatagtaat acagtagcct   68580
ccagcacctg ggctctggga tggctgggag gtgctccttg gggagcccct gctgacccgg   68640
ctccctcggg gcacagcctt catcctcccc aaggcagagg tgtgcgtgcg gaaccatgtc   68700
cagccctaca tcccatccat cctggaggcc ctgatggtcc ccaccagcca gggcttcact   68760
gaggtgcgag atgtcttctt caaggaggtc acggacatga acctgaacgt catcaacgag   68820
ggcggcattg acaagctggg cgaggtgagg ccggcaccgc ccctaggagg gggtctcctg   68880
agagtaggtc tggtctgtcc cagagggccc cggctgcgtg actccgggca gccgttcccc   68940
tccaaggccg tccctgtaga cggggagggg ctgctgggga ctaggggcag aggctgtgag   69000
gccagggctg ttggagtcct cgtggggcct gcagtttgag gaaagaggga acattagctc   69060
ccggccacca gcctttagaa accaagagtg gtgctaaaat agaaaagaat ttaacagaag   69120
agagggaagg agggaaggag aggaggggag agggaaggag ggaaggagag gagggaagga   69180
gggaaggaga ggagggaagg agggaaggag aggaggggag agggaagggc gggcttcagg   69240
tggagtaatg agattgataa ggaagaattc acaagtcacg cgccctccaa atggagacag   69300
ccgttgccct tacttgacct cagttatctg gctctcgggg tgaacgtcct tccacagtct   69360
ccatcttggg ctggctgccc ggagcccgca tagttgtcag attgaattta tcctgtatct   69420
tagtttcctc ctttatactc tgaaatgggg agtccacaga ccataataat cccagaatct   69480
gagacctgga gaggaccttg gagagcagga aagctctctc ccaattttga agctgaggaa   69540
actgaggctc agagagggtg aatgacttgc ccaaggtcac ccagcacctc agaagggatg   69600
agtgccttct gccggcaccg aggctgcctc tccacagcgc tgtgccactg gactgcgccc   69660
tccatgcctt cagagcctca tgcttctgtc ctgggccctc ctgggtttac ctttgtggcc   69720
atgagcacca ggtggccatc cctggtagca ggcgccagcc ccagggcctg gacttcgagg   69780
acccaggcaa agtgtgtggg gggtgctgcc tggccacagg gcggccctgc tcagcccccg   69840
cggccccggc ccctgcagta catggagaag ctgtcccggc tggcgtacca ccccctgaag   69900
atgcagagct gctatgagaa gatggagtcg ctgcgactgg acgggctgca gcagcgattt   69960
gatgtgtcca gcacgtccgt gttcaagcag cgagcccaga tccacatgcg ggaggtagac   70020
ccgaggctac gaccccacc ccacaccctg tccactgcct tccacaggcc ccctcgccca   70080
gggggtccct tctgctccgt cccgtcatgc catagccacg cttgcctggc acgctctctc   70140
ctcctctgct tggaacatct gtgcctctgc ccacctggct aattctgact cacttcccag   70200
gtctcagctt agagacccct tcctccagga agctctcctt gcgcccccag gcccctteccc   70260 atatttcctg ttgccttgag gcagggactt gctccagcgt gcagagctgt gagtgggcat   70320
agaccgcttg ccattcctcc ctggcaggcc tcggggtggg gggctggttg aggatgagga   70380
cccctcagcg gcacccagga aggggctgtg gtcaccctgg gggcttcaca tgtccgcggt   70440
atgccctgca gcaaatggac aatgccgtgt atacgttcga gaccctcctg caccaggagc   70500
tggggaaggg gcccaccaag gaggagctgt gcaagtccat ccagcgggtc ctggagcggg   70560
tgctgaaggt gagcggcccc acgccctgcc ccggaccgtc ctaggcgagg ccgagccccg   70620
```

```
agcctcatcc ccggccacca ccaggattgc tgtccctgca aggaggcgcc atggtcctct    70680
tgtgcggatg aggactcgga ggcttgggtc agaccactgg cctcgtccta ccctcagggc    70740
caatggagcc cactgacctg cagaccccccg accccttgt tccctgcaga aatacgacta    70800
cgacagcagc tctgtgcgga agaggttctt ccggaggcg ctgctgcaga tcagcatccc    70860
gttcctgctc aagaagctgg cccctacctg caagtcggtg agcagccccc acctgctcca    70920
gccgtttggg ccctaagttg ggggatggag cccacaggcc tccctctacc cttggccctg    70980
acctctcatc tctgccgccc cacccgggca ggagctgccc cggttccagg agctgatctt    71040
cgaggacttt gccaggttca tcctggtgga aaacacgtac gaggaggtgg tgctgcagac    71100
cgtcatgaag gacatcctgc agggtgggtg ccgtcccggg gtggggactg ttgccaggag    71160
gatgctgggg gcgcagctga gaagtggtgg cagctgaggg ggtcagctaa ggctcaaaga    71220
aaagcccaga cttgcacctg gggtctgggt gaagcccact cttcgctgtg tggcctccgg    71280
agcagcctta gccttgcgtc tctgtgcttt agtttcttct cgcgtccttg gctttgctgg    71340
gagggtcaga ggagtgatta tgatgacatgt ggtcagcagc ctgggcctgg agatagcatc    71400
acggccttgc tgctttcagc aacgaggcct ggaatgagtc acatcccaac cacagacccc    71460
caaggcggga tgagacgggt cttctttgag cagagtccag cacaggggcg gctgtgggat    71520
cagtgctgtg tcctgaccct tcccctgtgg ccctgtagct gtgaaggagg ccgcggtgca    71580
gaggaagcac aacctctacc gggacagcat ggtcatgcac aacagcgacc ccaacctgca    71640
cctgctggcc gagggcgccc ccatcgactg gggcgaggag tacagcaaca gcggcggggg    71700
cggcagcccc agccccagca ccccggagtc agccaccctc tcggaaaagc gacggcgcgc    71760
caagcaggtg gtctctgtgg tccaggatga ggaggtgggg ctgccctttg aggctagccc    71820
tgagtcacca ccacctgcgt ccccggacgg tgtcactgag atccgaggcc tgctggccca    71880
aggtctgcgg cctgagagcc cccaccagc cggcccctg ctcaacgggg ccccgctgg    71940 ggagagtccc cagcctaagg ccgcccccga ggcctcctcg ccgcctgcct caccctcca    72000 gcatctcctg cctggaaagg ctgtggacct tgggccccccc aagcccagcg accaggagac    72060
tggagagcag gtgtccagcc ccagcagcca ccccgccctc cacaccacca ccgaggacag    72120 tgcagggtg cagactgagt tctaggccag tgggtccctg actgctgcac atggcacagg    72180 ccgttcccctt ccggacccag gcaggctcag ctctggggag ggcaccctgg tctgtgcctt    72240
gtgggtggag gcggggcagg gctgtgtggc accgccaggg agcgggccca cctgagtcac    72300
tttattgggt tcagtcaaca ctttcttgct ccctgttttc tcttctgtgg gatgatctca    72360
gatgcagggg ctggttttgg ggttttcctg cttgtgccaa gggctggaca ctgctggggg    72420
gctggaaagc ccctcccttc ctgtccttct gtggcctcca tccccctcatg ggtgctgcca    72480 tccttcctgg agagagggag gtgaaagctg gtgtgagccc agtgggttcc cgcccactca    72540
cccaggagct ggctgggcca ggaccgggag agggagcact gctgccctcc tggccctgct    72600
ccttccgcag ttaggggtgg accgagcctc gctttcccca ctgttctgga gggaagggga    72660
aggagggggt cttcaggctg gagccaggct ggggtgctg ggtggagaga tgagatttag    72720
ggggtgcctc atgggtgggg caggcctggg gtgaaatgag aaaggcccag aacgtgcagg    72780
tctgcggagg ggaagtgtcc tgagtgaagg aggggacccc catcctgggg gatgctggga    72840
gtgagtgagt gagatggctg agtgagggtt atggggagcc tgaggtttta tgggcctgtg    72900
tatccccttc tccggcccc agcctgcctc cctcctgccc gcctggccca caggtctccc    72960
```

```
tctggtccct gtccctctgg tggttgggga tggagcggca gcaaggggtg taatggggct    73020
gggttctgtc ttctacaggc caccccgagg tcctcagtgg ttgcctgggg agccggacgg    73080
ggctcctgag gggtacaggt tgggtgggcc ctccctgagg gtctggggtc aggctttggc    73140
ctctgctgcc tctcagtcac caagtcacct ccctctgaaa atccagtccc ttctttggat    73200
gtccttgtga gtcactctgg gcctggctgt cgtccctcct cagcttcttg ttcctgggac    73260
aagggtcaag ccaggatggg cccaggcctg ggatccccca ccccaggacc cccaggcccc    73320
ctcccctgct gctttgcggg gggcagggca gaaatggact cctttgggt ccccgaggtg     73380 gggtcccctc ccagccctgc atcctccgtg ccctagacct gctccccaga ggagggcct    73440 tgacccacag gacgtgtggt ggcgcctggc actcagggac ccccagctgc cgcagccctg    73500
gtctctggcg catctcttcc ctcttgtccc gaagatctgc gcctctagtg cctttgagg    73560 ggttcccatc atccctccct gatattgtat tgaaaatatt atgcacactg ttcatgcttc    73620
tactaatcaa taaacgcttt atttaaagcc a                                   73651
```

METHODS OF DIAGNOSING INCREASED RISK OF DEVELOPING MRSA

CROSS-REFERENCE TO RELATED APPLICATIONS

This application claims priority from U.S. Provisional Application No. 61/779,307, filed Mar. 13, 2013, the entire contents of which are incorporated by reference.

SEQUENCE LISTING

This application incorporates in its entirety the Sequence Listing entitled "2014-03-10_5475-353958_056-US_SEQ_LISTING_ST25.txt" (96,447 bytes), which was created on Mar. 10, 2014, and filed electronically herewith.

BACKGROUND OF THE INVENTION

*Staphylococcus aureus* (staph) bacteria are a common component of the skin surface and lining of the nasal passageways in humans and other animals, and are usually spread by skin-to-skin contact. Methicillin-resistant *S. aureus* (MRSA) is a strain of *S. aureus* that has become resistant to methicillin, an antibiotic commonly used to treat ordinary *S. aureus* infections. As such, MRSA is particularly hard to treat. When limited to the skin surface and lining of the nasal passageways, *S. aureus* bacteria are normally harmless. However, *S. aureus* infections can occur in situations where the bacteria enter into the skin subsurface or body cavity, normally through wounds (including, e.g., surgical incisions) or other sites such as hair follicles.

MRSA infections often occur in patients having weakened immune systems who have been exposed to MRSA, such as patients in long term care, patients undergoing kidney dialysis, or patients recovering from recent surgery or medical treatments such as chemotherapy that weaken the immune system. Skin wounding events or other forms of compromise to skin integrity (e.g., intravenous drug use) are another major risk for MRSA infection, which risk may or may not coincide with the exposure risk. MRSA is often acquired or develops in medical care facilities, such as hospitals. This type of MRSA is known as health care-associated MRSA (HA-MRSA). But MRSA can also develop in otherwise healthy people not exposed to hospital situations. In these situations, it is termed community-acquired MRSA (CA-MRSA). CA-MRSA has often been found to be acquired by athletes (who may share towels and razors), children in day care, members of the military and people obtaining tattoos, for example.

Symptoms of staph infections may include red, swollen and painful boil-like symptoms, which may be treated locally. In severe cases and in hospital situations, staph infections may be systemic and must be treated with systemically administered antibiotics.

Some individuals seem to be uniquely susceptible to staph infections and developing recurrent CA-MRSA skin infections. Such populations may also have an elevated risk for developing MRSA if admitted to medical care facilities. Treatment for these individuals involves attempts to decolonize the skin and nasal passages of the patient with topical antibiotics, which can be temporarily effective, especially when coupled with improved sanitation such as frequent hand washing and isolation from other patients. Thus, improved methods of recognizing persons susceptible to recurrent MRSA and/or CA-MRSA are needed and can improve patient care and reduce the incidence of MRSA in these individuals.

SUMMARY OF THE INVENTION

We describe methods of predicting or assessing the level of risk of a subject developing a Methicillin-resistant *S. aureus* (MRSA) infection comprising: obtaining a biological sample from the subject, wherein said biological sample includes at least one oligonucleotide occupying a locus corresponding to position 17 of SEQ ID. NO 1; detecting the identity of at least one oligonucleotide occupying the locus corresponding to position 17 of SEQ ID. NO 1; determining whether at least one oligonucleotide occupying the locus corresponding to position 17 of SEQ ID. NO 1 is an adenine or a cytosine; and predicting and assessing the level of risk of the subject developing a MRSA, wherein an adenine occupying the locus corresponding to position 17 of SEQ ID. NO 1 indicates that the subject has a high risk of developing a MRSA infection and a cytosine occupying the locus corresponding to position 17 of SEQ ID. NO 1, indicates that the subject has a low risk of developing a MRSA infection.

We describe embodiments wherein the detecting step further comprises hybridizing at least one oligonucleotide occupying a locus corresponding to position 17 of either SEQ ID. NO: 1, to an oligonucleotide probe comprising a sequence that is complementary or identical to SEQ ID NO. 1, under stringency conditions than can detect the presence of different alleles at position 17 of said oligonucleotide or hybridizing at least one oligonucleotide occupying a locus corresponding to position 17 of SEQ ID. NO: 2, to an oligonucleotide probe comprising a sequence that is complementary or identical to SEQ ID NO: 2, under stringency conditions that can detect the presence of different alleles at position 17 of said oligonucleotide.

We describe embodiments wherein the detecting step further comprises evaluating the hybridization of at least one oligonucleotide from the biological sample which corresponds to position 17 of SEQ ID. NO 1. and wherein the detecting step further comprises sequencing the oligonucleotide from the biological sample.

In other embodiments the detecting step further comprises amplifying the oligonucleotide from the biological sample. In some embodiments the amplifying step uses at least one oligonucleotide primer and at least one oligonucleotide from the biological sample occupying a locus corresponding to position 17 of SEQ. ID. NO. 1. The oligonucleotide primer may be comprised of DNA.

We describe methods to detect, identify and treat MRSA in all it various stages and forms including treatments make after it is determined whether the patient has a high or low risk of developing a MRSA, CA-MRSA infection or HA-MRSA and it is determined that the patient has a high risk of developing a MRSA infection, the patient is given anti MRSA antibiotics, and may also be given decolonization treatments. Once it is determined that the patient has a high risk of developing a MRSA infection, the patient may be given more than one course of anti MRSA antibiotics, decolonization treatments and may be put on high infection alert for any future surgeries.

In other embodiments after it is determined that the patient has a low risk of developing a MRSA infection, the patient is not given any antibiotics and is only treated with incision and drainage, sometimes such a low risk patient is treated with incision and drainage and given a routine antibiotic treatment that does not include anti MRSA antibiotics.

This application also describes and claims one or more primers or probes to be used to amplify or detect at least one or more nucleotides from a biological sample, wherein one or more nucleotides occupy a locus corresponding to position 17 of SEQ. ID. NO. 1. There may be one or more primers that spans the nucleotide positions about position 17 of SEQ. ID. NO. 1. The primers may be from about 8 to about 44 nucleotides in length, or from about 14 to about 50 nucleotides in length. Described are probes wherein said one or more probes span the nucleotide positions about position 17 of SEQ. ID. NO. 1. Described are probes having a different disruption energy for one allele as compared to another allele; two probes, wherein the first probe is a sensor probe and the second probe is an anchor probe; and a SNP-specific probe, in addition to methods to make and use these and other primers and probes.

In some embodiments one or more primers or probes are in a kit designed for use by a caregiver who seeks to predict or assess the level of risk of a subject developing Methicillin-resistant *S. aureus* (MRSA) infection, the kit and its instructions comprise obtaining a biological sample from the subject, wherein said biological sample includes at least one oligonucleotide occupying a locus corresponding to position 17 of SEQ ID. NO 1; detecting the identity of said at least one oligonucleotide occupying the locus corresponding to position 17 of SEQ ID. NO 1; determining whether said at least one oligonucleotide occupying the locus corresponding to position 17 of SEQ ID. NO 1 is an adenine or a cytosine; and predicting and assessing the level of risk of the subject developing a MRSA infection, wherein an adenine occupying the locus corresponding to position 17 of SEQ ID. NO 1 indicates that the subject has a high risk of developing a MRSA infection and a cytosine occupying the locus corresponding to position 17 of SEQ ID. NO 1 indicates that the subject has a low risk of developing a MRSA infection.

Disclosed are methods to monitor and prepare a patient for surgery, wherein said monitoring and preparing comprising obtaining a biological sample from the patient, wherein said biological sample includes at least one oligonucleotide occupying a locus corresponding to position 17 of SEQ ID. NO 1; detecting the identity of the at least one oligonucleotide occupying the locus corresponding to position 17 of SEQ ID. NO 1; determining whether said at least one oligonucleotide occupying the locus corresponding to position 17 of SEQ ID. NO 1 is an adenine or a cytosine; predicting and assessing the level of risk of the patient developing a MRSA infection, wherein an adenine occupying the locus corresponding to position 17 of SEQ ID. NO 1 indicates that the patient has a high risk of developing a MRSA or CA-MRSA infection and a cytosine occupying the locus corresponding to position 17 of SEQ ID. NO 1 indicates that the patient has a low risk of developing a MRSA or CA-MRSA infection; and wherein the predication and assessment indicates that the patient is at high risk for a MRSA infection, taking appropriate steps and care as one normally skilled in the art would take when operating on a person at high risk of developing a MRSA infection.

One aspect of the inventive method of determining whether a subject is at increased risk of developing MRSA and/or CA-MRSA, or a recurrence of MRSA or CA-MRSA, may include: obtaining a biological sample from the subject, wherein said biological sample contains at least one oligonucleotide comprising a loci corresponding to position 17 of SEQ ID. NO 1; detecting the identity of each nucleotide that occurs at a loci corresponding to position 17 of comparison SEQ ID. NO 1 in said at least one oligonucleotide; and comparing the identity of each nucleotide that occurs at a loci corresponding to position 17 of comparison SEQ ID. NO 1 in said at least one oligonucleotide to the identity of the nucleotide at position 17 of SEQ ID. NO 1, wherein the subject is at increased risk of developing MRSA and/or CA-MRSA, or a recurrence of MRSA or CA-MRSA if one or more nucleotides at the loci corresponding to position 17 of SEQ ID. NO 1 is the same as the identity of the nucleotide at position 17 of SEQ ID NO 1.

Another aspect of the inventive method of determining whether a subject is at increased risk of developing MRSA and/or CA-MRSA, or a recurrence of MRSA or CA-MRSA, may include: obtaining a biological sample from the subject, wherein said biological sample contains at least one oligonucleotide comprising a loci corresponding to position 17 of SEQ ID. NO 2; detecting the identity of each nucleotide that occurs at a loci corresponding to position 17 of comparison SEQ ID. NO 2 in said at least one oligonucleotide; and comparing the identity of each nucleotide that occurs at a loci corresponding to position 17 of comparison SEQ ID. NO 2 in said at least one oligonucleotide to the identity of the nucleotide at position 17 of SEQ ID. NO 2, wherein the subject is not at increased risk of developing MRSA and/or CA-MRSA, or a recurrence of MRSA or CA-MRSA if the one or more nucleotides at the loci corresponding to position 17 of SEQ ID. NO 2 in said at least one oligonucleotide is the same as the identity of the nucleotide at position 17 of SEQ ID NO 2.

In other aspects, the detecting step may further comprise hybridization of said at least one oligonucleotide comprising a loci corresponding to position 17 of SEQ ID NO. 1 to a probe comprising an oligonucleotide comprising a sequence complementary or identical to SEQ ID NO: 1, under stringency conditions than can detect the presence of different alleles at position 17 of said oligonucleotide. In other aspects, the detecting step may further comprise hybridization of said at least one oligonucleotide comprising a loci corresponding to position 17 of SEQ ID NO. 2 to a probe comprising an oligonucleotide comprising a sequence complementary or identical to SEQ ID NO. 2, under stringency conditions than can detect the presence of different alleles at position 17 of said oligonucleotide. In other aspects, the detecting step further comprises evaluating the hybridization of an oligonucleotide containing a locus corresponding to position 17 of comparison SEQ ID NO: 1 or 2 derived from said subject to a probe comprising a sequence complementary or identical to SEQ ID NO: 1 or 2, under stringency conditions that can determine the presence of different alleles at position 17 of said oligonucleotide.

In other aspects, the detecting step may further comprise amplifying at least one oligonucleotide from said biological sample containing a locus corresponding to position 17 of comparison SEQ ID. NO 1, wherein said amplifying step uses at least one oligonucleotide primer. In other aspects, the detecting step further comprises amplifying at least one oligonucleotide from said biological sample containing a locus corresponding to position 17 of comparison SEQ ID. NO 2, wherein said amplifying step uses at least one oligonucleotide primer. In some aspects, the oligonucleotide primer comprises DNA.

In other aspects, the determining step may further comprise using a probe to detect the presence of a locus corresponding to position 17 of comparison SEQ ID. NO 1 in the biological sample. In other aspects, the determining step may further comprise using a probe to detect the presence of a locus corresponding to position 17 of comparison SEQ ID. NO 2 in the biological sample.

In other aspects, the probe may be labeled with a detection signal. In other aspects, the probe may comprise an oligonucleotide having a sequence that is complementary or identical to a region flanking the locus corresponding to position 17 of comparison SEQ ID. NO 1 and/or 2, or the probe may be complementary or identical to SEQ ID NO 1 and/or 2.

In other aspects, the method may further comprise treating the subject with an antibiotic effective against MRSA, when the subject is found to be at increased risk of developing MRSA, CA-MRSA or having a recurrence of MRSA or CA-MRSA. In other aspects, the method may further comprise treating the subject to remove or prevent colonization by skin-surface or intranasal populations of MRSA, when the subject is found to be at increased risk of developing MRSA, CA-MRSA or having a recurrence of MRSA or CA-MRSA.

Embodiments of the present invention may comprise a kit for determining whether a subject is at increased risk of developing MRSA, CA-MRSA, or a recurrence of MRSA and/or CA-MRSA, comprising at least one primer for amplification of one or more nucleotides that occur at a loci corresponding to position 17 of comparison SEQ ID. NOS. 1, 2 or a combination thereof from a biological sample from the subject.

Other embodiments of the present invention may comprise a kit for determining whether a subject is at increased risk of developing MRSA, CA-MRSA, or a recurrence of MRSA and/or CA-MRSA, comprising at least one probe for detection of one or more nucleotides that occur at a loci corresponding to position 17 of comparison SEQ ID. NOS. 1, 2 or a combination thereof from a biological sample from the subject.

DETAILED DESCRIPTION

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All references, patents, patent publications, articles, and databases, referred to in this application are incorporated herein by reference in their entirety, as if each were specifically and individually incorporated herein by reference. Such patents, patent publications, articles, and databases are incorporated for the purpose of describing and disclosing the subject components of the invention that are described in those patents, patent publications, articles, and databases, which components might be used in connection with the presently described invention. The information provided below is not admitted to be prior art to the present invention, but is provided solely to assist the understanding of the reader.

The details of one or more embodiments of the invention are set forth in the accompanying drawings and the description below. Other features, embodiments, and advantages of the invention will be apparent from the description and drawings, and from the claims. The preferred embodiments of the present invention may be understood more readily by reference to the following detailed description of the specific embodiments and the Examples included hereafter.

For clarity of disclosure, and not by way of limitation, the detailed description of the invention is divided into the subsections that follow.

Definitions

Unless defined otherwise, all technical and scientific terms used herein have the meaning commonly understood by one of ordinary skill in the art to which this invention belongs. Generally, the nomenclature used herein and the laboratory procedures in cell culture, molecular genetics, organic chemistry and nucleic acid chemistry described below are those well-known and commonly employed in the art. Although any methods, devices and materials similar or equivalent to those described herein can be used in the practice or testing of the invention, the preferred methods, devices and materials are now described.

In this specification and the appended claims, the singular forms "a," "an" and "the" include plural reference unless the context clearly dictates otherwise.

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook et al. (2001) Molecular Cloning: A Laboratory Manual, 3rd ed., Cold Spring Harbor Press; DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting.

In describing the present invention, the following terms will be employed and are intended to be defined as indicated below.

The expression "anti-MRSA antibiotics" refers to antibiotics that one ordinarily skilled in the art would understand to be antibiotics usually used to treat antibiotic resistant infections like MRSA. Examples of such drugs include Vancomycin, Daptomycin, Linezolid, Ceftaroline, and Telavancin, among other antibiotics.

The term, "biological sample" means any material or fluid (blood, lymph, etc.) derived from the body of a subject, that contains or may contain genomic DNA (chromosomal and mitochondrial DNA) or other oligonucleotides such as, for example, mRNA that derive from genomic DNA. Also included within the meaning of the term "biological sample" is an organ or tissue extract and culture fluid in which any cells or tissue preparation from a subject has been incubated. Methods of obtaining biological samples and methods of obtaining oligonucleotide molecules such as DNA and RNA from a biological sample are well known in the art.

As used herein, the terms "complementary" or "complementarity" are used in reference to oligonucleotides related by the base-pairing rules for DNA-DNA, RNA-DNA and RNA-RNA pairing. For example, for the sequence "A-G-T," is complementary to the sequence "T-C-A." Complementarity may be "partial," in which only some of the nucleic acid base pairs are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Under "low stringency" conditions, strands with a lower degree of complementarity will hybridize with each other. Under "high stringency conditions," only strands with a higher degree of complementarity will remain hybridized with each other.

"Complementary" may be modified, as in the term "completely complementary," refers to an oligonucleotide where all of the nucleotides are complementary to a target sequence (e.g., a miRNA). A completely complementary oligonucleotide may be shorter than the target sequence, thus, only hybridizing to a portion of the target.

"Complementary" may be modified, as in the term "partially complementary" refers to an oligonucleotide where at least one nucleotide is not complementary to (i.e., one or more "mismatches" with) the target sequence. Preferred partially complementary oligonucleotides are those that can still hybridize to a target sequence under physiological conditions. A particular partially complementary oligonucleotide may have a 'random' pattern of one or more mismatches with the target sequence throughout the oligonucleotide (although the pattern of mismatches is preferentially constrained by retention of the ability to still hybridize to the target sequence under physiological conditions). A particular partially complementary oligonucleotide may have regions where the oligonucleotide sequence is highly, or even completely complementary to a target sequence, and regions where the oligonucleotide is not complementary, or is less complementary to the target sequence.

"Complementary" is illustrated, for example, partially complimentary oligonucleotides may have one or more regions that hybridize to a target sequence, and one or more regions that do not hybridize to the target sequence. Thus, a partially complementary sequence (such as a PCR or reverse transcriptase (RT) primer) may hybridize to a portion (i.e., the middle, the 5', or 3' end) of a particular target sequence, and not hybridize with the rest of the target sequence. Oligonucleotides with mismatches at the ends may still hybridize to the target sequence. Partially complementary sequences may be capable of binding to a sequence having less than 60%, 70%, 80%, 90%, 95%, to less than 100% identity to the target sequence. For purposes of defining or categorizing partially complementary sequences, a partially complementary sequence or region of a sequence becomes more complementary or becomes "highly complementary" as it approaches 100% complementarity to a target sequence.

Thus, a highly complementary sequence may have 60%, 70%, 80%, 90%, 95%, to 99% identity to all or a portion of a target sequence. The exact percentage identity of the highly complementary sequence may depend on the length of the highly complementary sequence and the desired stringency and specificity of hybridization. Partially complementary sequences may hybridize to one or more target sequences. As we note, partially complementary sequences may be completely complementary or highly complementary to a portion of the target sequence, such that they are completely or highly complementary to, e.g., 5%, 10%, 20%, 30%, 40%, 50% 60%, 70%, 80%, 90%, 95%, 99% of the target sequence. Similarly, 5%, 10%, 20%, 30%, 40%, 50% 60%, 70%, 80%, 90%, 95%, 99% of the partially complementary sequence may be completely complementary or highly complementary to all or a portion of the target sequence.

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time.

By the term "detectable moiety" is meant, for the purposes of the specification or claims, a label molecule (isotopic or non-isotopic) which is incorporated indirectly or directly into an oligonucleotide, wherein the label molecule facilitates the detection of the oligonucleotide in which it is incorporated, for example when the oligonucleotide is hybridized to amplified gene polymorphic sequences. Thus, "detectable moiety" is used synonymously with "label molecule". Synthesis of oligonucleotides can be accomplished by any one of several methods known to those skilled in the art. Label molecules, known to those skilled in the art as being useful for detection, include chemiluminescent, fluorescent or luminescent molecules. Various fluorescent molecules are known in the art which are suitable for use to label a nucleic acid for the method of the present invention. The protocol for such incorporation may vary depending upon the fluorescent molecule used. Such protocols are known in the art for the respective fluorescent molecule.

A "diagnosis" of MRSA or CA-MRSA may include the early detection of the disease or a confirmation of a diagnosis of the disease that has been made from other signs and/or symptoms. A "diagnosis" can include a diagnosis of increased risk of development or recurrence of MRSA or CA-MRSA. A diagnosis may include a "prognosis," that is, a future prediction of the progression of MRSA or CA-MRSA, based on the presence or absence of one or more SNPs associated with MRSA or CA-MRSA. A diagnosis or prognosis may be based on one or more samplings of DNA or RNA from a biological sample obtained from a subject. An "increased risk" of developing MRSA or CA-MRSA may be diagnosed by the presence of one or more SNPs characteristic of a phenotype of susceptibility to recurrent CA-MRSA in otherwise asymptomatic or undiagnosed subjects.

"DNA amplification" as used herein refers to any process that increases the number of copies of a specific DNA sequence by enzymatically amplifying the nucleic acid sequence. A variety of processes are known. One of the most commonly used is polymerase chain reaction (PCR). PCR involves the use of a thermostable DNA polymerase, known sequences as primers, and heating cycles, which separate the replicating deoxyribonucleic acid (DNA), strands and exponentially amplify a gene of interest. Any type of PCR, such as quantitative PCR, RT-PCR, hot start PCR, LAPCR, multiplex PCR, touchdown PCR, real-time PCR, etc., may be used. In general, the PCR amplification process involves a cyclic enzymatic chain reaction for preparing exponential quantities of a specific nucleic acid sequence. It requires a small amount of a sequence to initiate the chain reaction and oligonucleotide primers that will hybridize to the sequence. In PCR, the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

A DNA "coding sequence" or a "nucleotide sequence encoding" a particular protein is a DNA sequence that is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence. "Non-coding" genomic sequences may include regulatory, RNA transcription sequences (rRNA, tRNA, miRNA, etc.), introns and other non-gene sequences, such as structural sequences, putatively non-functional sequences ("junk DNA") and the like.

The terms "enzymatically amplify", "enzymatically amplifying", "amplify" and "amplifying" is meant, for the purposes of the specification or claims, DNA amplification, i.e., a process by which nucleic acid sequences are amplified in number. There are several means for enzymatically amplifying nucleic acid sequences. Currently the most commonly used method is the polymerase chain reaction (PCR). Other amplification methods include LCR (ligase chain reaction) which utilizes DNA ligase, and a probe consisting of two halves of a DNA segment that is complementary to the sequence of the DNA to be amplified, enzyme QB replicase and a ribonucleic acid (RNA) sequence template attached to a probe complementary to the DNA to be copied which is used to make a DNA template for exponential production of complementary RNA; strand displacement amplification (SDA); Qβ-replicase amplification (QβRA); self-sustained replication (3 SR); and NASBA (nucleic acid sequence-based amplification), which can be performed on RNA or DNA as the nucleic acid sequence to be amplified.

A "fragment" of a molecule such as a protein or nucleic acid is meant to refer to a portion of a longer or larger amino acid or nucleotide genetic sequence.

The term "genome" refers to all the genetic material in the chromosomes of a particular organism. Its size is generally given as its total number of base pairs. Within the genome, the term "gene" refers to a locatable region of genomic sequence, corresponding to a unit of inheritance, which is associated with regulatory regions, transcribed regions and/or other functional sequence regions. "Non-gene regions" of the genome have or appear to have no functional role, but may have a structural (e.g., regions near the centromere) or unknown regulatory function. The physical development and phenotype of organisms can be thought of as a product of genes interacting with each other and with the environment. A concise definition of "gene" taking into account complex patterns of regulation and transcription, sequence conservation and non-coding RNA genes has been proposed by Gerstein et al. (Genome Research 17 (6), 669-681, 2007) "A gene is a union of genomic sequences encoding a coherent set of potentially overlapping functional products". In general, an individual's genetic characteristics, as defined by the nucleotide sequence of its genome, are known as its "genotype," while an individual's physical traits are described as its "phenotype."

By "heterozygous" or "heterozygous polymorphism" is meant that the two alleles of a diploid cell or organism at a given locus are different, that is, that they have a different nucleotide exchanged for the same nucleotide at the same place in their sequences.

By "homozygous" or "homozygous polymorphism" is meant that the two alleles of a diploid cell or organism at a given locus are identical, that is, that they have the same nucleotide for nucleotide exchange at the same place in their sequences.

By "hybridization" or "hybridizing," as used herein, is meant the formation of A-T and C-G base pairs between the nucleotide sequence of a fragment of a segment of a oligonucleotide and a complementary nucleotide sequence of an oligonucleotide. By complementary is meant that at the locus of each A, C, G or T (or U in a ribonucleotide) in the fragment sequence, the oligonucleotide sequenced has a T, G, C or A, respectively. The hybridized fragment/oligonucleotide is called a "duplex."

A "hybridization complex", such as in a sandwich assay, means a complex of nucleic acid molecules including at least the target nucleic acid and a sensor probe. It may also include an anchor probe.

A hybridization complex may be related to where two nucleic acid fragments are considered to be "selectively hybridizable" to a oligonucleotide if they are capable of specifically hybridizing to a nucleic acid or a variant thereof or specifically priming a polymerase chain reaction: (i) under typical hybridization and wash conditions, as described, for example, in Sambrook et al. supra and Nucleic Acid Hybridization, supra, (ii) using reduced stringency wash conditions that allow at most about 25-30% base pair mismatches, for example: 2×SSC, 0.1% SDS, room temperature twice, 30 minutes each; then 2×SSC, 0.1% SDS, 37° C. once, 30 minutes; then 2×SSC room temperature twice, 10 minutes each, or (iii) selecting primers for use in typical polymerase chain reactions (PCR) under standard conditions (described for example, in Saiki, et al. (1988) Science 239:487-491).

A hybridization complex may be related to the term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a nucleic acid or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° Celsius in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. (2001) Molecular Cloning: A Laboratory Manual, 3rd ed., Cold Spring Harbor Press, the contents of which are herein incorporated by reference in their entirety.

A hybridization complex may refer to "stringent conditions" which typically will be those in which the salt concentration is less than about 1.5 M sodium ion, typically about 0.01 to 1.0 M Na ion concentration (or other salts) from about pH 7.0 to about pH 8.3 and the temperature is at least about 30° Celsius for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° Celsius, and a wash in 1-2×SSC at 50 to 55° Celsius. Exemplary moderate stringency conditions include hybridization in 40 to 45% formamide, 1 M NaCl, 1% SDS at 37° Celsius, and a wash in 0.5-1×SSC at 55 to 60° Celsius. Exemplary high stringency conditions include hybridization in 50% formamide, 1 M NaCl, 1% SDS at 37° Celsius, and a wash in 0.1×SSC at 60 to 65° Celsius.

An "isolated" oligonucleotide or polypeptide is one that is substantially pure of the materials with which it is associated in its native environment. By substantially free, is meant at least 50%, at least 55%, at least 60%, at least 65%, at advantageously at least 70%, at least 75%, more advantageously at least 80%, at least 85%, even more advantageously at least 90%, at least 91%, at least 92%, at least 93%, at least 94%, at least 95%, at least 96%, at least 97%, most advantageously at least 98%, at least 99%, at least 99.5%, at least 99.9% free of these materials.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

As used herein, the term "locus" or "loci" refers to the location of a coding, regulatory or non-coding region on a chromosome. Absolute location of a region may be known to more or less precision (i.e., a locus is known to be located within a chromosome, chromosome arm, chromosome band, or to the nearest kilobase or base pair of a chromosome) due to the fact that genome length may differ slightly between individuals or the precise location of a locus is not known. A relative location may also be specified where a locus is located within a sequenced fragment of a chromosome. Pairs of genes, known as "alleles" may be present for a particular locus in organisms, such as humans, that are diploid (usually contain two copies of most chromosomes) in most cells and tissues. An individual's particular combination of alleles is referred to as its "genotype". Where both alleles are identical the individual is said to be homozygous for the trait controlled by that gene pair; where the alleles are different, the individual is said to be heterozygous for the trait. While inclusive of loci within coding regions, an "allele" may also be present at locations in non-coding regions. Certain organisms, cells or tissues may be haploid or polyploid (triploid, etc.) and have more or less than two alleles at a particular locus.

A "melting temperature" is meant the temperature at which hybridized oligonucleotide duplexes dehybridize and return to their single-stranded state. Likewise, hybridization will not occur in the first place between two oligonucleotides, or, herein, an oligonucleotide and a fragment, at temperatures above the melting temperature of the resulting duplex. It is presently advantageous that the difference in melting point temperatures of oligonucleotide-fragment duplexes of this invention be from about 1 degree C. to about 10 degrees C. so as to be readily detectable.

The term, "MRSA" means Methicillin-resistant *S. aureus*, it is a strain of *S. aureus* that has become resistant to methicillin, an antibiotic commonly used to treat ordinary *S. aureus* infections. When MRSA is acquired or develops in medical care facilities, such as hospitals, it is known as health care-associated MRSA (HA-MRSA). When MRSA develops in otherwise healthy people not exposed to hospital situations it is termed community-acquired MRSA (CA-MRSA). Here it should be understood that Methicillin-resistant *S. aureus* or MRSA includes HA-MRSA and CA-MRSA.

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but advantageously is double-stranded DNA. "DNA" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). An "isolated" nucleic acid molecule is one that is separated from other nucleic acid molecules that are present in the natural source of the nucleic acid.

A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA). A "nucleotide" refers to a nucleoside linked to a single phosphate group.

The term "oligonucleotide" refers to a series of linked nucleotide residues. The series of nucleotide residues are connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides linked by a phosphodiester backbone. Oligonucleotides may be used, for example, as primers in a PCR reaction, or as probes to detect the presence of a certain sequence in or within a nucleic acid molecule. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. A "modified oligonucleotide" refers to an oligonucleotide in which one or more natural nucleotides have been partially, substantially, or completely replaced with modified nucleotides.

The term "oligonucleotide encoding a protein" as used herein refers to a DNA fragment or isolated DNA molecule encoding a protein, or the complementary strand thereto; but, RNA is not excluded, as it is understood in the art that thymidine (T) in a DNA sequence is considered equal to uracil (U) in an RNA sequence. Thus, RNA sequences for use in the invention, e.g., for use in RNA vectors, can be derived from DNA sequences, by thymidine (T) in the DNA sequence being considered equal to uracil (U) in RNA sequences.

The following are non-limiting examples of oligonucleotides: a gene or gene fragment, exons, introns, mRNA, tRNA, rRNA, ribozymes, cDNA, recombinant oligonucleotides, branched oligonucleotides, plasmids, vectors, isolated DNA of any sequence, isolated RNA of any sequence, nucleic acid probes and primers. A oligonucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the oligonucleotide to proteins, metal ions, labeling components, other oligonucleotides or solid support.

"Percent identity" can be determined by hybridization of oligonucleotides under conditions that form stable duplexes between similar regions, followed by digestion with single-stranded-specific nuclease(s), and size determination of the digested fragments. DNA sequences that are homologous can be identified in a Southern hybridization experiment under, for example, stringent conditions, as defined for that particular system. Defining appropriate hybridization conditions is within the skill of the art. See, e.g., Sambrook et al. supra; DNA Cloning, supra; Nucleic Acid Hybridization, supra.

A "polymerase" is an enzyme that catalyzes the sequential addition of monomeric units to a polymeric chain, or links two or more monomeric units to initiate a polymeric chain. The "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a oligonucleotide chain in a template-dependent manner, thereby synthesizing a nucleic acid that is complementary to the template molecule. Polymerases may be used either to extend a primer once or repetitively or to amplify an oligonucleotide by repetitive priming of two complementary strands using two primers. A "thermostable polymerase" refers to a DNA or RNA polymerase enzyme that can withstand extremely high temperatures, such as those approaching 100° C. Often, thermostable polymerases are derived from organisms that live in extreme temperatures, such as *Thermus aquaticus*. Examples of thermostable polymerases include Taq, Tth, Pfu, Vent, deep vent, UITma, and variations and derivatives thereof.

A "primer" is an oligonucleotide, the sequence of at least of portion of which is complementary to a segment of a template DNA which is to be amplified or replicated. Typically primers are used in performing the polymerase chain reaction (PCR). A primer hybridizes with (or "anneals" to) the template DNA and is used by the polymerase enzyme as the starting point for the replication/amplification process. The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

"Probes" refer to oligonucleotides nucleic acid sequences of variable length, used in the detection of identical, similar, or complementary nucleic acid sequences by hybridization. An oligonucleotide sequence used as a detection probe may be labeled with a detectable moiety.

"Sequence identity" refers to the percent identity between two oligonucleotide or two polypeptide moieties. Genes that share a high sequence identity or similarity support the hypothesis that they share a common ancestor and are therefore homologous. Sequence homology may also indicate common function. Two DNA, or two polypeptide sequences are similar to each other and may be homologous when the sequences exhibit at least about 80%, 81%, 82%, 83%, 84%, 85%, 86%, 87%, 88%, 89%, preferably at least about 90%, 91%, 92%, 93%, 94% and most preferably at least about 95%, 96%, 97%, 98%, 99%, 99.5%, 99.9% sequence identity over a defined length of the molecules. As used herein, sequence identity also refers to sequences showing complete identity (100% sequence identity) to the specified DNA or polypeptide sequence.

A "restriction fragment" refers to a fragment of a oligonucleotide generated by a restriction endonuclease (an enzyme that cleaves phosphodiester bonds within a oligonucleotide chain) that cleaves DNA in response to a recognition site on the DNA. The recognition site (restriction site) consists of a specific sequence of nucleotides typically about 4-8 nucleotides long.

A "template" refers to a target oligonucleotide strand, for example, without limitation, an unmodified naturally-occurring DNA strand, which a polymerase uses as a means of recognizing which nucleotide it should next incorporate into a growing strand to polymerize the complement of the naturally-occurring strand. Such a DNA strand may be single-stranded or it may be part of a double-stranded DNA template. In applications of the present invention requiring repeated cycles of polymerization, e.g., the polymerase chain reaction (PCR), the template strand itself may become modified by incorporation of modified nucleotides, yet still serve as a template for a polymerase to synthesize additional oligonucleotides.

A "thermocyclic reaction" is a multi-step reaction wherein at least two steps are accomplished by changing the temperature of the reaction.

A "variance" is a difference in the nucleotide sequence among related oligonucleotides. The difference may be the deletion of one or more nucleotides from the sequence of one oligonucleotide compared to the sequence of a related oligonucleotide, the addition of one or more nucleotides or the substitution of one nucleotide for another. The terms "mutation," "polymorphism" and "variance" are used interchangeably herein. As used herein, the term "variance" in the singular is to be construed to include multiple variances; i.e., two or more nucleotide additions, deletions and/or substitutions in the same oligonucleotide.

A "single nucleotide polymorphism" or "SNP" refers to a variation in the nucleotide sequence of an oligonucleotide that differs from another related oligonucleotide by a single nucleotide difference. For example, without limitation, exchanging one A for one C, G or T in the entire sequence of oligonucleotide constitutes a SNP. It is possible to have more than one SNP in a particular oligonucleotide. For example, at one position in an oligonucleotide, a C may be exchanged for a T, at another position a G may be exchanged for an A and so on. When referring to SNPs, the oligonucleotide is most often DNA. SNPs can be found in coding regions of the genome (i.e., within an exon) or non-coding intragenic (i.e., in an intron) or intergenic regions.

RNA sequences within the scope of the invention are derived from the DNA sequences, by thymidine (T) in the DNA sequence being considered equal to uracil (U) in RNA sequences.

"Subject" or "Patient" as used herein refers to a mammal, preferably a human, in need of diagnosis and/or treatment for a condition, disorder or disease.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

Single Nucleotide Polymorphisms

Analysis of single nucleotide polymorphisms (SNPs) have proved to be effective in discovering genomic differences (i.e., genotypes) in individuals or populations exhibiting different phenotypes, such as susceptibility or increased risk of contracting certain diseases or syndromes. With the advent of rapid sequencing, amplification and high throughput screening of oligonucleotides, analysis of SNPs can be used to probe individual and population genomes for one or more SNPs that correlate with (are "markers" for) the presence of a certain phenotype. Discovery of one or more reliably correlating markers (among other uses) allows for early diagnosis of potential susceptibility or risk for certain diseases, even where a phenotype is not yet being exhibited in a particular individual, e.g., a late-onset cancer or susceptibility to a disease organism prior to exposure. Here, we disclose that a SNP at a loci corresponding to position 17 of SEQ ID. NOs 1 or 2 (the FAM129B gene) can be manipulated, evaluated and then used to differentiate, identify and in some cases treat subjects who are at increased risk of MRSA and/or CA-MRSA, or a recurrence of MRSA or CA-MRSA.

Often, SNP detection methods can distinguish between homozygous and heterozygous individuals. The presence of zero, zero or one, one, one or two, or two copies of a particular base substitution allele may correlate with a particular phenotype. "Dominant," "recessive" and "intermediate dominance"/"incomplete dominance" of a particular allele at a locus can be defined as the relative contribution of each allele to the phenotype of a heterozygous individual. For example, where a heterozygous individual carrying one copy of allele A and one copy of allele A' has the same phenotype as a homozygous AA individual, and a different phenotype from a homozygous A'A' individual, allele A is dominant over allele A'. Where a heterozygous individual AA' exhibits a different or intermediate phenotype between the homozygote phenotypes, allele A' and A are said to exhibit an intermediate or incomplete dominance.

While SNPs occur at particular locations in the genome, presentation, identification and comparison of the location of particular SNPs is aided by inclusion of the sequence of nucleotides immediately upstream and downstream in the genome. SNP detection methods using oligonucleotide hybridization methods may use the same sequence as presented herein as all or part of a primer or probe sequence, and thus such sequences may serve as examples of an appropriate primer or probes for these methods. Persons of skill in the art realize that design of appropriate primers and probes, examples of which are provided below, are not necessarily limited to the sequences listed herein for purposes of presentation, and may be longer or shorter, and include more or less of the upstream and downstream flanking sequence(s), as long as they encompass the location of a SNP.

Methods and materials of the invention may be used more generally to evaluate a DNA sample from a subject, genetically type the subject, and detect genetic differences between subjects. In one embodiment of the invention, a biological sample which includes DNA from a subject is evaluated to detect the genotype of the subject for a nucleotide that occurs at a loci corresponding to position 17 of SEQ ID. NOs 1 or 2. A sample of genomic DNA from a subject may be evaluated by reference to one or more controls to determine if a SNP or group of SNPs is present. With this present invention, any method for determining genotype can be used for determining the genotype of the subject. Such methods include, but are not limited to, amplimer sequencing, DNA sequencing, fluorescence spectroscopy, fluorescence resonance energy transfer (or "FRET")-based hybridization analysis, high throughput screening, mass spectroscopy, microsatellite analysis, nucleic acid hybridization, polymerase chain reaction (PCR), RFLP analysis and size chromatography (e.g., capillary or gel chromatography), all of which are well known to one of skill in the art. In particular, methods for determining nucleotide polymorphisms, particularly single nucleotide polymorphisms, are described in U.S. Pat. Nos. 6,514,700; 6,503,710; 6,468,742; 6,448,407; 6,410,231; 6,383,756; 6,358,679; 6,322,980; 6,316,230; and 6,287,766 and reviewed by Chen and Sullivan, Pharmacogenomics J 2003; 3(2):77-96, the disclosures of which are incorporated by reference in their entireties. Genotypic data useful in the methods of the invention and methods for the identification and selection of genes associated with CA-MRSA are based on the presence of SNPs.

A Single Nucleotide Polymorphism Associated with CA-MRSA

Genomic DNA was obtained from a population of patients with recurrent CA-MRSA as well as from healthy spouse controls, who were likely to have been exposed to the same MRSA bacteria as the recurrent CA-MRSA patients. A microarray hybridization assay for single nucleotide polymorphism (SNP) alleles that segregated between the CA-MRSA and control populations was performed that was capable of detecting the presence of 906,000 known polymorphisms as well as their copy number in each subject (i.e., that could detect, whether the subject had multiple gene copies, and whether the subject was homozygous or heterozygous for particular allele(s) at a particular locus.)

A highly segregated SNP was found in the FAM129B gene, where all CA-MRSA subjects tested had two copies (homozygous) of one allele and control subjects had two copies (homozygous) of another allele. This SNP is present at a loci corresponding to position 17 of SEQ ID NOs. 1 and 2, wherein each of SEQ ID NOs. 1 and 2 identify an alternate oligonucleotide at that position. More specifically, SEQ ID NO. 1 identifies an "A" (adenine) at position 17 and SEQ ID NO. 2 identifies a "C" (cytosine) at position 17. This SNP is located in an intron of the FAM129B gene. SEQ ID NOs. 1 and 2 generally correspond with positions 17444-17464 of SEQ ID NO. 3, the full-length DNA sequence of the FAM129B gene.

Subjects with at least one or more copies of the allele corresponding to position 17 of SEQ ID. NO 1 are at increased risk of developing at developing MRSA and/or CA-MRSA, or a recurrence of MRSA or CA-MRSA. And subjects with at least one or more copies of the allele corresponding to position 17 of SEQ ID. NO 2 are not at increased risk of developing at developing MRSA and/or CA-MRSA, or a recurrence of MRSA or CA-MRSA.

The FAM129B gene encodes a protein that has a predicted molecular mass of 83 kDa, and contains a pleckstrin homology domain and a proline-rich region that contains six serine phosphorylation sites (Chen et al (2011) J. Biol. Chem. 286(12):10201-10209; Old et al. (2009) Mol. Cell 34: 115-131). Phosphorylation has been associated with MAP kinase signaling cascade; in melanoma cells the MAP kinase pathway was active and the FAM129B protein was localized throughout the cytoplasm. When the MAP kinase pathway was inhibited, the FAM129B protein migrated to the cell membrane and melanoma cell migration through a collagen matrix was inhibited. (Old et al., p. 125). Subsequent work found that FAM129B was cytoplasmically localized in actively growing HeLa cells, but appeared to be localized at cell-cell junctions on the plasma membrane when the HeLa cells achieved confluence, and throughout the cell membrane during telophase. (Chen et al. pp. 10203-10204.) FAM129B also inhibited apoptosis in HeLa cells treated with TNFα or CHX, compared with knockdown FAM129B HeLa cells silenced with siRNA sequences specific to FAM129B. A recent investigation of the corresponding Fam129B protein in mice showed that Fam129B is expressed in the epidermal keratinocytes in embryonic and adult mice. Fam129B-knockout mice exhibited delayed wound healing and had altered expression of several wound-repair and cell-motility related genes (Oishi et al. (published online Sep. 11, 2012), *J. Biochem. doi*:10.1093/jb/mvs100).

Methods of Diagnosing Increased Risk of Developing MRSA

Aspects of the present invention comprise methods of determining whether a subject is at increased risk of developing MRSA or CA-MRSA, or a recurrence of MRSA or CA-MRSA, comprising: obtaining a biological sample from a subject; obtaining at least one oligonucleotide from said biological sample that contains a loci corresponding to position 17 of SEQ ID. NOs 1 and 2; detecting in the oligonucleotide the identity of a nucleotide that occurs at a loci corresponding to position 17 of SEQ ID. NOs 1 and 2; and comparing the identity of the nucleotide that occurs at a loci corresponding to position 17 of SEQ ID. NOs 1 and 2 in the oligonucleotide to the identity of a nucleotide at position 17 of SEQ ID. NO 1 and/or SEQ ID. NO 2, wherein the subject is at increased risk of developing MRSA and/or CA-MRSA, or a recurrence of MRSA or CA-MRSA if the nucleotide that occurs at the loci corresponding to position 17 of SEQ ID. NOs 1 and 2 in the oligonucleotide is the same as the identity of the nucleotide at position 17 of SEQ ID NO 1, and wherein the subject is not at increased risk of developing MRSA and/or CA-MRSA, or a recurrence of MRSA or CA-MRSA if the nucleotide that occurs at the loci corresponding to position 17 of SEQ ID. NOs 1 and 2 in the oligonucleotide is the same as the identity of the nucleotide at position 17 of SEQ ID NO 2.

Obtaining oligonucleotides from subjects. Biological samples may be any material or fluid (blood, lymph, etc.) derived from the body of a subject, that contains or may contain genomic DNA (chromosomal and mitochondrial DNA) or other oligonucleotides such as, for example, mRNA that derive from genomic DNA, or an organ or tissue extract and culture fluid in which any cells or tissue preparation from a subject has been incubated. Methods of obtaining biological samples and methods of obtaining oligonucleotide molecules such as DNA and RNA from a biological sample are well known in the art, such as blood draws, cheek cell swabs, biopsies and the like.

For purposes of obtaining at least one oligonucleotide from said biological sample that contains a loci corresponding to position 17 of SEQ ID. NO 1 and 2, DNA or other oligonucleotides, such as pre-mRNA, can be extracted or partially purified from the biological sample for further processing by techniques known to those skilled in the art (see, e.g., U.S. Pat. Nos. 6,548,256 and 5,989,431; Hirota et al. (1989) Jinrui Idengaku Zasshi. 34: 217-23 and John et al. (1991) Nucleic Acids Res. 19:408, the disclosures of which are incorporated by reference in their entireties). For example, high molecular weight DNA may be purified from cells or tissue using proteinase K extraction and ethanol precipitation. DNA, however, may be extracted from an animal specimen using any other suitable methods known in the art.

Alternatively, a purification step may be not be needed where probes such as those described below may operate to detect the presence of a SNP by directly hybridizing to genomic DNA in situ in the biological sample, such that obtaining at least one oligonucleotide from said biological sample that contains a loci corresponding to position 17 of SEQ ID. NO 1 and 2 may occur without an oligonucleotide extraction step from the biological sample. The biological sample may be partially processed (i.e., homogenization, partial purification) prior to hybridization to facilitate the hybridization step.

Detecting SNP Polymorphisms

Any method of detecting the identity of individual nucleotides at SNP loci may be used to practice this invention.

In one aspect, detecting the identity of the SNP corresponding to position 17 of SEQ ID NOs:1 and 2 of the present invention may be performed by sequencing the region of the genomic DNA sample that spans the FAM129B polymorphic locus. Many methods of sequencing genomic DNA are known in the art, and any such method can be used, see for example, Sambrook et al. (2001) Molecular Cloning: A Laboratory Manual, 3rd ed., Cold Spring Harbor Press. For instance, as described below, a DNA restriction fragment spanning the location of the SNP of interest can be amplified using the polymerase chain reaction, then subjected to further genomic sequencing methods.

In other aspects, detecting the identity of the SNP corresponding to position 17 of SEQ ID NOs:1 and 2 of the present invention may be performed by the use of allele-specific probes that hybridize to a region of DNA containing the allele of interest. The probes may be further tagged with a detection signal to aid in detecting the presence of the allele in the biological sample. Probes and detection signals are described below.

A. Amplification

A genomic oligonucleotide spanning the location of the SNP of interest in the FAM129B gene may also be amplified as part of the detection step. More specifically, detecting the identity of SNP of the present invention may comprise DNA amplification to amplify specific, genomic sequences containing the SNP correlated to healthy and/or recurrent CA-MRSA subject phenotypes, by one of several known methods of DNA amplification, such as PCR. As noted above, the PCR amplification process involves a cyclic enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

The methods of the present invention may use oligonucleotide primers to amplify specific, genomic sequences containing the SNP correlated to healthy and/or recurrent CA-MRSA subject phenotypes. Such primers should be of sufficient length to enable specific annealing or hybridization to the nucleic acid sample. The sequences typically will be about 8 to about 44 nucleotides in length. Longer sequences, e.g., from about 14 to about 50, may be advantageous for certain embodiments. The design of primers is well known to one of ordinary skill in the art. Primers may comprise sequences upstream or downstream of the location of the SNP, but not contain the SNP itself (begin or end at, e.g., 1-1000 base pairs upstream or downstream of the location of the SNP), or comprise a sequence comprising the SNP. Such primers may be used to specifically amplify one allele or another at that SNP location. In any case, primers should be designed such that the SNP is contained within the amplified sequence. For instance, suitable primers may be designed using sequences within SEQ ID NO:3 (the FAM129B gene) upstream or downstream from the location of the SNP at position 17 of SEQ ID NOs 1 and 2.

Where it is desired to amplify a fragment of DNA that comprises a SNP according to the present invention, the forward and reverse primers may have contiguous stretches of about 8, 9, 10, 11, 12, 13, 14, 15, 16, 17, 18, 19, 20, 21, 22, 23, 24, 25, 26, 27, 28, 29, 30 or any other length up to and including about 50 nucleotides in length. The sequences to which the forward and reverse primers anneal are advantageously located on either side of the particular nucleotide position that is substituted in the SNP to be amplified (e.g., position 17 of SEQ ID NOs 1 and 2).

Oligonucleotide primers can be produced by a conventional production process for general oligonucleotides. They can be produced, for example, by a chemical synthesis process or by a microbial process that makes use of a plasmid vector, a phage vector or the like. Further, it is suitable to use a nucleic acid synthesizer.

B. Oligonucleotide Sequencing

As noted above, detecting the identity of the SNP corresponding to position 17 of SEQ ID NOs. 1 and 2 of the present invention may be performed by sequencing the region of the genomic DNA sample that spans the FAM129B polymorphic locus. Reagents allowing the sequencing of reaction products can be utilized herein. For example, chain-terminating nucleotides will often be incorporated into a reaction product during one or more cycles of a reaction. Commercial kits containing the reagents most typically used for these methods of DNA sequencing are available and widely used. PCR exonuclease digestion methods for DNA sequencing can also be used. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can be amplified using the polymerase chain reaction or some other cyclic polymerase mediated amplification reaction. The amplified region of DNA can then be sequenced using any method known in the art. Advantageously, the nucleic acid sequencing is by automated methods (reviewed by Meldrum, (2000) Genome Res. 10: 1288-303, the disclosure of which is incorporated by reference in its entirety), for example using a Beckman CEQ 8000 Genetic Analysis System (Beckman Coulter Instruments, Inc.). Methods for sequencing nucleic acids include, but are not limited to, automated fluorescent DNA sequencing (see, e.g., Watts & MacBeath, (2001) Methods Mol. Biol. 167: 153-70 and MacBeath et al. (2001) Methods Mol. Biol. 167:119-52), capillary electrophoresis (see, e.g., Bosserhoff et al. (2000) Comb Chem High Throughput Screen. 3: 455-66), DNA sequencing chips (see, e.g., Jain, (2000) Pharmacogenomics. 1: 289-307), mass spectrometry (see, e.g., Yates, (2000) Trends Genet. 16: 5-8), pyrosequencing (see, e.g., Ronaghi, (2001) Genome Res. 11: 3-11), and ultrathin-layer gel electrophoresis (see, e.g., Guttman & Ronai, (2000) Electrophoresis. 21: 3952-64), the disclosures of which are hereby incorporated by reference in their entireties. The sequencing can also be done by a commercial company. Examples of such companies include, but are not limited to, the University of Georgia Molecular Genetics Instrumentation Facility (Athens, Ga.) or SeqWright DNA Technologies Services (Houston, Tex.).

C. Oligonucleotide Hybridization

Detecting the identity of a SNP corresponding to position 17 of SEQ ID NOs. 1 and 2 of the present invention may be performed by the use of allele-specific probes that hybridize to a region of DNA containing the allele of interest.

One example method for determining the genotype at the polymorphic locus encompasses obtaining a biological sample that includes a nucleic acid sample, hybridizing the nucleic acid sample with a probe, and disrupting the hybridization to determine the level of disruption energy required wherein the probe has a different disruption energy for one allele as compared to another allele. In one example, there can be a lower disruption energy, e.g., melting temperature, for an allele that harbors a cytosine residue at a polymorphic locus, and a higher required energy for an allele with a different residue at that polymorphic locus. This can be achieved where the probe has 100% sequence identity with one allele (a perfectly matched probe), but has a single mismatch with the alternative allele. Since the perfectly matched probe is bound more tightly to the target DNA than the mismatched probe, it requires more energy to cause the hybridized probe to dissociate.

In a further step of the above method, a second ("anchor") probe may be used. Generally, the anchor probe is not specific to either allele, but hybridizes regardless of what nucleotide is present at the polymorphic locus. The anchor probe does not affect the disruption energy required to disassociate the hybridization complex but, instead, contains a complementary label for using with the first ("sensor") probe.

Hybridization stability may be influenced by numerous factors, including thermoregulation, chemical regulation, as well as electronic stringency control, either alone or in combination with the other listed factors. Through the use of stringency conditions, in either or both of the target hybridization step or the sensor oligonucleotide stringency step, rapid completion of the process may be achieved. This is desirable to achieve properly indexed hybridization of the target DNA to attain the maximum number of molecules at a test site with an accurate hybridization complex. By way of example, with the use of stringency, the initial hybridization step may be completed in ten minutes or less, more advantageously five minutes or less, and most advantageously two minutes or less. Overall, the analytical process may be completed in less than half an hour.

In one mode, the hybridization complex is labeled and the step of determining the amount of hybridization includes detecting the amounts of labeled hybridization complex at the test sites. The detection device and method may include, but is not limited to, optical imaging, electronic imaging, imaging with a CCD camera, integrated optical imaging, and mass spectrometry. Further, the amount of labeled or unlabeled probe bound to the target may be quantified. Such quantification may include statistical analysis. The labeled portion of the complex may be the target, the stabilizer, the probe or the hybridization complex in toto. Labeling may be by fluorescent labeling selected from the group of, but not limited to, Cy3, Cy5, Bodipy Texas Red, Bodipy Far Red, Lucifer Yellow, Bodipy 630/650-X, Bodipy R6G-X and 5-CR 6G. Colorimetric labeling, bioluminescent labeling and/or chemiluminescent labeling may further accomplish labeling. Labeling further may include energy transfer between molecules in the hybridization complex by perturbation analysis, quenching, electron transport between donor and acceptor molecules, the latter of which may be facilitated by double stranded match hybridization complexes. Optionally, if the hybridization complex is unlabeled, detection may be accomplished by measurement of conductance differential between double stranded and non-double stranded DNA. Further, direct detection may be achieved by porous silicon-based optical interferometry or by mass spectrometry. In using mass spectrometry no fluorescent or other label is necessary. Rather detection is obtained by extremely high levels of mass resolution achieved by direct measurement, for example, by time of flight (TOF) or by electron spray ionization (ESI). Where mass spectrometry is contemplated, probes having a nucleic acid sequence of 50 bases or less are advantageous.

The label may be amplified, and may include, for example, branched or dendritic DNA. If the target DNA is purified, it may be un-amplified or amplified. Further, if the purified target is amplified and the amplification is an exponential method, it may be, for example, PCR amplified DNA or strand displacement amplification (SDA) amplified DNA. Linear methods of DNA amplification such as rolling circle or transcriptional runoff may also be used.

A detectable label can be incorporated into a nucleic acid during at least one cycle of an amplification reaction. Spectroscopic, photochemical, biochemical, immunochemical, electrical, optical or chemical means can detect such labels. Useful labels in the present invention include fluorescent dyes (e.g., fluorescein isothiocyanate, Texas red, rhodamine, and the like), radiolabels (e.g., $^3H$, $^{125}I$, $^{35}S$, $^{14}C$, $^{32}P$, etc.), enzymes (e.g., horseradish peroxidase, alkaline phosphatase etc.), calorimetric labels such as colloidal gold or colored glass or plastic (e.g., polystyrene, polypropylene, latex, etc.) beads. The label is coupled directly or indirectly to a component of the assay according to methods well known in the art. As indicated above, a wide variety of labels are used, with the choice of label depending on sensitivity required, ease of conjugation with the compound, stability requirements, available instrumentation, and disposal provisions. Non-radioactive labels are often attached by indirect means. Polymerases can also incorporate fluorescent nucleotides during synthesis of nucleic acids.

To label an oligonucleotide with the fluorescent dye, one of several conventionally known labeling methods can be used (Tyagi & Kramer (1996) Nature Biotechnology 14: 303-308; Schofield et al. (1997) Appl. and Environ. Microbiol. 63: 1143-1147; Proudnikov & Mirzabekov (1996) Nucl. Acids Res. 24: 4532-4535). Alternatively, the oligonucleotide may be labeled with a radiolabel e.g., $^3H$, $^{125}I$, $^{35}S$, $^{14}C$, $^{32}P$, etc. Well-known labeling methods are described, for example, in Sambrook et al. (2001) Molecular Cloning: A Laboratory Manual, 3rd ed., Cold Spring Harbor Press. The label is coupled directly or indirectly to a component of the oligonucleotide according to methods well known in the art. Reversed phase chromatography or the like used to provide a nucleic acid probe for use in the present invention can purify the synthesized oligonucleotide labeled with a marker. An advantageous probe form is one labeled with a fluorescent dye at the 3'- or 5'-end and containing G or C as the base at the labeled end. If the 5'-end is labeled and the 3'-end is not labeled, the OH group on the C atom at the 3'-position of the 3'-end ribose or deoxyribose may be modified with a phosphate group or the like although no limitation is imposed in this respect.

During the hybridization of the nucleic acid target with the probes, stringent conditions may be utilized, advantageously along with other stringency affecting conditions, to aid in the hybridization. Detection by differential disruption is particularly advantageous to reduce or eliminate slippage hybridization among probes and target, and to promote more effective hybridization. In yet another aspect, stringency conditions may be varied during the hybridization complex stability determination so as to more accurately or quickly determine whether a SNP is present in the target sequence.

A SNP-specific probe can also be used in the detection of the SNP in amplified specific nucleic acid sequences of the target gene FAM129B, such as the amplified PCR products generated using the primers described above. In certain embodiments, these SNP-specific probes consist of oligonucleotide fragments. Advantageously, the fragments are of sufficient length to provide specific hybridization to the nucleic acid sample. The use of a hybridization probe of between 10 and 50 nucleotides in length allows the formation of a duplex molecule that is both stable and selective. Molecules having complementary sequences over stretches greater than 12 bases in length are generally advantageous, in order to increase stability and selectivity of the hybrid, and thereby improve the quality and degree of particular hybrid molecules obtained. One will generally prefer to design nucleic acid molecules having stretches of 16 to 24 nucleotides, or even longer where desired. A tag nucleotide region may be included, as at the 5' end of the primer that may provide a site to which an oligonucleotide sequencing primer may hybridize to facilitate the sequencing of multiple PCR samples.

The probe sequence must span the particular nucleotide position that may be substituted in the particular SNP to be detected, here, position 17 of SEQ ID. NOs 1 and 2. Advantageously, two or more different "allele-specific probes" may be used for analysis of a SNP, a first allele-specific probe for detection of one allele, and a second allele-specific probe for the detection of the alternative allele. For example, one probe could be used for detection of the adenosine at position 17 of SEQ ID NO. 1 and another probe could be used for detection of cytosine at position 17 of SEQ ID NO. 2.

It will be understood that this invention is not limited to the particular primers and probes disclosed herein and is intended to encompass at least nucleic acid sequences that are hybridizable to the nucleotide sequence disclosed herein, the complement or a fragment thereof, or are functional sequence analogs of these sequences. Homologs (i.e., nucleic acids derived from other species) or other related sequences (e.g., paralogs) can be obtained under conditions of standard or stringent hybridization conditions with all or a portion of the particular sequence as a probe using methods well known in the art for nucleic acid hybridization and cloning.

Advantageously, probes may be affixed to substrates and used in "microarray" and other high-throughput detection applications such as those used in the Example below and which are well known in the art. Microarrays can show the presence of one or both SNP alleles, copy number (such as whether an individual is homozygotic, or heterozygotic for a particular polymorphism), and thus provide a genotype for an individual subject.

D. Subjects at Increased Risk of CA-MRSA

In one embodiment of the present invention, subjects with at least one or more copies of the allele corresponding to position 17 of SEQ ID. NO 1 are at increased risk of developing MRSA and/or CA-MRSA, or a recurrence of MRSA or CA-MRSA. In another embodiment of the present invention, subjects with at least one or more copies of the allele corresponding to position 17 of SEQ ID. NO 2 are not at increased risk of developing at developing MRSA and/or CA-MRSA, or a recurrence of MRSA or CA-MRSA.

Other SNPs, or other biomarkers, such as gene or protein biomarker, miRNA and the like, the levels or presence/absence of which are correlated with increased risk of developing MRSA or CA-MRSA, or the occurrence of recurrent MRSA or CA-MRSA may also be used alone or in conjunction with the SNP of the present invention to diagnose subjects who are at increased risk of developing MRSA and/or CA-MRSA, or a recurrence of MRSA or CA-MRSA. Other SNPs or biomarkers may identify a structurally or functionally abnormal FAM129B gene caused by a point mutation(s), a deletion, a truncation, or a translocation of at least a portion of the FAM129B gene. An exemplary biomarker may identify and/or detect the presence of (a) a decrease or an increase in expression of the FAM129B gene (as compared to a control group which is not at an increased risk of developing MRSA or CA-MRSA, or recurrent MRSA or CA-MRSA) or (b) the abnormal methylation of at least a part of the FAM129B gene. In one embodiment, methods to detect a structurally or functionally abnormal FAM129B gene may include using an oligonucleotide primer that is complementary to or identical to a portion of SEQ ID NO: 3 to amplify an oligonucleotide sample from a subject (and the amplified oligonucleotides may then be sequenced); or hybridizing oligonucleotides in a sample from a subject to an oligonucleotide probe having a sequence that is complementary to or identical to a portion of SEQ ID NO: 3.

Treatment of Patients at Increased Risk of Recurrent CA-MRSA

In some aspects of the method, subjects found to be at increased risk of developing MRSA, HA-MRSA or CA-MRSA or having a recurrence of MRSA, HA-MRSA or CA-MRSA may be treated with an antibiotic effective against MRSA. In other aspects, subjects found to be at increased risk of developing MRSA or having a recurrence of MRSA can be treated with appropriate topical and/or nasal treatments to remove surface colonies of or prevent colonization by skin-surface or intranasal populations of MRSA. Appropriate treatments may be increased sanitation (more frequent hand washing with regular or antibiotic soaps such as Hibiclens (4% clorhexidine), topical antibiotic treatments, and oral antibiotics, mouth rinses and nasal ointments containing antibiotics. See, e.g., Buehlmann, M. et al. "Highly effective regimen for decolonization of methicillin-resistant *Staphylococcus aureus* carriers" Infect. Control. Hosp. Epidemiol. (2008) 29(8); 510-6.

A more aggressive treatment of a MRSA, HA-MRSA or CA-MRSA patient may involve the administration of an antibiotic regime including the repeated and/or prophylactic use of one or more anti-MRSA antibiotics such as Vancomycin, Daptomycin, Linezolid, Ceftaroline, Telavancin, Bactrim and the like. Treatment of MRSA patients often includes decolonization efforts, frequent monitoring, long term follow-up and special treatment for any further surgeries (e.g. surgical prescreening for MRSA and antibiotic treatment for prophylaxis) including long duration evaluation and monitoring for infection. Treatment for patents at low risk of MRSA infection could involve as little as incision and drainage followed by administration of a common antibiotic or in some cases with no antibiotic at all.

Kits comprising the methods and devices of the MRSA risk assessment described here in are also described and would be known to one skilled in the art given the descriptions provided.

Some embodiments of the present invention may comprise a kit for determining whether a subject is at increased risk of developing MRSA, or a recurrence of MRSA comprising at least one primer for amplification of one or more nucleotides that occur at a loci corresponding to position 17 of comparison SEQ ID. NOS. 1, 2 or a combination thereof from a biological sample from the subject.

Other embodiments of the present invention may comprise a kit for determining whether a subject is at increased risk of developing MRSA or CA-MRSA, or a recurrence of MRSA and/or CA-MRSA, comprising at least one probe for detection of one or more nucleotides that occur at a loci corresponding to position 17 of comparison SEQ ID. NOS. 1, 2 or a combination thereof from a biological sample from the subject.

Some embodiments of the invention may comprise one or more probes for use in determining whether a subject is at increased risk of developing MRSA or CA-MRSA, or a recurrence of MRSA or CA-MRSA, wherein the one or more probes comprise the oligonucleotide(s) described by SEQ ID NOs. 1 and/or 2. Other embodiments of the invention may comprise an amplification product for use in determining whether a subject is at increased risk of developing MRSA or CA-MRSA, or a recurrence of MRSA or CA-MRSA, wherein the amplification product comprises an oligonucleotide sequence comprising SEQ ID NO. 1 and/or 2. Other embodiments of the invention may comprise amplification primers for use in determining whether a subject is at increased risk of developing MRSA or CA-MRSA, or a recurrence of MRSA or CA-MRSA, wherein the amplification primers comprise oligonucleotide sequences in SEQ ID NO:3 immediately flanking the location of SEQ ID NO:1 and 2; comprise SEQ ID NO:1 or 2 and oligonucleotide sequences in SEQ ID NO:3 immediately flanking the location of SEQ ID NO:1 and 2; or comprise SEQ ID NO:1 or 2.

The invention will now be further described by way of the following non-limiting examples.

EXAMPLES

Example 1

Study Design

Fourteen participants were contacted and consented to collection of blood samples for analysis. Collection and analysis were approved through the Beaumont Institutional Review Board. Eleven participants were patients who were seen for recurrent community acquired MRSA skin infections (CA-MRSA) but had no known specific risk factors for developing recurrent infection. Three participants were controls and were cohabiting spouses of three of the patients. This gave controls who were directly and closely exposed to the patient (i.e., shared a bed) and were thus within the same environment but did not become infected with CA-MRSA.

Example 2

Methods

Collection and analysis was done via the Beaumont BioBank. Analysis was performed in an automated and blinded manner. Genomic DNA from all participants was prepared for analysis using Affymetrix Genome-wide Human SNP 6.0 microarrays. Each array contains more than 946,000 probes for detection of copy number variation and more than 906,000 single nucleotide polymorphism (SNP) probes for genotyping. One array per patient sample was prepared according to the manufacturer's protocol and scanned with an Affymetrix GeneChip® Scanner 3000. Affymetrix Genotyping Consol software and the Partek Genomics Suite were used for analysis and visualization of the data.

Data was subjected to per SNP and per sample quality control to minimize false positives. None of the remaining samples from individuals were excluded based on the expression data. SNPs from X and Y chromosomes were excluded from further analysis. SNPs with no call rates <5% and minor alleles frequencies >5% were included for further analysis. The final number of SNPs included in the analysis was 633,268.

A chi-square test was used to set the phenotype to be tested for association with the SNPs. Three models were tested:

1. Allele: frequencies of alleles (A vs. A') were compared between CA-MRSA subjects and the control subjects
2. Genotype: frequencies of three possible genotypes (AA, AA', and A'A') were compared between CA-MRSA subjects and the control subjects
3. Dominant/Recessive: two combinations of genotypes are compared between CA-MRSA subjects and the control subjects—Dominant (AA+AA' vs. A'A', with A as the causal variant) and Recessive (AA vs. AA'+A'A', with A as the causal variant)

Example 3

Results

The analysis using each model revealed several potential SNPs of interest, but the most significant (p value $1.21 \times 10^{-7}$) was located within the open reading frame of a gene identified as FAM129B. This SNP (SNP_A 8307872, rs2249861) was present with two copies of a single form in all 11 MRSA patients and with two copies of another form in all three controls. There were no participants who were heterozygous (one copy of the gene in each form).

The particular SNP in gene FAM129B which segregated between the control and CA-MRSA populations was located in an intron sequence. The SNP has the following sequence in CA-MRSA subjects: GGGGGCAAGTTAGTCAACCTGTCTGAGTCTTAG [SEQ ID NO:1] with the SNP location at position 17 underlined. Control populations had the alternate allele: GGGGGCAAGTTAGTCACCCTGTCTGAGTCTTAG [SEQ ID NO. 2] at position 17.

What is claimed is:

1. A method comprising the steps of:
    obtaining a biological sample from a human subject, wherein said biological sample comprises genomic DNA,
    analyzing the genomic DNA and detecting the presence of two copies of SEQ ID NO: 1 in the sample,
    predicting that the subject has an increased risk of developing a MRSA infection, and
    administering to the human subject anti MRSA antibiotics.

2. The method of claim 1, wherein the detecting step comprising contacting the genomic DNA with an oligonucleotide probe that comprises a locus corresponding to position 17 of SEQ ID NO: 1.

3. The method of claim 2, wherein the detecting step further comprise sequencing the oligonucleotide from the biological sample.

4. The method of claim 3, wherein the detecting step further comprises amplifying the nucleic acid that comprises instant SEQ ID NO: 1 from the genomic DNA.

5. The method of claim 4, wherein the amplifying uses at least one oligonucleotide primer.

6. The method of claim 5, wherein the oligonucleotide primer comprises DNA.

7. The method of claim 1, wherein the treating further comprises administering to the patient decolonization treatments.

8. The method of claim 7, wherein the patient is administered more than one course of anti MRSA antibiotics and is put on high infection alert for future surgeries.

9. The method of claim 1, wherein the human subject is preparing for surgery and further comprising taking additional steps to prevent infection.

10. A method comprising the steps of:
    obtaining a biological sample from a human subject, wherein said biological sample comprises genomic DNA,
    analyzing the genomic DNA and detecting the presence of two copies of SEQ ID NO: 2 in the sample,
    predicting that the subject has a decreased risk of developing a MRSA infection, and
    treating the subject with incision and drainage in the absence of antibiotics.

11. A method comprising the steps of:
    obtaining a biological sample from a human subject, wherein said biological sample comprises genomic DNA,
    analyzing the genomic DNA and detecting the presence of two copies of SEQ ID NO: 2 in the sample,
    predicting that the subject has a decreased risk of developing a MRSA infection, and
    treating the subject with incision and drainage and a common antibiotic.

* * * * *